US012558547B2

(12) United States Patent
Lee et al.

(10) Patent No.: US 12,558,547 B2
(45) Date of Patent: Feb. 24, 2026

(54) MODIFIED HIGH FREQUENCY NEUROMODULATION SIGNALS, AND ASSOCIATED SYSTEMS AND METHODS

(71) Applicant: Nevro Corp., Redwood City, CA (US)

(72) Inventors: Dongchul Lee, Agua Dulce, CA (US); Kerry Bradley, Glendale, CA (US)

(73) Assignee: Nevro Corp., Redwood City, CA (US)

( * ) Notice: Subject to any disclaimer, the term of this patent is extended or adjusted under 35 U.S.C. 154(b) by 551 days.

(21) Appl. No.: 17/824,737

(22) Filed: May 25, 2022

(65) Prior Publication Data

US 2022/0379116 A1     Dec. 1, 2022

Related U.S. Application Data

(60) Provisional application No. 63/192,998, filed on May 25, 2021.

(51) Int. Cl.
*A61N 1/36* (2006.01)

(52) U.S. Cl.
CPC ..... *A61N 1/36062* (2017.08); *A61N 1/36171* (2013.01); *A61N 1/36175* (2013.01)

(58) Field of Classification Search
CPC ............ A61N 1/36062; A61N 1/36171; A61N 1/36175
USPC ....................................................... 607/46
See application file for complete search history.

(56) References Cited

U.S. PATENT DOCUMENTS

| | | | |
|---|---|---|---|
| 1,597,061 A | 8/1926 | Cultra |
| 2,622,601 A | 12/1952 | Nemec |
| 3,195,540 A | 7/1965 | Waller |
| 3,279,468 A | 10/1966 | Vine |
| 3,449,768 A | 6/1969 | Doyle |
| 3,646,940 A | 3/1972 | Timm et al. |
| 3,724,467 A | 4/1973 | Avery et al. |
| 3,727,616 A | 4/1973 | Lenzkes |
| 3,774,618 A | 11/1973 | Avery |
| 3,817,254 A | 6/1974 | Maurer |
| 3,822,708 A | 7/1974 | Zilber |
| 3,835,833 A | 9/1974 | Limoge |
| 3,893,463 A | 7/1975 | Williams |
| 4,014,347 A | 3/1977 | Halleck et al. |
| 4,023,574 A | 5/1977 | Nemec |
| 4,055,190 A | 10/1977 | Tany et al. |
| 4,096,866 A | 6/1978 | Fischell |
| 4,148,321 A | 4/1979 | Wyss et al. |

(Continued)

FOREIGN PATENT DOCUMENTS

| | | | | |
|---|---|---|---|---|
| AU | 2017221321 A1 * | 8/2018 | ......... | A61N 1/36146 |
| AU | 2017221321 | 4/2021 | | |

(Continued)

OTHER PUBLICATIONS

Barolat et al., "Mapping of sensory responses to epidural stimulation of intraspinal neural structures in man," Journal of Neurosurgery, vol. 78, Feb. 1993, 7 pages.

(Continued)

*Primary Examiner* — Michael J Lau

(57) ABSTRACT

The present technology is directed generally to spinal cord modulation and associated systems and methods for treating pain and other patient conditions. In particular, the present technology includes modified high frequency neuromodulation signals and administration patterns.

26 Claims, 13 Drawing Sheets

(56) References Cited

U.S. PATENT DOCUMENTS

| | | | |
|---|---|---|---|
| 4,155,366 A | 5/1979 | Di Mucci | |
| 4,289,136 A | 9/1981 | Rienzo, Sr. | |
| 4,315,503 A | 2/1982 | Ryaby et al. | |
| 4,379,462 A | 4/1983 | Borkan et al. | |
| 4,414,986 A | 11/1983 | Dickhudt et al. | |
| 4,459,989 A | 7/1984 | Borkan | |
| 4,535,777 A | 8/1985 | Castel | |
| 4,541,432 A | 9/1985 | Molina-Negro et al. | |
| 4,550,733 A | 11/1985 | Liss et al. | |
| 4,607,639 A | 8/1986 | Tanagho | |
| 4,608,985 A | 9/1986 | Crish et al. | |
| 4,612,934 A | 9/1986 | Borkan et al. | |
| 4,649,935 A | 3/1987 | Charmillot et al. | |
| 4,702,254 A | 10/1987 | Zabara | |
| 4,735,204 A | 4/1988 | Sussman et al. | |
| 4,739,764 A | 4/1988 | Lue et al. | |
| 4,764,132 A | 8/1988 | Stutz, Jr. | |
| 4,784,142 A | 11/1988 | Liss et al. | |
| 4,793,353 A | 12/1988 | Borkan et al. | |
| 4,841,973 A | 6/1989 | Stecker | |
| RE33,420 E | 11/1990 | Sussman et al. | |
| 4,989,605 A | 2/1991 | Rossen | |
| 5,002,053 A | 3/1991 | Garcia-Rill | |
| 5,042,486 A | 8/1991 | Pfeiler et al. | |
| 5,052,375 A | 10/1991 | Stark et al. | |
| 5,078,140 A | 1/1992 | Kwoh | |
| 5,188,104 A | 2/1993 | Wernicke et al. | |
| 5,211,165 A | 5/1993 | Dumoulin et al. | |
| 5,257,636 A | 11/1993 | White | |
| 5,284,153 A | 2/1994 | Raymond et al. | |
| 5,306,291 A | 4/1994 | Kroll et al. | |
| 5,325,873 A | 7/1994 | Hirschi et al. | |
| 5,330,515 A | 7/1994 | Rutecki et al. | |
| 5,335,657 A | 8/1994 | Terry, Jr. et al. | |
| 5,354,320 A | 10/1994 | Schaldach et al. | |
| 5,375,596 A | 12/1994 | Twiss et al. | |
| 5,417,719 A | 5/1995 | Hull | |
| 5,425,367 A | 6/1995 | Shapiro et al. | |
| 5,501,703 A | 3/1996 | Holsheimer et al. | |
| 5,514,175 A | 5/1996 | Kim et al. | |
| 5,531,774 A | 7/1996 | Schulman et al. | |
| 5,540,730 A | 7/1996 | Terry, Jr. et al. | |
| 5,540,734 A | 7/1996 | Zabara | |
| 5,562,717 A | 10/1996 | Tippey et al. | |
| 5,573,552 A | 11/1996 | Hansjurgens et al. | |
| 5,643,330 A | 7/1997 | Holsheimer et al. | |
| 5,702,428 A | 12/1997 | Tippey et al. | |
| 5,707,396 A | 1/1998 | Benabid | |
| 5,716,377 A | 2/1998 | Rise | |
| 5,727,553 A | 3/1998 | Saad | |
| 5,755,758 A | 5/1998 | Wolozko | |
| 5,776,170 A | 7/1998 | MacDonald et al. | |
| 5,782,880 A | 7/1998 | Lahtinen et al. | |
| 5,792,187 A | 8/1998 | Adams | |
| 5,830,151 A | 11/1998 | Hadzic et al. | |
| 5,833,709 A | 11/1998 | Rise | |
| 5,853,373 A | 12/1998 | Griffith et al. | |
| 5,871,487 A | 2/1999 | Warner et al. | |
| 5,893,883 A | 4/1999 | Torgerson | |
| 5,895,416 A | 4/1999 | Barreras | |
| 5,925,070 A | 7/1999 | King | |
| 5,938,690 A | 8/1999 | Law | |
| 5,948,007 A | 9/1999 | Starkebaum et al. | |
| 5,976,110 A | 11/1999 | Greengrass et al. | |
| 5,983,141 A | 11/1999 | Sluijter et al. | |
| 5,995,872 A | 11/1999 | Bourgeois | |
| 6,002,964 A | 12/1999 | Feler et al. | |
| 6,014,588 A | 1/2000 | Fitz | |
| 6,027,456 A | 2/2000 | Feler et al. | |
| 6,049,701 A | 4/2000 | Sparksman | |
| 6,104,957 A | 8/2000 | Alo et al. | |
| 6,159,163 A | 12/2000 | Strauss et al. | |
| 6,161,044 A | 12/2000 | Silverstone | |
| 6,161,048 A | 12/2000 | Sluijter et al. | |
| 6,167,305 A | 12/2000 | Cammilli et al. | |
| 6,167,311 A | 12/2000 | Rezai | |
| 6,176,242 B1 | 1/2001 | Rise | |
| 6,192,278 B1 | 2/2001 | Werner et al. | |
| 6,198,963 B1 | 3/2001 | Haim et al. | |
| 6,233,488 B1 | 5/2001 | Hess | |
| 6,236,892 B1 | 5/2001 | Feler et al. | |
| 6,238,423 B1 | 5/2001 | Bardy | |
| 6,246,912 B1 | 6/2001 | Sluijter et al. | |
| 6,259,952 B1 | 7/2001 | Sluijter et al. | |
| 6,314,325 B1 | 11/2001 | Fitz | |
| 6,319,241 B1 | 11/2001 | King et al. | |
| 6,341,236 B1 | 1/2002 | Osorio et al. | |
| 6,356,786 B1 | 3/2002 | Rezai et al. | |
| 6,366,814 B1 | 4/2002 | Boveja | |
| 6,381,496 B1 | 4/2002 | Meadows et al. | |
| 6,393,325 B1 | 5/2002 | Mann et al. | |
| 6,397,108 B1 | 5/2002 | Camps et al. | |
| 6,405,079 B1 | 6/2002 | Ansarinia | |
| 6,421,566 B1 | 7/2002 | Holsheimer | |
| 6,438,418 B1 | 8/2002 | Swerdlow et al. | |
| 6,440,090 B1 | 8/2002 | Schallhorn | |
| 6,473,644 B1 | 10/2002 | Terry, Jr. et al. | |
| 6,474,341 B1 | 11/2002 | Hunter et al. | |
| 6,487,446 B1 | 11/2002 | Hill et al. | |
| 6,505,074 B2 | 1/2003 | Boveja et al. | |
| 6,505,078 B1 | 1/2003 | King et al. | |
| 6,510,347 B2 | 1/2003 | Borkan | |
| 6,516,227 B1 | 2/2003 | Meadows et al. | |
| 6,526,318 B1 | 2/2003 | Ansarinia | |
| 6,571,127 B1 | 5/2003 | Ben-Haim et al. | |
| 6,584,358 B2 | 6/2003 | Carter et al. | |
| 6,587,724 B2 | 7/2003 | Mann | |
| 6,587,727 B2 | 7/2003 | Osorio et al. | |
| 6,600,954 B2 | 7/2003 | Cohen et al. | |
| 6,609,030 B1 | 8/2003 | Rezai et al. | |
| 6,609,031 B1 | 8/2003 | Law et al. | |
| 6,610,713 B2 | 8/2003 | Tracey | |
| 6,622,047 B2 | 9/2003 | Barrett et al. | |
| 6,622,048 B1 | 9/2003 | Mann | |
| 6,659,968 B1 | 12/2003 | McClure | |
| 6,662,051 B1 | 12/2003 | Eraker et al. | |
| 6,671,556 B2 | 12/2003 | Osorio et al. | |
| 6,671,557 B1 | 12/2003 | Gliner | |
| 6,675,046 B2 | 1/2004 | Holsheimer | |
| 6,684,105 B2 | 1/2004 | Cohen et al. | |
| 6,687,538 B1 | 2/2004 | Hrdlicka et al. | |
| 6,701,190 B2 | 3/2004 | Gliner | |
| 6,712,753 B2 | 3/2004 | Manne | |
| 6,712,772 B2 | 3/2004 | Cohen et al. | |
| 6,714,822 B2 | 3/2004 | King et al. | |
| 6,721,603 B2 | 4/2004 | Zabara et al. | |
| 6,757,561 B2 | 6/2004 | Rubin et al. | |
| 6,795,737 B2 | 9/2004 | Gielen et al. | |
| 6,836,685 B1 | 12/2004 | Fitz | |
| 6,856,315 B2 | 2/2005 | Eberlein | |
| 6,862,479 B1 | 3/2005 | Whitehurst | |
| 6,862,480 B2 | 3/2005 | Cohen et al. | |
| 6,871,090 B1 | 3/2005 | He et al. | |
| 6,871,099 B1 | 3/2005 | Whitehurst et al. | |
| 6,875,571 B2 | 4/2005 | Crabtree et al. | |
| 6,885,888 B2 | 4/2005 | Rezai | |
| 6,892,097 B2 | 5/2005 | Holsheimer et al. | |
| 6,895,280 B2 | 5/2005 | Meadows et al. | |
| 6,907,293 B2 | 6/2005 | Grill et al. | |
| 6,907,295 B2 | 6/2005 | Gross et al. | |
| 6,920,357 B2 | 7/2005 | Osorio et al. | |
| 6,923,784 B2 | 8/2005 | Stein | |
| 6,928,320 B2 | 8/2005 | King | |
| 6,941,173 B2 | 9/2005 | Nachum | |
| 6,950,707 B2 | 9/2005 | Whitehurst | |
| 6,959,215 B2 | 10/2005 | Gliner | |
| 6,961,618 B2 | 11/2005 | Osorio et al. | |
| 6,968,237 B2 | 11/2005 | Doan et al. | |
| 6,973,346 B2 | 12/2005 | Hafer et al. | |
| 6,988,006 B2 | 1/2006 | King et al. | |
| 6,990,376 B2 | 1/2006 | Tanagho et al. | |
| 7,020,523 B1 | 3/2006 | Lu et al. | |
| 7,024,246 B2 | 4/2006 | Acosta et al. | |
| 7,024,247 B2 | 4/2006 | Gliner et al. | |

(56)　　　　　References Cited

U.S. PATENT DOCUMENTS

| | | | |
|---|---|---|---|
| 7,047,079 | B2 | 5/2006 | Erickson |
| 7,047,084 | B2 | 5/2006 | Erickson et al. |
| 7,054,686 | B2 | 5/2006 | MacDonald |
| 7,076,307 | B2 | 7/2006 | Boveja et al. |
| 7,082,333 | B1 | 7/2006 | Bauhahn et al. |
| 7,117,034 | B2 | 10/2006 | Kronberg |
| 7,127,297 | B2 | 10/2006 | Law et al. |
| 7,146,224 | B2 | 12/2006 | King |
| 7,149,574 | B2 | 12/2006 | Yun et al. |
| 7,158,826 | B1 | 1/2007 | Kroll et al. |
| 7,162,303 | B2 | 1/2007 | Levin et al. |
| 7,162,304 | B1 | 1/2007 | Bradley |
| 7,167,750 | B2 | 1/2007 | Knudson et al. |
| 7,174,215 | B2 | 2/2007 | Bradley |
| 7,177,690 | B2 | 2/2007 | Woods et al. |
| 7,177,702 | B2 | 2/2007 | Wallace et al. |
| 7,180,760 | B2 | 2/2007 | Varrichio et al. |
| 7,206,640 | B1 | 4/2007 | Overstreet |
| 7,206,642 | B2 | 4/2007 | Pardo et al. |
| 7,212,865 | B2 | 5/2007 | Cory |
| 7,212,867 | B2 | 5/2007 | Van Venroo et al. |
| 7,225,035 | B2 | 5/2007 | Brabec et al. |
| 7,228,179 | B2 | 6/2007 | Campen et al. |
| 7,231,254 | B2 | 6/2007 | DiLorenzo |
| 7,236,822 | B2 | 6/2007 | Dobak, III |
| 7,236,830 | B2 | 6/2007 | Gliner |
| 7,236,834 | B2 | 6/2007 | Christopherson et al. |
| 7,239,912 | B2 | 7/2007 | Dobak, III |
| 7,241,283 | B2 | 7/2007 | Putz |
| 7,242,984 | B2 | 7/2007 | DiLorenzo |
| 7,244,150 | B1 | 7/2007 | Brase et al. |
| 7,251,529 | B2 | 7/2007 | Greenwood-Van Meerveld |
| 7,252,090 | B2 | 8/2007 | Goetz |
| 7,254,445 | B2 | 8/2007 | Law et al. |
| 7,260,436 | B2 | 8/2007 | Kilgore et al. |
| 7,266,412 | B2 | 9/2007 | Stypulkowski |
| 7,276,057 | B2 | 10/2007 | Gerber |
| 7,288,062 | B2 | 10/2007 | Spiegel |
| 7,313,440 | B2 | 12/2007 | Miesel |
| 7,324,852 | B2 | 1/2008 | Barolat et al. |
| 7,326,181 | B2 | 2/2008 | Katims |
| 7,328,068 | B2 | 2/2008 | Spinelli et al. |
| 7,329,262 | B2 | 2/2008 | Gill |
| 7,333,857 | B2 | 2/2008 | Campbell |
| 7,337,005 | B2 | 2/2008 | Kim et al. |
| 7,337,006 | B2 | 2/2008 | Kim et al. |
| 7,343,200 | B2 | 3/2008 | Litvak et al. |
| 7,346,398 | B2 | 3/2008 | Gross et al. |
| 7,349,743 | B2 | 3/2008 | Tadlock |
| RE40,279 | E | 4/2008 | Sluijter et al. |
| 7,359,751 | B1 | 4/2008 | Erickson et al. |
| 7,363,076 | B2 | 4/2008 | Yun et al. |
| 7,381,441 | B2 | 6/2008 | Leung et al. |
| 7,386,341 | B2 | 6/2008 | Hafer et al. |
| 7,389,145 | B2 | 6/2008 | Kilgore et al. |
| 7,393,351 | B2 | 7/2008 | Woloszko et al. |
| 7,425,142 | B1 | 9/2008 | Putz |
| 7,433,734 | B2 | 10/2008 | King |
| 7,444,181 | B2 | 10/2008 | Shi et al. |
| 7,444,183 | B2 | 10/2008 | Knudson et al. |
| 7,444,184 | B2 | 10/2008 | Boveja et al. |
| 7,447,546 | B2 | 11/2008 | Kim et al. |
| 7,450,993 | B2 | 11/2008 | Kim et al. |
| 7,452,335 | B2 | 11/2008 | Wells et al. |
| 7,463,927 | B1 | 12/2008 | Chaouat |
| 7,483,747 | B2 | 1/2009 | Gliner et al. |
| 7,489,969 | B2 | 2/2009 | Knudson et al. |
| 7,493,172 | B2 | 2/2009 | Whitehurst et al. |
| 7,496,404 | B2 | 2/2009 | Meadows et al. |
| 7,502,651 | B2 | 3/2009 | Kim et al. |
| 7,502,652 | B2 | 3/2009 | Gaunt et al. |
| 7,551,964 | B2 | 6/2009 | Dobak, III |
| 7,571,007 | B2 | 8/2009 | Erickson et al. |
| 7,580,753 | B2 | 8/2009 | Kim et al. |
| 7,599,737 | B2 | 10/2009 | Yomtov et al. |
| 7,606,622 | B2 | 10/2009 | Reeve |
| 7,610,096 | B2 | 10/2009 | McDonald, III |
| 7,613,520 | B2 | 11/2009 | De Ridder |
| 7,634,317 | B2 | 12/2009 | Ben-David et al. |
| 7,676,269 | B2 | 3/2010 | Yun et al. |
| 7,689,276 | B2 | 3/2010 | Dobak |
| 7,689,289 | B2 | 3/2010 | King |
| 7,702,379 | B2 | 4/2010 | Avinash et al. |
| 7,711,432 | B2 | 5/2010 | Thimineur et al. |
| 7,715,915 | B1 | 5/2010 | Rye et al. |
| 7,734,340 | B2 | 6/2010 | De Ridder |
| 7,734,352 | B2 | 6/2010 | Greenberg et al. |
| 7,734,355 | B2 | 6/2010 | Cohen et al. |
| 7,742,810 | B2 | 6/2010 | Moffitt et al. |
| 7,761,166 | B2 | 7/2010 | Giftakis et al. |
| 7,761,168 | B2 | 7/2010 | Gross |
| 7,761,170 | B2 | 7/2010 | Kaplan et al. |
| 7,769,463 | B2 | 8/2010 | Katsnelson |
| 7,778,704 | B2 | 8/2010 | Rezai |
| 7,792,591 | B2 | 9/2010 | Rooney et al. |
| 7,801,601 | B2 | 9/2010 | Maschino et al. |
| 7,801,604 | B2 | 9/2010 | Brockway et al. |
| 7,805,189 | B2 | 9/2010 | Stein et al. |
| 7,805,197 | B2 | 9/2010 | Bradley |
| 7,809,443 | B2 | 10/2010 | Giftakis et al. |
| 7,813,803 | B2 | 10/2010 | Heruth et al. |
| 7,813,804 | B1 | 10/2010 | Jaax |
| 7,826,901 | B2 | 11/2010 | Lee et al. |
| 7,831,306 | B2 | 11/2010 | Finch et al. |
| 7,844,338 | B2 | 11/2010 | Knudson et al. |
| 7,848,818 | B2 | 12/2010 | Barolat et al. |
| 7,853,322 | B2 | 12/2010 | Bourget et al. |
| 7,856,277 | B1 | 12/2010 | Thacker et al. |
| 7,860,570 | B2 | 12/2010 | Whitehurst et al. |
| 7,865,243 | B1 | 1/2011 | Whitehurst et al. |
| 7,877,136 | B1 | 1/2011 | Moffitt et al. |
| 7,877,146 | B2 | 1/2011 | Rezai |
| 7,881,805 | B2 | 2/2011 | Bradley |
| 7,890,163 | B2 | 2/2011 | Belalcazar |
| 7,890,166 | B2 | 2/2011 | Heruth et al. |
| 7,890,176 | B2 | 2/2011 | Jaax et al. |
| 7,890,182 | B2 | 2/2011 | Parramon et al. |
| 7,890,185 | B2 | 2/2011 | Cohen et al. |
| 7,894,907 | B2 | 2/2011 | Cowan et al. |
| 7,899,542 | B2 | 3/2011 | Cowan et al. |
| 7,914,452 | B2 | 3/2011 | Hartley et al. |
| 7,933,654 | B2 | 4/2011 | Merfeld et al. |
| 7,937,145 | B2 | 5/2011 | Dobak |
| 7,957,797 | B2 | 6/2011 | Bourget et al. |
| 7,957,809 | B2 | 6/2011 | Bourget et al. |
| 7,979,133 | B2 | 7/2011 | Feler et al. |
| 7,996,055 | B2 | 8/2011 | Hauck et al. |
| 8,000,794 | B2 | 8/2011 | Lozano |
| 8,010,198 | B2 | 8/2011 | Libbus et al. |
| 8,010,203 | B2 | 8/2011 | DeMulling et al. |
| 8,016,776 | B2 | 9/2011 | Bourget et al. |
| 8,019,423 | B2 | 9/2011 | Possover |
| 8,027,718 | B2 | 9/2011 | Spinner et al. |
| 8,046,075 | B2 | 10/2011 | Rezai |
| 8,060,208 | B2 | 11/2011 | Kilgore et al. |
| 8,082,039 | B2 | 12/2011 | Kim et al. |
| 8,086,318 | B2 | 12/2011 | Strother et al. |
| 8,128,600 | B2 | 3/2012 | Gill |
| 8,131,357 | B2 | 3/2012 | Bradley et al. |
| 8,150,521 | B2 | 4/2012 | Crowley et al. |
| 8,150,531 | B2 | 4/2012 | Skelton |
| 8,170,658 | B2 | 5/2012 | Dacey et al. |
| 8,170,675 | B2 | 5/2012 | Alataris et al. |
| 8,180,445 | B1 | 5/2012 | Moffitt |
| 8,197,494 | B2 | 6/2012 | Jaggi et al. |
| 8,204,607 | B2 | 6/2012 | Rooney et al. |
| 8,209,021 | B2 | 6/2012 | Alataris et al. |
| 8,209,028 | B2 | 6/2012 | Skelton et al. |
| 8,214,047 | B2 | 7/2012 | Pyles et al. |
| 8,224,453 | B2 | 7/2012 | De Ridder |
| 8,224,459 | B1 | 7/2012 | Pianca et al. |
| 8,255,048 | B2 | 8/2012 | Dal Molin et al. |
| 8,255,057 | B2 | 8/2012 | Fang et al. |
| 8,280,515 | B2 | 10/2012 | Greenspan |

(56) References Cited

U.S. PATENT DOCUMENTS

| | | | |
|---|---|---|---|
| 8,301,241 B2 | 10/2012 | Ternes et al. |
| 8,340,775 B1 | 12/2012 | Cullen et al. |
| 8,355,791 B2 | 1/2013 | Moffitt |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,364,271 B2 | 1/2013 | De Ridder |
| 8,364,273 B2 | 1/2013 | De Ridder |
| 8,380,318 B2 | 2/2013 | Kishawi et al. |
| 8,396,559 B2 | 3/2013 | Alataris et al. |
| 8,412,338 B2 | 4/2013 | Faltys |
| 8,423,147 B2 | 4/2013 | Alataris et al. |
| 8,428,735 B2 | 4/2013 | Littlewood et al. |
| 8,428,748 B2 | 4/2013 | Alataris et al. |
| 8,467,875 B2 | 6/2013 | Bennett et al. |
| 8,483,830 B2 | 7/2013 | Tweden |
| 8,509,905 B2 | 8/2013 | Alataris et al. |
| 8,509,906 B2 | 8/2013 | Walker et al. |
| 8,554,326 B2 | 10/2013 | Alataris et al. |
| 8,569,935 B1 | 10/2013 | Kosierkiewicz |
| 8,577,458 B1 | 11/2013 | Libbus et al. |
| 8,612,018 B2 | 12/2013 | Gillbe |
| 8,649,874 B2 | 2/2014 | Alataris et al. |
| 8,666,506 B2 | 3/2014 | King |
| 8,676,331 B2 | 3/2014 | Parker |
| 8,688,212 B2 | 4/2014 | Libbus et al. |
| 8,691,877 B2 | 4/2014 | Yun et al. |
| 8,712,533 B2 | 4/2014 | Alataris et al. |
| 8,712,534 B2 | 4/2014 | Wei |
| 8,718,782 B2 | 5/2014 | Alataris et al. |
| 8,751,009 B2 | 6/2014 | Wacnik |
| 8,768,469 B2 | 7/2014 | Tweden et al. |
| 8,805,512 B1 | 8/2014 | Greiner et al. |
| 8,825,164 B2 | 9/2014 | Tweden et al. |
| 8,825,166 B2 | 9/2014 | John |
| 8,886,326 B2 | 11/2014 | Alataris et al. |
| 8,886,328 B2 | 11/2014 | Alataris et al. |
| 8,892,209 B2 | 11/2014 | Alataris et al. |
| 8,918,172 B2 | 12/2014 | Moffitt et al. |
| 8,918,190 B2 | 12/2014 | Libbus et al. |
| 8,918,191 B2 | 12/2014 | Libbus et al. |
| 8,923,964 B2 | 12/2014 | Libbus et al. |
| 8,923,990 B2 | 12/2014 | Libbus et al. |
| 8,965,521 B2 | 2/2015 | Birkholz et al. |
| 8,996,125 B2 | 3/2015 | Greiner et al. |
| 9,002,457 B2 | 4/2015 | Hamann et al. |
| 9,002,459 B2 | 4/2015 | Lee et al. |
| 9,026,214 B2 | 5/2015 | Ternes et al. |
| 9,026,215 B2 | 5/2015 | Rossing |
| 9,026,226 B2 | 5/2015 | Gerber et al. |
| 9,067,076 B2 | 6/2015 | Nolan et al. |
| 9,101,770 B2 | 8/2015 | Arcot-Krishnamurthy et al. |
| 9,126,044 B2 | 9/2015 | Kramer et al. |
| 9,132,272 B2 | 9/2015 | Alves et al. |
| RE45,718 E | 10/2015 | Kilgore |
| 9,180,298 B2 | 11/2015 | Alataris et al. |
| 9,205,258 B2 | 12/2015 | Simon et al. |
| 9,211,410 B2 | 12/2015 | Levine et al. |
| 9,248,293 B2 | 2/2016 | Walker et al. |
| 9,295,840 B1 | 3/2016 | Thacker |
| 9,308,370 B2 | 4/2016 | Lima et al. |
| 9,327,127 B2 | 5/2016 | Alataris et al. |
| 9,370,659 B2 | 6/2016 | Franke et al. |
| 9,381,356 B2 | 7/2016 | Parker |
| 9,403,007 B2 | 8/2016 | Moekelke et al. |
| 9,421,355 B2 | 8/2016 | Colborn |
| 9,440,074 B2 | 9/2016 | Ternes et al. |
| 9,462,398 B2 | 10/2016 | De Ridder |
| 9,480,846 B2 | 11/2016 | Strother |
| 9,533,153 B2 | 1/2017 | Libbus et al. |
| 9,533,164 B2 | 1/2017 | Erickson |
| 9,561,366 B2 | 2/2017 | Wei et al. |
| 9,561,370 B2 | 2/2017 | Rezai |
| 9,572,983 B2 | 2/2017 | Levine et al. |
| 9,694,183 B2 | 7/2017 | Grandhe |
| 9,700,724 B2 | 7/2017 | Liu et al. |
| 9,724,509 B2 | 8/2017 | Su et al. |
| 9,724,511 B2 | 8/2017 | Wei et al. |
| 9,724,513 B2 | 8/2017 | Lane et al. |
| 9,833,614 B1 | 12/2017 | Gliner |
| 9,895,532 B2 | 2/2018 | Kaula et al. |
| 9,895,539 B1 | 2/2018 | Heit et al. |
| 9,913,980 B2 | 3/2018 | Ostroff et al. |
| 9,950,173 B2 | 4/2018 | Doan |
| 9,968,732 B2 | 5/2018 | Drew et al. |
| 10,029,102 B2 | 7/2018 | Doan |
| 10,086,204 B2 | 10/2018 | Grill |
| 10,149,978 B1 | 12/2018 | Park |
| 10,188,856 B1 | 1/2019 | Libbus et al. |
| 10,207,109 B2 | 2/2019 | Zhu et al. |
| 10,220,205 B2 | 3/2019 | Bhadra et al. |
| 10,245,098 B2 * | 4/2019 | Davalos ............ A61B 18/1477 |
| 10,328,264 B2 | 6/2019 | Hamann et al. |
| 10,420,935 B2 | 9/2019 | Illegems |
| 10,463,861 B2 | 11/2019 | Ternes et al. |
| 10,485,975 B2 | 11/2019 | Greiner et al. |
| 10,493,275 B2 | 12/2019 | Alataris |
| 10,537,740 B2 | 1/2020 | Cabunaru |
| 10,561,845 B2 | 2/2020 | Giftakis et al. |
| 10,576,286 B1 | 3/2020 | Park |
| 10,632,300 B2 | 4/2020 | Wagenbach et al. |
| 10,675,468 B2 | 6/2020 | Torgerson |
| 10,898,714 B2 | 1/2021 | Libbus et al. |
| 11,045,649 B2 | 6/2021 | Wei et al. |
| 11,058,875 B1 | 7/2021 | Zinner |
| 11,229,792 B2 | 1/2022 | Alataris |
| 11,235,153 B2 | 2/2022 | Kibler et al. |
| 11,590,352 B2 | 2/2023 | Lee et al. |
| 11,759,638 B2 | 9/2023 | Alataris |
| 11,944,811 B1 | 4/2024 | Pannu et al. |
| 2002/0055779 A1 | 5/2002 | Andrews |
| 2002/0087201 A1 | 7/2002 | Firlik et al. |
| 2002/0128700 A1 | 9/2002 | Cross |
| 2002/0198572 A1 | 12/2002 | Weiner |
| 2003/0018368 A1 | 1/2003 | Ansarinia |
| 2003/0036783 A1 | 2/2003 | Bauhahn |
| 2003/0100931 A1 | 5/2003 | Mullett |
| 2003/0120323 A1 | 6/2003 | Meadows et al. |
| 2003/0135241 A1 | 7/2003 | Leonard et al. |
| 2003/0135248 A1 | 7/2003 | Stypulkowski |
| 2003/0181958 A1 | 9/2003 | Dobak |
| 2003/0199952 A1 | 10/2003 | Stolz et al. |
| 2003/0204221 A1 | 10/2003 | Rodriguez et al. |
| 2003/0208244 A1 | 11/2003 | Stein et al. |
| 2003/0212440 A1 | 11/2003 | Boveja |
| 2004/0015202 A1 | 1/2004 | Chandler et al. |
| 2004/0034394 A1 | 2/2004 | Woods et al. |
| 2004/0039425 A1 | 2/2004 | Greenwood-Van Meerveld |
| 2004/0059395 A1 | 3/2004 | North et al. |
| 2004/0073273 A1 | 4/2004 | Gluckman et al. |
| 2004/0093093 A1 | 5/2004 | Andrews |
| 2004/0116977 A1 | 6/2004 | Finch et al. |
| 2004/0122477 A1 | 6/2004 | Whitehorse |
| 2004/0158119 A1 | 8/2004 | Osorio et al. |
| 2004/0158298 A1 | 8/2004 | Gliner |
| 2004/0158839 A1 | 8/2004 | Gliner et al. |
| 2004/0162590 A1 | 8/2004 | Whitehurst et al. |
| 2004/0167584 A1 | 8/2004 | Carroll et al. |
| 2004/0172085 A1 | 9/2004 | Knudson et al. |
| 2004/0176812 A1 | 9/2004 | Knudson et al. |
| 2004/0186532 A1 | 9/2004 | Tadlock |
| 2004/0186544 A1 | 9/2004 | King |
| 2004/0193228 A1 | 9/2004 | Gerber |
| 2004/0193230 A1 | 9/2004 | Overstreet |
| 2004/0199214 A1 | 10/2004 | Merfeld et al. |
| 2004/0210270 A1 | 10/2004 | Erickson |
| 2004/0210271 A1 | 10/2004 | Campen et al. |
| 2004/0210290 A1 | 10/2004 | Omar-Pasha |
| 2004/0267330 A1 | 12/2004 | Lee et al. |
| 2005/0004417 A1 | 1/2005 | Nelson et al. |
| 2005/0004638 A1 | 1/2005 | Cross |
| 2005/0021104 A1 | 1/2005 | DiLorenzo |
| 2005/0033381 A1 | 2/2005 | Carter et al. |
| 2005/0038489 A1 | 2/2005 | Grill |

(56)                References Cited

U.S. PATENT DOCUMENTS

| | | |
|---|---|---|
| 2005/0049664 A1 | 3/2005 | Harris et al. |
| 2005/0060001 A1 | 3/2005 | Singhal et al. |
| 2005/0070982 A1 | 3/2005 | Heruth et al. |
| 2005/0113877 A1 | 5/2005 | Spinelli et al. |
| 2005/0113878 A1 | 5/2005 | Gerber |
| 2005/0113882 A1 | 5/2005 | Cameron et al. |
| 2005/0119713 A1 | 6/2005 | Whitehurst et al. |
| 2005/0143783 A1 | 6/2005 | Boveja |
| 2005/0143789 A1 | 6/2005 | Whitehurst et al. |
| 2005/0149148 A1 | 7/2005 | King |
| 2005/0153885 A1 | 7/2005 | Yun et al. |
| 2005/0154435 A1 | 7/2005 | Stern et al. |
| 2005/0182453 A1 | 8/2005 | Whitehurst et al. |
| 2005/0187591 A1 | 8/2005 | Carter et al. |
| 2005/0222641 A1 | 10/2005 | Pless |
| 2005/0228451 A1 | 10/2005 | Jaax et al. |
| 2005/0240241 A1 | 10/2005 | Yun et al. |
| 2005/0245978 A1 | 11/2005 | Varrichio et al. |
| 2005/0245987 A1 | 11/2005 | Woods |
| 2005/0246006 A1 | 11/2005 | Daniels |
| 2005/0267545 A1 | 12/2005 | Cory |
| 2005/0278000 A1 | 12/2005 | Strother et al. |
| 2005/0288721 A1 | 12/2005 | Girouard |
| 2006/0004422 A1 | 1/2006 | De Ridder |
| 2006/0009820 A1 | 1/2006 | Royle |
| 2006/0015153 A1 | 1/2006 | Gliner et al. |
| 2006/0025832 A1 | 2/2006 | O'Keeffe et al. |
| 2006/0030895 A1 | 2/2006 | Simon et al. |
| 2006/0030899 A1 | 2/2006 | O'Keeffe et al. |
| 2006/0041285 A1 | 2/2006 | Johnson |
| 2006/0052836 A1 | 3/2006 | Kim et al. |
| 2006/0069415 A1 | 3/2006 | Cameron et al. |
| 2006/0074450 A1 | 4/2006 | Boveja et al. |
| 2006/0079936 A1 | 4/2006 | Boveja et al. |
| 2006/0079937 A1 | 4/2006 | King et al. |
| 2006/0089697 A1 | 4/2006 | Cross et al. |
| 2006/0095088 A1 | 5/2006 | De Ridder |
| 2006/0100671 A1 | 5/2006 | Ridder |
| 2006/0149337 A1 | 7/2006 | John |
| 2006/0161219 A1 | 7/2006 | Mock et al. |
| 2006/0161235 A1 | 7/2006 | King |
| 2006/0167498 A1 | 7/2006 | DiLorenzo |
| 2006/0167512 A1 | 7/2006 | Ross et al. |
| 2006/0167525 A1 | 7/2006 | King |
| 2006/0168805 A1 | 8/2006 | Hegland et al. |
| 2006/0190044 A1 | 8/2006 | Libbus et al. |
| 2006/0190048 A1 | 8/2006 | Gerber |
| 2006/0206166 A1 | 9/2006 | Weiner |
| 2006/0224187 A1 | 10/2006 | Bradley et al. |
| 2006/0229687 A1 | 10/2006 | Goetz et al. |
| 2006/0253174 A1 | 11/2006 | King |
| 2006/0253182 A1 | 11/2006 | King |
| 2006/0271108 A1 | 11/2006 | Libbus et al. |
| 2007/0021801 A1 | 1/2007 | Heruth et al. |
| 2007/0021803 A1 | 1/2007 | Deem et al. |
| 2007/0025608 A1 | 2/2007 | Armstrong |
| 2007/0027486 A1 | 2/2007 | Armstrong |
| 2007/0032827 A1 | 2/2007 | Katims |
| 2007/0039625 A1 | 2/2007 | Heruth et al. |
| 2007/0043400 A1 | 2/2007 | Donders et al. |
| 2007/0049988 A1 | 3/2007 | Carbunaru |
| 2007/0049991 A1 | 3/2007 | Klostermann et al. |
| 2007/0060954 A1 | 3/2007 | Cameron et al. |
| 2007/0060955 A1 | 3/2007 | Strother et al. |
| 2007/0066995 A1 | 3/2007 | Strother et al. |
| 2007/0066997 A1 | 3/2007 | He et al. |
| 2007/0073353 A1 | 3/2007 | Rooney et al. |
| 2007/0073354 A1 | 3/2007 | Knudson et al. |
| 2007/0083240 A1 | 4/2007 | Peterson et al. |
| 2007/0100388 A1 | 5/2007 | Gerber |
| 2007/0106337 A1 | 5/2007 | Errico et al. |
| 2007/0106342 A1 | 5/2007 | Schumann |
| 2007/0142863 A1 | 6/2007 | Bradley |
| 2007/0142874 A1 | 6/2007 | John |
| 2007/0150029 A1 | 6/2007 | Bourget et al. |
| 2007/0156183 A1 | 7/2007 | Rhodes |
| 2007/0156201 A1 | 7/2007 | Rossing |
| 2007/0156207 A1 | 7/2007 | Kothandaraman et al. |
| 2007/0162088 A1 | 7/2007 | Chen et al. |
| 2007/0167992 A1 | 7/2007 | Carley |
| 2007/0179558 A1 | 8/2007 | Gliner et al. |
| 2007/0179559 A1 | 8/2007 | Giftakis et al. |
| 2007/0179579 A1 | 8/2007 | Feler et al. |
| 2007/0191902 A1 | 8/2007 | Errico |
| 2007/0191906 A1 | 8/2007 | Lyer et al. |
| 2007/0203537 A1 | 8/2007 | Goetz et al. |
| 2007/0208381 A1 | 9/2007 | Hill et al. |
| 2007/0208394 A1 | 9/2007 | King et al. |
| 2007/0213789 A1 | 9/2007 | Nolan et al. |
| 2007/0233194 A1 | 10/2007 | Craig |
| 2007/0239226 A1 | 10/2007 | Overstreet |
| 2007/0244522 A1 | 10/2007 | Overstreet |
| 2007/0255118 A1 | 11/2007 | Miesel et al. |
| 2007/0255333 A1 | 11/2007 | Giftakis et al. |
| 2007/0255340 A1 | 11/2007 | Giftakis et al. |
| 2007/0255341 A1 | 11/2007 | Giftakis et al. |
| 2007/0265681 A1 | 11/2007 | Gerber et al. |
| 2007/0282376 A1 | 12/2007 | Shuros et al. |
| 2007/0293893 A1 | 12/2007 | Stolen et al. |
| 2007/0293915 A1 | 12/2007 | Kilgore et al. |
| 2007/0299482 A1 | 12/2007 | Littlewood et al. |
| 2008/0033511 A1 | 2/2008 | Dobak |
| 2008/0046012 A1 | 2/2008 | Covalin et al. |
| 2008/0051839 A1 | 2/2008 | Libbus et al. |
| 2008/0058871 A1 | 3/2008 | Libbus et al. |
| 2008/0058878 A1 | 3/2008 | King |
| 2008/0058888 A1 | 3/2008 | King |
| 2008/0065158 A1 | 3/2008 | Ben-Ezra |
| 2008/0086036 A1 | 4/2008 | Hartley |
| 2008/0103570 A1 | 5/2008 | Gerber |
| 2008/0109045 A1 | 5/2008 | Gross et al. |
| 2008/0140153 A1 | 6/2008 | Burdulis |
| 2008/0154329 A1 | 6/2008 | Pyles et al. |
| 2008/0154333 A1 | 6/2008 | Knudson et al. |
| 2008/0167697 A1 | 7/2008 | Johnson |
| 2008/0183259 A1 | 7/2008 | Bly et al. |
| 2008/0234791 A1 | 9/2008 | Arle et al. |
| 2008/0262411 A1 | 10/2008 | Dobak |
| 2008/0269854 A1 | 10/2008 | Hegland et al. |
| 2008/0281381 A1 | 11/2008 | Gerber et al. |
| 2008/0300449 A1 | 12/2008 | Gerber |
| 2008/0319511 A1 | 12/2008 | Pless |
| 2008/0319514 A1 | 12/2008 | Shi et al. |
| 2009/0018617 A1 | 1/2009 | Skelton et al. |
| 2009/0024186 A1 | 1/2009 | Brockway et al. |
| 2009/0024187 A1 | 1/2009 | Erickson et al. |
| 2009/0024189 A1 | 1/2009 | Lee et al. |
| 2009/0036945 A1 | 2/2009 | Chancellor et al. |
| 2009/0048643 A1 | 2/2009 | Erickson |
| 2009/0054950 A1 | 2/2009 | Stephens |
| 2009/0054962 A1 | 2/2009 | Lefler et al. |
| 2009/0069803 A1 | 3/2009 | Starkebaum |
| 2009/0076565 A1 | 3/2009 | Surwit |
| 2009/0083070 A1 | 3/2009 | Giftakis |
| 2009/0112282 A1 | 4/2009 | Kast et al. |
| 2009/0118777 A1 | 5/2009 | Iki |
| 2009/0125079 A1 | 5/2009 | Armstrong et al. |
| 2009/0132010 A1 | 5/2009 | Kronberg |
| 2009/0132016 A1 | 5/2009 | Putz |
| 2009/0157141 A1 | 6/2009 | Chiao et al. |
| 2009/0157149 A1 | 6/2009 | Wahlgren et al. |
| 2009/0157183 A1 | 6/2009 | Song |
| 2009/0196472 A1 | 8/2009 | Goetz et al. |
| 2009/0198306 A1 | 8/2009 | Goetz et al. |
| 2009/0204173 A1 | 8/2009 | Fang et al. |
| 2009/0204192 A1 | 8/2009 | Carlton et al. |
| 2009/0264789 A1 | 10/2009 | Molnar |
| 2009/0264959 A1 | 10/2009 | Lange |
| 2009/0264973 A1 | 10/2009 | Boling et al. |
| 2009/0281595 A1 | 11/2009 | King et al. |
| 2009/0281596 A1 | 11/2009 | King |
| 2009/0287035 A1 | 11/2009 | Dietrich et al. |
| 2009/0287274 A1 | 11/2009 | De Ridder |
| 2009/0287279 A1 | 11/2009 | Parramon et al. |

(56) References Cited

U.S. PATENT DOCUMENTS

| | | |
|---|---|---|
| 2009/0326611 A1 | 12/2009 | Gillbe |
| 2010/0010567 A1 | 1/2010 | Deem et al. |
| 2010/0016929 A1 | 1/2010 | Prochazka |
| 2010/0023103 A1 | 1/2010 | Elborno |
| 2010/0036454 A1 | 2/2010 | Bennett et al. |
| 2010/0042170 A1 | 2/2010 | Shuros et al. |
| 2010/0042193 A1 | 2/2010 | Slavin |
| 2010/0057178 A1 | 3/2010 | Simon |
| 2010/0094375 A1 | 4/2010 | Donders et al. |
| 2010/0125313 A1 | 5/2010 | Lee et al. |
| 2010/0137938 A1 | 6/2010 | Kishawi et al. |
| 2010/0152817 A1 | 6/2010 | Gillbe |
| 2010/0198298 A1 | 8/2010 | Glukhovsky |
| 2010/0228310 A1 | 9/2010 | Shuros et al. |
| 2010/0241190 A1 | 9/2010 | Kilgore et al. |
| 2010/0249876 A1 | 9/2010 | Giftakis et al. |
| 2010/0256696 A1 | 10/2010 | Schleicher et al. |
| 2010/0262205 A1 | 10/2010 | De Ridder |
| 2010/0274312 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274320 A1 | 10/2010 | Torgerson |
| 2010/0274326 A1 | 10/2010 | Chitre et al. |
| 2010/0318157 A1 | 12/2010 | Giftakis et al. |
| 2010/0324630 A1 | 12/2010 | Lee et al. |
| 2010/0331916 A1 | 12/2010 | Parramon et al. |
| 2010/0331920 A1 | 12/2010 | DiGiore et al. |
| 2011/0009919 A1 | 1/2011 | Carbunaru et al. |
| 2011/0009923 A1 | 1/2011 | Lee |
| 2011/0009927 A1 | 1/2011 | Parker et al. |
| 2011/0022114 A1 | 1/2011 | Navarro |
| 2011/0040291 A1 | 2/2011 | Weissenrieder-Norlin et al. |
| 2011/0040362 A1 | 2/2011 | Godara et al. |
| 2011/0046696 A1 | 2/2011 | Barolat et al. |
| 2011/0071589 A1 | 3/2011 | Starkebaum et al. |
| 2011/0077721 A1 | 3/2011 | Whitehurst et al. |
| 2011/0093042 A1 | 4/2011 | Torgerson et al. |
| 2011/0106208 A1 | 5/2011 | Faltys et al. |
| 2011/0184301 A1 | 7/2011 | Holmstrom et al. |
| 2011/0184486 A1 | 7/2011 | De Ridder |
| 2011/0184488 A1 | 7/2011 | De Ridder |
| 2011/0201977 A1 | 8/2011 | Tass |
| 2011/0276107 A1 | 11/2011 | Simon et al. |
| 2011/0282412 A1 | 11/2011 | Glukhovsky et al. |
| 2011/0301679 A1 | 12/2011 | Rezai |
| 2012/0010680 A1 | 1/2012 | Wei |
| 2012/0083857 A1 | 4/2012 | Bradley |
| 2012/0089200 A1 | 4/2012 | Ranu et al. |
| 2012/0150252 A1 | 6/2012 | Feldman et al. |
| 2012/0239108 A1 | 9/2012 | Foutz et al. |
| 2012/0277833 A1 | 11/2012 | Gerber et al. |
| 2012/0283797 A1 | 11/2012 | De Ridder |
| 2013/0006325 A1 | 1/2013 | Woods et al. |
| 2013/0023951 A1 | 1/2013 | Greenspan |
| 2013/0035740 A1 | 2/2013 | Sharma et al. |
| 2013/0066411 A1 | 3/2013 | Thacker et al. |
| 2013/0079840 A1 | 3/2013 | Su et al. |
| 2013/0079841 A1 | 3/2013 | Su |
| 2013/0096643 A1 | 4/2013 | Fang et al. |
| 2013/0096644 A1 | 4/2013 | Fang et al. |
| 2013/0110196 A1 | 5/2013 | Alataris et al. |
| 2013/0123879 A1 | 5/2013 | Alataris et al. |
| 2013/0138179 A1 | 5/2013 | DeRidder |
| 2013/0172955 A1 | 7/2013 | Alataris et al. |
| 2013/0204173 A1 | 8/2013 | Kelly et al. |
| 2013/0204321 A1 | 8/2013 | Alataris et al. |
| 2013/0204323 A1 | 8/2013 | Thacker et al. |
| 2013/0204324 A1 | 8/2013 | Thacker et al. |
| 2013/0204338 A1 | 8/2013 | Alataris et al. |
| 2013/0211487 A1 | 8/2013 | Fang et al. |
| 2013/0237948 A1 | 9/2013 | Donders |
| 2013/0245714 A1 | 9/2013 | Gupta |
| 2013/0261695 A1 | 10/2013 | Thacker |
| 2013/0261696 A1 | 10/2013 | Thacker |
| 2013/0282078 A1 | 10/2013 | Wacnik |
| 2013/0289659 A1 | 10/2013 | Nelson |
| 2013/0289667 A1 | 10/2013 | Wacnik et al. |
| 2014/0005744 A1 | 1/2014 | Hershey |
| 2014/0031896 A1 | 1/2014 | Alataris et al. |
| 2014/0067016 A1 | 3/2014 | Kaula |
| 2014/0081350 A1 | 3/2014 | Zhu |
| 2014/0142656 A1 | 5/2014 | Alataris et al. |
| 2014/0142657 A1 | 5/2014 | Alataris et al. |
| 2014/0142658 A1 | 5/2014 | Alataris et al. |
| 2014/0142659 A1 | 5/2014 | Alataris et al. |
| 2014/0142673 A1 | 5/2014 | Alataris et al. |
| 2014/0180361 A1 | 6/2014 | Burdick et al. |
| 2014/0316484 A1 | 10/2014 | Edgerton |
| 2014/0343622 A1 | 11/2014 | Alataris et al. |
| 2014/0343623 A1 | 11/2014 | Alves et al. |
| 2014/0379044 A1 | 12/2014 | Walker et al. |
| 2015/0005842 A1* | 1/2015 | Lee ................... A61N 1/36185 |
| | | 607/46 |
| 2015/0012079 A1 | 1/2015 | Goroszeniuk et al. |
| 2015/0018896 A1 | 1/2015 | Alataris et al. |
| 2015/0032181 A1 | 1/2015 | Baynham |
| 2015/0032182 A1 | 1/2015 | Alataris et al. |
| 2015/0032183 A1 | 1/2015 | Alataris et al. |
| 2015/0039049 A1 | 2/2015 | Alataris et al. |
| 2015/0039050 A1 | 2/2015 | Alataris et al. |
| 2015/0045853 A1 | 2/2015 | Alataris et al. |
| 2015/0045854 A1 | 2/2015 | Alataris et al. |
| 2015/0051664 A1 | 2/2015 | Alataris et al. |
| 2015/0051665 A1 | 2/2015 | Hershey et al. |
| 2015/0073510 A1 | 3/2015 | Perryman |
| 2015/0151125 A1 | 6/2015 | Zhu |
| 2015/0165209 A1 | 6/2015 | Grandhe |
| 2015/0202444 A1 | 7/2015 | Franke et al. |
| 2015/0217116 A1 | 8/2015 | Parramon et al. |
| 2015/0321000 A1 | 11/2015 | Rosenbluth |
| 2015/0343220 A1 | 12/2015 | Alataris et al. |
| 2016/0114165 A1 | 4/2016 | Levine |
| 2016/0121119 A1 | 5/2016 | Alataris et al. |
| 2016/0158551 A1 | 6/2016 | Kent |
| 2016/0175586 A1 | 6/2016 | Edgerton et al. |
| 2016/0256689 A1 | 9/2016 | Vallejo et al. |
| 2016/0263376 A1 | 9/2016 | Yoo et al. |
| 2016/0271392 A1 | 9/2016 | Vallejo et al. |
| 2016/0287872 A1 | 10/2016 | Alataris et al. |
| 2016/0287873 A1 | 10/2016 | Alataris et al. |
| 2016/0287874 A1 | 10/2016 | Alataris et al. |
| 2016/0287875 A1 | 10/2016 | Thacker et al. |
| 2016/0287888 A1 | 10/2016 | Alataris et al. |
| 2016/0303374 A1 | 10/2016 | Alataris et al. |
| 2016/0339239 A1 | 11/2016 | Yoo et al. |
| 2017/0001003 A1 | 1/2017 | Pivonka |
| 2017/0036020 A1 | 2/2017 | Harrah |
| 2017/0050021 A1 | 2/2017 | Cosman, Sr. |
| 2017/0087369 A1 | 3/2017 | Bokil |
| 2017/0095669 A1 | 4/2017 | Libbus et al. |
| 2017/0128722 A1 | 5/2017 | Perez |
| 2017/0165485 A1 | 6/2017 | Sullivan et al. |
| 2017/0189686 A1 | 7/2017 | Steinke et al. |
| 2017/0216602 A1 | 8/2017 | Waataja et al. |
| 2017/0239470 A1 | 8/2017 | Wei et al. |
| 2017/0274209 A1 | 9/2017 | Edgerton |
| 2017/0348526 A1 | 12/2017 | Southwell |
| 2018/0123780 A1 | 5/2018 | Ikarashi et al. |
| 2018/0256906 A1 | 9/2018 | Pivonka |
| 2018/0272132 A1 | 9/2018 | Subbaroyan |
| 2018/0345022 A1 | 12/2018 | Steinke et al. |
| 2018/0353758 A1* | 12/2018 | Vallejo ............... A61N 1/36062 |
| 2019/0001135 A1 | 1/2019 | Yoo et al. |
| 2019/0022382 A1 | 1/2019 | Gerasimenko et al. |
| 2019/0060647 A1* | 2/2019 | Su ..................... A61N 1/36175 |
| 2019/0232064 A1 | 8/2019 | Parker |
| 2019/0255331 A1 | 8/2019 | Subbaroyan |
| 2019/0290900 A1 | 9/2019 | Esteller |
| 2019/0321641 A1 | 10/2019 | Baldoni |
| 2019/0329025 A1 | 10/2019 | Moffitt et al. |
| 2020/0139138 A1 | 5/2020 | Sit |
| 2020/0289185 A1* | 9/2020 | Forsyth ................ A61B 18/082 |

(56)                    References Cited

U.S. PATENT DOCUMENTS

FOREIGN PATENT DOCUMENTS

| | | |
|---|---|---|
| CN | 101175530 | 5/2008 |
| DE | 10318071 A1 | 11/2004 |
| EP | 1181947 A2 | 2/2002 |
| EP | 1070518 | 1/2004 |
| EP | 2243510 | 10/2010 |
| EP | 2243511 A2 | 10/2010 |
| EP | 2448633 A1 | 5/2012 |
| EP | 2630984 A1 | 8/2013 |
| EP | 2586491 | 8/2016 |
| GB | 2449546 A | 11/2008 |
| JP | 2002090196 | 3/2002 |
| JP | 2002200179 A | 7/2002 |
| JP | 2007528774 A | 10/2007 |
| JP | 2008500086 A | 1/2008 |
| SU | 1512625 A1 | 10/1989 |
| SU | 1690727 A1 | 11/1991 |
| WO | WO-02065896 A2 | 8/2002 |
| WO | WO-02/085448 | 10/2002 |
| WO | WO-02092165 A1 | 11/2002 |
| WO | WO-03015863 A2 | 2/2003 |
| WO | WO-03066154 A2 | 8/2003 |
| WO | WO-2004007018 A1 | 1/2004 |
| WO | WO-2005087314 | 9/2005 |
| WO | WO-2005115532 A2 | 12/2005 |
| WO | WO-2006007048 | 1/2006 |
| WO | WO-2006057734 A1 | 6/2006 |
| WO | WO-2006063458 | 6/2006 |
| WO | WO-2006084635 A2 | 8/2006 |
| WO | WO-2006119046 A1 | 11/2006 |
| WO | WO-2007035925 A2 | 3/2007 |
| WO | WO-2007082382 A1 | 7/2007 |
| WO | WO-2007103324 A1 | 9/2007 |
| WO | WO-2007117232 A1 | 10/2007 |
| WO | WO-2008039982 A2 | 4/2008 |
| WO | WO-2008045434 A2 | 4/2008 |
| WO | WO-2008106174 A1 | 9/2008 |
| WO | WO-2008121891 A1 | 10/2008 |
| WO | WO-2008140940 | 11/2008 |
| WO | WO-2008142402 A1 | 11/2008 |
| WO | WO-2008153726 A2 | 12/2008 |
| WO | WO-2009018518 A1 | 2/2009 |
| WO | WO-2009061813 A1 | 5/2009 |
| WO | WO-2009097224 A1 | 8/2009 |
| WO | WO-2009129329 A1 | 10/2009 |
| WO | WO-2010111358 A2 | 9/2010 |
| WO | WO-2011014570 A1 | 2/2011 |
| WO | WO-2012154985 | 11/2012 |
| WO | WO-2016154091 A1 | 9/2016 |
| WO | WO-2017044904 | 3/2017 |
| WO | WO-2017146658 | 8/2017 |
| WO | WO-2020236946 | 11/2020 |
| WO | WO-2020236946 A1 * | 11/2020 ......... A61N 1/36196 |
| WO | 2020254794 | 12/2020 |
| WO | WO-2020254794 A1 * | 12/2020 ......... A61N 1/36178 |

OTHER PUBLICATIONS

Congress of Neurological Surgeons—Preliminary Program, Annual Meeting Chicago, Illinois Oct. 7-12, 2006, 84 pages.
De Jongste et al., "Efficacy of Spinal Cord Stimulation as Adjuvant Therapy for Intractable Angina Pectoris: A Prospective, Randomized Clinical Study," JACC, vol. 7, Jun. 1994, 6 pages.
Falowski et al., "Spinal Cord Stimulation: An Update," Neurotherapeutics: The Journal of the American Society for Experimental NeuroTherapeautics, vol. 5, Jan. 2008, 14 pages.
FDA—Premarket Approval, PMA P030017-S002, Boston Scientific Corp., Precision Spinal Cord Stimulation (SCS), Stimulator, Spinal Cord, Totally Implanted for Pain Relief, Model No. SC-1110, https://www.accessdata.fda.gov/scripts/cdrh/cfdocs/cfpma/pma.cfm?id=P030017, Oct. 1, 2004, 3 pages.
FDA—Premarket Approval, PMA P030017-S008, Approval for Artisan 2x8 Paddle Lead, Model SC-8116-XX for the Precision SCS System, https://www.accessdata.fda.gov/scripts/cdrh/cfdocs/cfpma/pma.cfm?id=P030017S008, Aug. 18, 2005, 3 pages.
FDA, Premarket Approval—PMA P840001-S037, Itrel 3 Spinal Cord Stimulation (SCS) for Treatment of Chronic Intractable Pain of hte Trunk and or Limbs, https://www.accessdata.fda.gov/scripts/cdrh/cfdocs/cfpma/pma.cfm?id=P840001S037, Aug. 29, 1995, 3 pages.
Mannheimer et al., "Electrical Stimulation Versus Coronary Artery Bypass Surgery in Severe Angina Pectoris—The ESBY Study," American Heart Association, Inc., 1998, 7 pages.
Manuscript of Eddicks et al., "Thoracic Spinal Cord Stimulation Improves Functional Status and Relieves Symptoms in Patients with Refactory Angina Pectoris: The First Placebo-Controlled Randomized Study," Heart Online First, Jan. 19, 2007, 19 pages.
Medtronic—ITREL 3 Neurostimulator 7425 Neurostimulator, Implant Manual, https://www.neuromodulation.ch/sites/default/files/pictures/itrel3_implant_manual.pdf, 1995, 20 pages.
Medtronic—Itrel EZ Model 7437A Patient Programmer, User Manual, https://fcc.gov/oet/ea/fccid, 2001, 154 pages.
Medtronic—Neuromodulation Product Performance, https://www.medtronic.com/content/dam/medtronic-com/products/product-performance/ppr-reports/product-performance-report-2009.pdf, 2009, 61 pages.
Medtronic—Product Performance Report, https://www.medtronic.com/content/dam/medtronic- com/products/product-performance/ppr-reports/product-performance-report-2010.pdf, 2010, 86 pages.
Medtronic—Spinal Cord Stimulation, Patient Management Guidelines for Clinicians, https://web.archive/org/web/20060522070227/http://medtronic.com/neuro/paintherapies/pain_treatment_ladder/library.html, 1999, 19 pages.
Medtronic—Synergy EZ Model 7435 Patient Programmer, User Manual, https://www.fcc.gov/oet/ea/fccid, 1998, 110 pages.
Medtronic—Synergy, Synergy Versitrel 7427 7427V, Dual-Program Neurostimulators for Spinal Cord Stimulation (SCS), http://www.neuromodulation.ch/sites/default/files/pictures/synergy_implant_manual.pdf, 2003, 96 pages.
Medtronic Activa Parkinson's Control Therapy, Summary of Safety and Effectiveness Data for a Supplemental Premarket Approval Application, PMA P960009/S7, https://www.accessdata.fda.gov/cdrh_docs/pdf/p960009S007b.pdf, Aug. 29, 1995, 30 pages.
Merrill et al., "Electrical Stimulation of Excitable Tissue: Design of Efficacious and Safe Protocols," Journal of Neuroscience Methods, 2005, 28 pages.
New Release, "Boston Scientific Announces Launch of New Precision Plus Spinal Cord Stimulation System—Hardware and software innovations offer new benefits to physicians and patients," PRNewswire-First Call, https://news.bostonscientific.com/news-releases?item=58980, 2 pages.
Shaw et al., "1200Hz Sub-Threshold Epidural Stimulation for Pain Control," Shepherd Center, Interventional Pain Management Physician, Shephard Center, Atlanta, GA., 1 page.
Summary of Safety and Effectiveness, PMA P030017, Precision Spinal Cord Stimulator (SCS) System, https://www.accessdata.fda.gov/cdrh_docs/pdf3/P030017B.pdf, 2004, 18 pages.
Wolter et al., "Effects of Sub-perception threshold spinal cord stimulation in neuropathic pain: A randomized controlled double-blind crossover study," European Journal of Pain, 2012, 8 pages.
"EQ-5D-3L, About," available at https://euroqol.org/eq-5dinstruments/eq-5d-3l-about/ Mar. 31, 2022, 3 pages.
"WaveWriter Alpha Spinal Cord Stimulator System wins Best Overall Medical Device Solution Award," 222 Shares, May 24, 2021, 2 pages.
Abejon et al., "Effects of Movement and Postural Positions in Spinal Cord Stimulation in the New Rechargeable Systems," Pain Physician, 2014, 8 pages.
Bendel, Markus, "New Developments in Spinal Stimulation for Pain Management," Mayo Clinic,https://connect.mayoclinic.org/blog/adult-pain-medicine/newsfeed-post/new-developments-in-spinal-stimulation/ , Nov. 2018, 13 pages.
Boston Scientific, "Boston Scientific Launches WaveWriter Alpha™ Spinal Cord Stimulator Systems in U.S.," Jan. 14, 2021, 3 pages.
Boston Scientific, "Precision™ Spinal Cord Stimulator System Clinician Manual," 9108273-04, 2017, 74 pages.

(56)             References Cited

OTHER PUBLICATIONS

Diedrichs et al., "Symptomatic Relief Precedes Improvement of Myocardial Blood Flow in Patients Under Spinal Cord Stimulation," Current Controlled Trials in Cardiovascular Medicine, 2005, 7 pages.

FDA Summary of Safety and Effectiveness Data, PMA P130022, Senza Spinal Cord Stimulation (SCS) System, 56 pages.

Foletti et al., "Neurostimulation technology for the treatment of chronic pain: a focus on spinal cord stimulation," Future Drugs Ltd, 2007, 14 pages.

Holsheimer et al., "Spinal Geometry and Paresthesia Coverage in Spinal Cord Stimulation," International Neuromodulation Society, 1998, 8 pages.

J.P. Morgan, "Nevro—Quarterly Results In-line with Preannouncement; Hiring in Focus for 2H18," North America Equity Research, Aug. 2, 2018, 8 pages.

Kathuroju et al., "Effect of Low Frequency Pulsed DC on Human Skin in Vivo: Resistance Studies in Reverse Iontophoresis," 104 Sensors & Transducers Journal 47-57 , 2009, 17 pages.

Kloth, Luther C., "Electrical Stimulation Technologies for Wound Healing," Wound Healthing Society, 2014, 11 pages.

Kumar et al., "The use of spinal cord stimulation in pain management," Pain Management, 2012, 11 pages.

Kumar, Krishna, "Neuromodulation and Immortality," Neuromodulation, 2014, 3 pages.

Lee et al., "Predicted Effects of Pulse Width Programming in Spinal Cord Stimulation: A Mathematical Modeling Study," Medical & Biological Engineering & Computing, 2011, 10 pages.

Mills et al., Nevro, "Initation of Coverage: Compelling growth engine with plenty of fuel in the tank; initiate at BUY, $120 target," Canaccord Genuity, Mar. 23, 2017, 57 pages.

Mironer et al., "Pain Tolernace Threshold: A Pilot Study of an Objective Measurement of Spinal Cord Stimulator Trial Results," Pain Medicine, vol. 1, No. 2, 2000, 6 pages.

Morgan Stanely Research, "Nevro Corp, Fundamentals are Very Much Intact," Nov. 8, 2016, 12 pages.

Morgan Stanley—Research, "Medical Technology: Disrupting Neuromodulation Abbott & Nevro are the Winners," Feb. 22, 2017, 27 pages.

Nevro Senza Spinal Cord Stimulator (SCS) System—Patient Manual, 2021, 94 pages.

Nevro, News Release: "Neurosurgery Selects the SENZA-RCT 24-Month Outcomes Publication as the Top Pain Paper of the Year" Jun. 15, 2017, 2 pages.

Smits et al., "Spinal cord stimulation induces c-Fos expression in the dorsal horn in rats with neuropathic pain after partial sciatic nerve injury," Neuroscience Letters 450, 2009, 4 pages.

St. Jude Medical, "Eon Mini™ Rechargeable IPG" 2015, 5 pages.

Struijk et al., "Paresthesia Thresholds in Spinal Cord Stimulation: A Comparison of Theoretical Results with Clinical Data," IEEE Transactions on Rehabilitation Engineering, vol. 1, No. 2, Jun. 1993, 8 pages.

Taylor et al., "Spinal cord stimulation in the treatment of refractory angina: systematic review and meta-analysis of randomised controlled trials," BioMed Central—BMC Cardiovascular Disorders, 2009, 13 pages.

Webster's New World Medical Dictionary, pp. 317-318, Wiley Publishing, Inc., 3d edition, 2008, 5 pages.

Wu et al., "Putative Mechanisms Behind Effects of Spinal Cord Stimulation on Vascular Diseases: A Review of Experimental Studies," Autonomic Neuroscience, 2008, 15 pages.

Advanced Bionics—Precision, Physician Implant Manual, Implantable Pulse Generator model SC1100, https://www.fcc.gov/oet/ea/fccid, 2003, 45 pages.

Aronow et al., "Spinal Cord Stimulation for Treatment of Angina Pectoris," Coronary Artery Disease, 2004, 5 pages.

Nevro—Leadership Through Innovation, J. P. Morgan 37th Annual Healthcare Conference, Jan. 24, 2019, 2 pages.

Medtronic—Spinal Cord Stimulation (SCS) Patient Management Guidelines for Clinicians, 1999, 114 pages.

Milligan et al., "Pathological and Protective Roles of Glia in Chronic Pain," Nat Rev Neurosci. 2009, pages.

Vallejo et al., "The Role of Glia and the Immune System in the Development and Maintenance of Neuropathic Pain," Pain Pract. 2010, pages.

De Leo et al., "The Tetrapartite Synapse: Path to CNS centralization and Chronic Pain," Pain. 2006, pages.

U.S. Appl. No. 15/606,869, filed May 26, 2017, Lee.

Mounaïm et al., "New Neurostimulation Strategy and Corresponding Implantable Device to Enhance Bladder Functions," Biomedical Engineering Trends in Electronics, Communications and Software, Chapter 5, 2011, 15 pages.

Thompson et al., "A double blind randomised controlled clinical trial on the effect of transcutaneous spinal electroanalgesia (TSE) on low back pain," European Journal of Pain, vol. 12, Issue 3, Apr. 2008, 6 pages.

"The Need for Mechanism-Based Medicine in Neuromodulation," Neuromodulation: Technology at the Neural Interface, 2012, 7 pages.

Acticare.com website, http://web.archive.org/web/*/acticare.com, Internet Archive Way Back Machine, 2012, 22 pages.

Advanced Neuromodulation Systems, Compustim SCS Systems, Clinical Manual, 1997, 52 pages.

Agnew et al., "Considerations for safety with chronically implanted nerve electrodes," Epilepsia, 31.s2, 1990, 6 pages.

Al-Kaisy et al., "10 KHz High-Frequency Spinal Cord Stimulation for Chronic Axial Low Back Pain in Patients With No History of Spinal Surgery: A Preliminary, Prospective, Open Label and Proof-of-Concept Study," Neuromodulation: Technology at the Neural Interface, 2016, 8 pages.

Al-Kaisy et al., "Sustained Effectiveness of 10kHz High-Frequency Spinal Cord Stimulation for Patients with Chronic, Low Back Pain: 24-month Results of Prospective Multicenter Study," Pain Medicine, 2014, 8 pages.

Al-Kaisy et al., "The Use of 10-Kilohertz Spinal Cord Stimulation in a Cohort of Patients with Chronic Neuropathic Limb Pain Refractory to Medical Management," Neuromodulation Technology at the Neural Interface, 2015, 6 pages.

Al-Kaisy et al., Poster: "High-Frequency Spinal Cord Stimulation at 10 KHz for the Treatment of Chronic Back Pain Patients without Prior Back Surgery," 2013, 1 page.

Al-Kaisy., "The use of 10-kilohertz spinal cord stimulation in a cohort of patients with chronic neuropathic limb pain refactory to medical management," Neuromodulation: Technology at the Neural Interface, 18.1, 2015, 6 pages.

Alo et al., "New Trends in Neuromodulation for the Management of Neuropathic Pain," Neurosurgery, vol. 50, No. 4, Apr. 2002, 15 pages.

Augustinsson et al., "Spinal Cord Stimulation in Cardiovascular Disease," Functional Neurosurgery, vol. 6, No. 1, Jan. 1995, 10 pages.

Bara et al., Poster re: High Frequency Spinal Cord Stimulation for Dominant Back Pain—1 year follow up, 2013, 1 page.

Barolat et al., "Multifactorial Analysis of Epidural Spinal Cord Stimulation," Stereotactic and Functional Neurosurgery, 1991 56: 77-103.

Barolat et al., "Spinal Cord Stimulation for Chronic Pain Management," Seminars in Neurosurgery, vol. 15, Nos. 2/3, 2004, 26 pages.

Barolat et al., "Surgical Management of Pain—Spinal Cord Stimulation: Equipment and Implantation Techniques," Chapter 41, Thieme Medical Publishers, New York, 2002, 11 pages.

Bennett et al., "Spinal Cord Stimulation for Complex regional pain syndrome | [RSD]: a Retrospective Multicenter Experience from 1995 to 1998 of 101 patients." Neuromodulation, vol. 2, No. 3, 1999, 9 pages.

Benyamin et al., "A Case of Spinal Cord Stimulation in Raynaud's Phenomenon: Can Subthreshold Sensory Stimulation Have an Effect?" Pain Physician www.painphysicianjournal.com, 2007, 6 pages.

Bhadra et al., "High Frequency electrical conduction block of the pudendal nerve," Journal of Neural Engineering—Institute of Physics Publishing, 2006, 8 pages.

(56) References Cited

OTHER PUBLICATIONS

Bhadra et al., Stimulation of High-Frequency Sinusoidal Electrical Block of Mammalian Myelinated Axons, J Comput Neurosco, 22:313-326, 2007.

Bhadra MD, Niloy et al., "High-Frequency Electrical Conduction Block of Mammalian Peripheral Motor Nerve," Muscle and Nerve, Dec. 2005, 9 pages.

BionicNavigator Software Guide, Part MP9055261-001, 2004, 58 pages.

Boger et al., "Bladder Voiding by Combined High Frequency Electrical Pudendal Nerve Block and Sacral Root Stimulation," Neurourology and Urodynamics, 27, 2008, 5 pages.

Boston Scientific "Precision™ Spinal Cord Stimulator System Clinician Manual—Directions for Use," Clinician Manual, 2015, 74 pages (pp. I, 9-10).

Boston Scientific, News Release: "New Data Presented at NANS 2014 Demonstrate Long-Term, Low Back Pain Relief with Boston Scientific Precision Spectra™ Spinal Cord Stimulator System," Dec. 12, 2014, 8 pages.

Bowman and McNeal, Response of Single Alpha Motoneurons to High-Frequency Pulse Trains, Appl. Neurophysiol. 49, p. 121-138, 1986, 10 pages.

Broseta et al., "High-Frequency cervical spinal cord stimulation in spasticity and motor disorders," Advances in Stereotactic and Functional Neurosurgery 7. Springer Viennam 1987, 6 pages.

Butt et al., "Histological Findings Using Novel Stimulation Parameters in a Caprine Model," European Journal of Pain Supplements, 2011, 2 pages.

Cahana et al., "Acute Differential Modulation of Synaptic Transmission and Cell Suvival During Exposure to Pulsed and Continuous Radiofrequency Energy," Journal of Pain, vol. 4, No. 4, May 2003, 6 pages.

Cameron et al., "Effects of posture on stimulation parameters in spinal cord stimulation," Neuromodulation: Technology at the Neural Interface 1.4, 1998, 8 pages.

Camilleri et al., "Intra-abdominal vagal blocking (VBLOC therapy): clinical results with a new implantable medical device," Surgery 143.6, 2008, 9 pages.

Clinicaltrials.gov, "Safety and Effectiveness Study of the Precision SCS System Adapted for High-Rate Spinal Cord Stimulation (Accelerate)," https://clinicaltrials.gov/ct2/show/NCT02093793?term=boston+scientific&recr=Open&cond=%22Pain%22&rank=3, Feb. 2015, 3 pages.

Crapanzano et al., "High Frequency Spinal Cord Stimulation for Complex Regional Pain Syndrome: A Case Report," Pain Physician, 2017, 6 pages.

Crosby et al., "Stimulation Parameters Define the Effectiveness of Burst Spinal Cord Stimulation in a Rat Model of Neuropathic Pain," Neuromodulation Technology at the Neural Interface, International Neuromodulation Society, 2014, 8 pages.

Cuellar et al., "Effect of High Frequency Alternating Current on Spinal Afferent Nociceptive Transmission," Neuromodulation: Technology at the Neural Interface, 2012, 10 pages.

De Carolis et al., Poster: "Efficacy of Spinal Cord Stimulation (SCS) in the Treatment of Failed Back Surgery Syndrome (FBSS): a comparative study," 2013, 1 page.

DeRidder et al., "Are Paresthesias necessary for pain suppression in SCS—Burst Stimulation," BRAIN, Brain Research Center Antwerp of Innovative and Interdisciplinary Neuromodulation, 2010, 27 pages.

DeRidder et al., "Burst Spinal Cord Stimulation: Toward Paresthesia-Free Pain Suppression," www.neurosurgery-online.com, vol. 66, Nos. 5, May 2010, 5 pages.

Dorland's Illustrated Medical Dictionary, Twenty-sixth Edition, "Paresthesia," 1981, 4 pages.

Doug Atkins of Medtronic Neurological, "Medtronic Neurostimulation Leads, 510(k) Summary," Submission Prepared: Feb. 27, 2004, 6 pages.

Duyvendak et al., "Spinal Cord Stimulation With a Dual Quadripolar Surgical Lead Placed in General Anesthesia is Effective in Treating Intractable Low Back and Leg Pain," Neuromodulation: Technology at the Neural Interface, vol. 10, No. 2, 2007, 7 pages.

Eddicks et al., "Thoracic Spinal Cord Stimulation Improves Functional Status and Relieves Symptoms in Patients with Refractory Angina Pectoris: The First Placebo-Controlled Randomised Study," Heart Journal, 2007, 6 pages.

Feeling vs. Function Poster, Mager and Associates Consulting, 2009, 1 page.

Geddes, "A Short History of the electrical stimulation of excitable tissue—Including Electrotherapeutic Applications," The Physiologist, vol. 27, No. 1, Feb. 1984, 51 pages.

Grill, Warren et al., "Stimulus Waveforms for Selective Neural Stimulation," IEEE Engineering in Medicine and Biology, Jul./Aug. 1995, pp. 375-385.

Gulve et al., Poster re: "High-Frequency Spinal Cord Stimulation at 10KHz for the Treatment of Chronic Back Pain Patients without Prior Back Surgery,".

Gulve et al., Poster: "10kHz High Frequency Spinal Cord Stimulation: Middlesbrough Experience," 2013, 1 page.

Guo et al., "Design and Implement of a Mini-Instrument for Rehabilitation with Transcutaneous Electrical Nerve Stimulation," School of Medical Instrument and Food Engineering, University of Shanghai for Science and Technology, Shanghai China, Mar. 31, 2007, 5 pages.

Hefferman et al., "Efficacy of Transcutaneous Spinal Electroanalgesia in Acute Postoperative Pain Management," Anesthesiology, 2001, 2 pages.

Higuchi et al., "Exposure of the Dorsal Root Ganglion in Rats to Pulsed Radiofrequency Currents Activates Dorsal Horn Lamina I and II Neurons," Neurosurgery, vol. 50, No. 4, Apr. 2002, 7 pages.

Hilberstadt et al., "The Effect of Transcutaneous Spinal Electroanalgesia upon Chronic Pain: A single case study," Physiotherapy, vol. 86 No. 3, Mar. 2000, 2 pages.

Hopp et al., "Effect of anodal blockade of myelinated fibers on vagal c-fiber afferents," American Journal Physiological Society, Nov. 1980 239(5), 9 pages.

Hoppenstein, Reuben, "Electrical Stimulation of the Ventral and Dorsal Columns of the Spinal Cord for Relief of Chronic Intractable Pain: Preliminary Report," Surgical Neurology, vol. 4, No. 1, Jul. 1975, 9 pages.

House et al., "Safety and Efficacy of the House/3M Cochlear Implant in Profoundly Deaf Adults," Otolaryngologic Clinics of North America, vol. 19, No. 2, May 1986, 12 pages.

Huxely et al., "Excitation and Conduction in Nerve: Quantitative Analysis," Science, Sep. 11, 1964 145: 1154-9.

International Neuromodulation Society 10th World Congress, Neuromodulation: Technology that Improves Patient Care, London, England, May 21-26, 2011, 385 pages.

J.P. Morgan North America Equity Research, "Nevro—Let the Launch Begin: Senza Approved, Raising PT to $54, " www.jpmorganmarkets.com, May 10, 2015, 8 pages.

J.P. Morgan North America Equity Research, "Nevro—Welcome to the Future of Spinal Cord Stimulation Initiating at OW with $34 Price Target," www.jpmorganmarkets.com, Dec. 1, 2014, 39 pages.

Jacques et al., "Development of a New Implantable Bio-Telestimulator," Surg. Neurol., vol. 13, May 1980, 2 pages.

Jain et al., Abstract—"Accelerate: A Prospective Multicenter Trial Evaluating the Use of High-Rate Spinal Cord Stimulation in the Management of Chronic Intractable Pain," The American Academy of Pain Medicine, 2015, 1 page.

Jang et al., "Analysis of Failed Spinal Cord Stimulation Trails in the Treatment of Intractable Chronic Pain," J. Korean Neurosurg Soc 43, 2008, 5 pages.

Jezernik et al., "Electrical Stimulation for the Treatment of Bladder Dysfunction: Current Status and Future Possibilities," Neurological Research, vol. 24, Jul. 2002, 18 pages.

JMP Securities, "Nevro Corp. (NVRO) Initiating Coverage on Nevro Corp. with a Market Outperform Rating—Investment Highlights," Dec. 1, 2014, 42 pages.

Kapural et al., "Comparison of 10-kHz High Frequency and Traditional Low-Frequency Spinal Cord Stimulation for the Treatment

(56)                    References Cited

OTHER PUBLICATIONS of Chronic Back and Leg Pain: 24-Month Results From a Multi-center, Randomized, Controlled Pivotal Trial," Neurosurgery, vol. 79, No. 5, Nov. 2016, 11 pages.
Kapural et al., "Novel 10-Khz High Frequency Therapy (HF10 Therapy) is Superior to Traditional Low-Frequency Spinal Cord Stimulation for Treatment of Chronic Back and Leg Pain," Anesthesiology The Journal of American Society of Anesthesiologists, Inc., 2005, 11 pages.
Kilgore et al. "Nerve Conduction Block Utilizing High-Frequency Alternating Current" Medical & Biology Engineering and Computing, 2004, vol. 42, pp. 394-406.
Kilgore et al. "Reversible Nerve Conduction Block Using Kilohertz Frequency Alternating Current," Neuromodulation Technology at the Neural Interface, International Neuromodulation Society, 2013, 13 pages.
Kreitler et al., "Chapter 15: Implantable Devices and Drug Delivery Systems—The Handbook for Chronic Pain," NOVA Biomedical Books, New York, 2007, 17 pages.
Krista Oakes of Neuromed, Inc., "Implanted Spinal Cord Stimulator Lead 510(k) Summary of Safety and Effectiveness," Submission Prepared Feb. 21, 1996, 3 pages.
Kuechmann et al., Abstract #853: "Could Automatic Position Adaptive Stimulation Be Useful in Spinal Cord Stimulation?" Medtronic, Inc., Minneapolis, MN, European Journal of Pain 13, 2009, 1 page.
Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.
Kumar et al., "The Effects of Spinal Cord Stimulation in Neuropathic Pain Are Sustained: A 24-month Follow-Up of the Prospective Randomized Controlled Multicenter Trial of the Effectiveness of Spinal Cord Stimulation," www.neurosurgery-online.com, vol. 63, No. 4, Oct. 2008, 9 pages.
Lambru et al., "Safety and Efficacy of Cervical 10 KHz Spinal Cord Stimulation in Chronic Refactory Primary Headaches: A Retrospective Case Series," The Journal of Headache and Pain, 2016, 8 pages.
Lempka et al., "Computational Analysis of Kilohertz Frequency Spinal Cord Stimulation for Chronic Pain Management," Anesthesiology, vol. 122, No. 6, Jun. 2015, 15 pages.
Linderoth et al., "Mechanisms of Spinal Cord Stimulation in Neuropathic and Ischemic Pain Syndromes," Neuromodulation, Chapter 25, 2009, 19 pages.
Linderoth et al., "Mechanisms of Spinal Cord Stimulation in Painful Syndromes: Role of Animal Models," Pain Medicine, vol. 7, No. S1, 2006, 13 pages.
Linderoth et al., "Physiology of Spinal Cord Stimulation: Review and Update," Neuromodulation, vol. 2, No. 3, 1999, 15 pages.
Macdonald, Alexander J. R, and Coates, Tim W., "The Discovery of Transcutaneous Spinal Electroanalgesia and Its Relief of Chronic Pain," Physiotherapy, vol. 81. No. 11, Nov. 1995, 9 pages.
Manola et al., "Technical Performance of Percutaneous Leads for Spinal Cord Stimulation: A Modeling Study," International Neuromodulation Society, 2005, 12 pages.
Mavoori et al., "An Autonomous implantable computer for neural recording and stimulation in unrestrained primates," Journal of Neuroscience Methods, 2005, 7 pages.
Mediati, R.D., , "Mechanisms of Spinal Cord Stimulation," Florence, Oct. 2, 2002, 31 pages.
Medtronic—Neurological Division, QuadPlus, Model 3888, Lead Kit for Spinal Cord Stimulation (SCS) Implant Manual, 1996, 33 pages.
Medtronic—Neurological Division, Resume II, Model 3587A, Lead Kit for Spinal Cord Stimulation (SCS) and Peripheral Nerve Stimulation (PNS), Implant Manual, 1996, 32 pages.
Medtronic—Neurological Division, Resume TL, Model 3986, Lead Kit for Spinal Cord Stimulation (SCS) and Peripheral Nerve Stimulation (PNS), Implant Manual, 1996, 27 pages.
Medtronic—Neurostimulation Systems: Expanding the Array of Pain Control Solutions, 1999, 6 pages.

Medtronic commercial leaflet entitled: Surgical Lead Comparison, 1999, 4 pages.
Medtronic, "Medtronic Pain Therapy—Using Neurostimulation for Chronic Pain, Information for Prescribers" 2007, 29 pages.
Medtronic, Pain Therapy Product Guide, Dec. 2008, 31 pages.
Medtronic, Pisces Quad 3487A, Pisces Quad Compact model 3887, Pisces Quad Plus 3888 Lead Kit, Implant Manual, 2008, 16 pages.
Medtronic: Spinal Cord Stimulation Systems, 2013, 4 pages.
Melzack, Ronald et al., "Pain Mechanisms: A New Theory," Science, vol. 150, No. 3699, Nov. 19, 1965, 9 pages.
Merriam Webster's Collegiate Dictionary, Tenth Edition, definition of "Implantable," 1995, 3 pages.
Meyerson et al., Mechanisms of spinal cord stimulation in neuropathic pain, Neurological Research, vol. 22, Apr. 2000, 5 pages.
Miller, Jonathan, "Neurosurgery Survival Guide—A Comprehensive Guide to Neurosurgical Diagnosis and Treatment," http://d3jonline.tripod.com/neurosurgery/, Nov. 14, 2016, 4 pages.
Miller, Jonathan, "Parameters of Spinal Cord Stimulation and Their Role in Electrical Charge Delivery: A Review," Neuromodulation: Technology at the Neural Interface, 2016, 12 pages.
Morgan Stanley Research North America, "Nevro Corp—There's Something Happening Here," Dec. 15, 2014, 12 pages.
Mosby's Medical Dictionary, 8th Edition, "Paresthesia," 2009, 3 pages.
Mueller et al., "The Med-El Sonatati 100 Cochlear Implant: An evaluation of its safety in adults and children," Acta Oto-Laryngologica, vol. 131, No. 5, 2011, 8 pages.
Muller and Hunsperger, "Helvetica Physiologica Acta—Reversible Blockierung der Erregungsleitung im Nerven durch Mittelfrequenz-Daverstrom," Schwabe & Co. Basel, vol. 25, Fasc. 1, 1967, 4 pages.
Munglani, Rajesh, "The Longer Term Effect of Pulsed Radiofrequency for Neuropathic Pain," PAIN 80, 1999, 3 pages.
Nashold et al., "Dorsal col. Stimulation for Control Pain—Preliminary Report on 30 Patients," J. Neurosurg., vol. 36, May 1972, 8 pages.
Nevro—Chronic Pain and Treatments, http://www.nevro.com/English/Patients/Chronic-Pain-and-Treatments/default.aspx 2016, 3 pages.
Nevro—Clinical Evidence www.nevro.com/English/Physicians/Clinical-Evidence/default.aspx, 2016, 2 pages.
Nevro—HF10™ Therapy Fact Sheet, http://www.nevro.com/English/Newsroom/Resources/default.aspx, 2015, 4 pages.
Nevro—Physician Overview www.nevro.com/English/Physicians/Physician-Overview/default.aspx, 2016, 5 pages.
Nevro—Senza System http://www.nevro.com/English/Physicians/Senza-System/default.aspx, 2016, 3 pages.
Nevro HF10 Therapy—New Hope for Chronic Back Pain and Leg Pain Sufferers, http://s21.q4cdn.com/478267292/files/doc_downloads/HF10-Therapy-New-Hope-for-Chronic-Pain.pdf, 2016, 2 pages.
Nevro Senza Patient Manual, Jan. 16, 2015, 53 pages.
Nevro Senza Physician Implant Manual, Jan. 16, 2015, 31 pages.
Nevro website: HF10 Therapy Advantages, www.nevro.com/English/Patients/HF10-Therapy-Advantages/default.aspx, 2016, 3 pages.
Nevro, PMA Approval Letter and Referenced Summary of Safety and Effectiveness Data (SSED) May 8, 2015, 60 pages.
Nevro's presentation of HF10 therapy on Nevro's website, http://www.nevro.com/English/Home/default.aspx, 2016, 2 pages.
News Release Details, "Nevro Corp. Announces Pricing of Initial Public Offering," 2014, 1 page.
NIDCD-NIH 2011, Cochlear Implant Brochure, http://www.nidcd.nih.gov/health/hearing/pages/coch.aspx, Jun. 29, 2012, 2 pages.
North American Neuromodulation Society—14th Annual Meeting, "Neuromodulation: Vision 2010," Dec. 2-5, 2010, 9 pages.
North American Neuromodulation Society—16th Annual Meeting, "From Innovation to Reality Syllabus," Dec. 6-9, 2012, 198 pages.
North American Neuromodulation Society—Celebrating 20 years, 1 8th Annual Meeting Program Book, Dec. 11-14, 2014, 28 pages.
North American Neuromodulation Society, "Today's Vision, Tomorrow's Reality—17th Annual Meeting," Dec. 5-8, 2013, 12 pages.
North American Neuromodulation, "15th Annual Meeting, Our Crystal Anniversary," Dec. 8-11, 2011, 8 pages.

(56)         References Cited

OTHER PUBLICATIONS

North et al., "Failed Back Surgery Syndrome: 5-year Follow-Up after Spinal Cord Stimulator Implantation," Neurosurgery, Official Journal of the Congress of Neurological Surgeons, vol. 28, No. 5, May 1991, 9 pages.

North et al., "Spinal Cord Stimulation for Axial Low Back Pain," SPINE, vol. 30, No. 12, 2005, 7 pages.

North et al., "Spinal Cord Stimulation for Chronic, Intractable Pain: Experience over Two Decades," Neurosurgery, vol. 32, No. 2, Mar. 1993, 12 pages.

North et al., "Spinal Cord Stimulation With Interleaved Pulses: A Randomized, Controlled Trial," vol. 10, No. 4, 2007, 9 pages.

Oakley et al., "A New Spinal Cord Stimulation System Effectively Relieves Chronic, Intractable Pain: A Multicenter Prospective Clinical Study," Neuromodulation: Technology at the Neural Interface, vol. 10, No. 3, 2007, 17 pages.

Oakley, John C., "Spinal Cord Stimulation in Axial Low Back Pain: Solving the Dilemma," Pain Medicine, vol. 7, No. S1, 2006, 6 pages.

Oakley, John C., "Spinal Cord Stimulation Mechanisms of Action," SPINE vol. 27, No. 22, copyright 2002, 10 pages.

OHSIPP Summer Newsletter, The Official Newsletter for the Ohio Society of Interventional Pain Physicians, vol. 1 Ed. 2, Summer 2010, 8 pages.

Paicius et al., "Peripheral Nerve Field Stimulation for the Treatment of Chronic Low Back Pain: Preliminary Results of Long-Term Follow-up: A Case Series," Neuromodulation: Technology at the Neural Interface, vol. 10, No. 3, 2007, 12 pages.

Palmer et al., "Transcutaneous electrical nerve stimulation and transcutaneous spinal electroanalgesia: A preliminary efficacy and mechanisms-based investigation," Physiotherapy, 95, 2009, 7 pages.

Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.

Prausnitz et al., "The Effects of Electric Current Applied to Skin: A Review for Transdermal Drug Delivery," Advanced Drug Delivery Reviews 18, 1996, 31 pages.

Precision—Charging System, Advanced Bionic Corporation, Part 9055259-0001, 2005, 2 pages.

Precision—Physician System Handbook, Advanced Bionic Corporation, Part 9055253-0001, 2005, 92 pages.

Precision—Physician Trail Kit Insert, Advanced Bionic Corporation, Part 9055258-0001, 2005, 2 pages.

Precision Spinal Cord Stimulation—Charging System Insert, Advanced Bionic Corporation, Part 9055074-0001, 2004, 2 pages.

Precision Spinal Cord Stimulation—Patienet Trial Journal, Advanced Bionic Corporation, Part 9055260-0001, 2004, 10 pages.

Precision Spinal Cord Stimulation—Patient System Handbook, Advanced Bionic Corporation, Part 9055072-0001, 2004, 93 pages.

Precision Spinal Cord Stimulation—Physician Implant Manual, Advanced Bionic Corporation, Part 9055100, 2004, 62 pages.

Precision Spinal Cord Stimulation—Physician Implant Manual, Advanced Bionic Corporation, Part 9055255-0001, 2005, 70 pages.

Precision Spinal Cord Stimulation—Physician Lead Manual, Advanced Bionic Corporation, Part No. 9055183-001, May 2004, 31 pages.

Precision Spinal Cord Stimulation—Physician Lead Manual, Advanced Bionic Corporation, Part 9055095, 2004, 62 pages.

Precision Spinal Cord Stimulation—Physician Lead Manual, Advanced Bionic Corporation, Part 9055256-0001, 2005, 56 pages.

Precision Spinal Cord Stimulation—Physician Trail Handbook, Advanced Bionic Corporation, Part 9055254-0001, 2005, 66 pages.

Precision Spinal Cord Stimulation—Physician Trail Kit Model SC-7005, Part 9055066-001, Advanced Bionic Corporation, 2004, 2 pages.

Precision Spinal Cord Stimulation—Remote Control Model SC-5200, Part 9055107-001, 2004, Advanced Bionic Corporation, 2 pages.

Precision Spinal Cord Stimulation—Remote Control Model SC-5210, Advanced Bionic Corporation, Part 9055257-001, 2005, 2 pages.

Precision Spinal Cord Stimulation System—Patient System Handbook, Advanced Bionic Corporation, Part No. 9055184-001, May 2004, 86 pages.

Precision Spinal Cord Stimulation System, Patient Trial Handbook, Part 9055078, 2004, 74 pages.

Pudenz et al., "Development of an Implantable Telestimulator," Proc. 4th Ann. Nat'l Conf. Neuroelectric Soc., Mar. 10-12, 1971, 111-12 ( Wulfsohn, Norman L. and Anthony Sances, Jr. (eds.) 1971, 4 pages.

Pudenz et al., "Neural Stimulation: Clinical and Laboratory Experiences," Surg. Neurol, 39:235-242 (1993).

Rapcan et al., Clinical Study, "High-Frequency—Spinal Cord Stimulation," Indexed and Abstracted in Science Citation Index Expanded and in Journal Citation Reports, 2015, 3 pages.

Reddy et al., "Comparison of Conventional and Kilohertz Frequency Epidural Stimulation in Patients Undergoing Trailing for Spinal Cord Stimulation: Clinical Considerations," World Neurosurgery, www.sciencedirect.com, 6 pages, 2015.

Remedi Pain Relief—ENM (Electronic Nerve Modulation), https://web.archive.org/web/20050906181041/http://www.remediuk.com/trials.htm, 2005, 5 pages.

Robb et al., "Transcutaneous Electrical Nerve Stimulation vs. Transcutaneous Spinal Electroanalgesia for Chronic Pain Associated with Breast Cancer Treatments," Journal of Pain and Symptom Management, vol. 33, No. 4, Apr. 2007, 10 pages.

Royle, John., "Transcutaneous Spinal Electroanalgesia and Chronic Pain," Physiotherapy, vol. 86, No. 5, May 2000, 1 page.

Schulman et al., "Battery Powered Bion Fes Network," Proceedings of the 26th Annual Conference of the IEEE EMBS, San Francisco, CA., Sep. 1-5, 2004, 4 pages.

Science Daily, "Chronic Pain Costs U.S. up to $635 billion, study shows," www.sciencedaily.com/releases/2012/09/120911091100.htm, Sep. 11, 2012, 2 pages.

Senza Spinal Cord Stimulation (SCS) System—P130022, http://www.fda.gov/MedicalDevices/ProductsandMedicalProcedures/DeviceApprovalsandClearances/Recently-ApprovedDevices/ucm449963.htm Oct. 14, 2016, 2 pages.

Sharan et al., "Evolving Patterns of Spinal Cord Stimulation in Patients Implanted for Intractable Low Back and Leg Pain," International Neuromodulation Society, vol. 5, No. 3, 2002, 13 pages.

Shealy et al., "Dorsal col. Electrohypalgesia," Jul. 1969, 8 pages.

Shealy MD, C. Norman et al., "Electrical Inhibition of Pain by Stimulation of the Dorsal cols. Preliminary Clinical Report," Anesthesiaand Analgesia Current Researches, vol. 446, No. 4, Jul.-Aug. 1967,3 pages.

Shelden et al., "Depolarization in the Treatment of Trigeminal Neuralgia," Evaluation of Compression and Electrical Methods Clinical Concept of Neurophysiological Mechanism, 1966, 8 pages.

Shelden et al., "Development and Clinical Capabilities of a New Implantable Biostimulator," The American J. of Surgery, vol. 124, Aug. 1972, 6 pages.

Shelden et al., Electrical Control of Facial Pain, Am. J. of Surgery, vol. 114, Aug. 1967, 4 pages.

Shelden et al., "Electrical stimulation of the nervous system," Surg. Neurol. vol. 4, No. 1, Jul. 1975, 6 pages.

Simpson et al., "A Randomized, Double-Blind, Crossover Study of the Use of Transcutaneous Spinal Electroanalgesia in Patients with Pain from Chronic Critical Limb Ischemia," Journal of Pain and Symptom Management, vol. 28, No. 5, Nov. 2004, 6 pages.

Simpson, BA, "Spinal Cord Stimulation in 60 cases of Intractable Pain." Journal of Neurology, Neurosurgery and Psychiatry, 1991 54 pp. 196-199.

Simpson, BA, "Spinal Cord Stimulation." British Journal of Neurosurgery, Feb. 11, 1997 (1), 5-11, 7 pages.

Sluijter et al., "The Effects of Pulsed Radiofrequency Fields Applied to the Dorsal Root Ganglion—A Preliminary Report," The Pain Clinic, vol. 11, No. 2, 1998, 12 pages.

Smet et al.,., "Successful Treatment of Low Back Pain with a Novel Neuromodulation Device," AZ Nikolaas, 2010, 12 pages.

Smet et al., Poster: "High-Frequency Spinal Cord Stimulation at 10 KHz after Failed Traditional Spinal Cord Stimulation," NANS, 2013, 1 page.

(56) References Cited

OTHER PUBLICATIONS

Solomonow et al., "Control of Muscle Contractile Force through Indirect High-Frequency Stimulation," AM Journal of Physical Medicine, 1983, vol. 62, No. 3, pp. 71-82.

St. Jude Medical, "Eon Mini™ Rechargeable IPG, The smallest, longest lasting IPG for enhanced patient satisfaction," Apr. 29, 2013, 3 pages.

St. Jude Medical, "Individualized Therapy through Diverse Lead Options," 2008, 6 pages.

Stimwave, News Release: Stimwave Receives FDA Approval for High Frequency IDE, http://stimwave.com/newsroom/latest-news, Jun. 9, 2015, 2 pages.

Struijk et al., "Recruitment of Dorsal col. Fibers in Spinal Cord Stimulation: Influence of Collateral Branching," IEEE Transactions on Biomedical Engineering, vol. 39, No. 9, Sep. 1992, 10 pages.

Sweet et al., "Paresthesia-Free High Density Spinal Cord Stimulation for Postlaminectomy Syndrome in a Prescreened Population: A Prospective Case Series," Neuromodulation: Technology at the Neural Interface, 2015, 7 pages.

Swigris et al., "Implantable Spinal Cord Stimulator to Treat the Ischemic Manifestations of Thromboangiitis Obliterans (Buerger's disease)," Journal of Vascular Surgery, vol. 29, No. 5, 1998, 8 pages.

Tan et al., "Intensity Modulation: A Novel Approach to Percept Control in Spinal Cord Stimulation," Neuromodulation Technology at the Neural Interface, International Neuromodulation Society 2015, 6 pages.

Tanner, J.A., "Reversible blocking of nerve conduction by alternating-current excitation," Nature, 1962, Aug. 18 195: 712-3.

Taylor et al., "The Cost Effectiveness of Spinal Cord Stimulation in the Treatment of Pain: A Systematic Review of the Literature," Journal of Pain and Symptom Management, vol. 27, No. 4., Apr. 2001, 9 pages.

Tesfaye et al., "Electrical Spinal Cord Stimulation for Painful Diabetic Peripheral Neuropathy," The Lancet, vol. 348, Dec. 21-28, 1996, 4 pages.

Tiede et al., "Novel Spinal Cord Stimulation Parameters in Patients with Predominate Back Pain," Neuromodulation: Technology at the Neural Interface, 2013, 6 pages.

Tollison et al., "Practical Pain Management Neurostimulation Techniques," Chapter 12, Lippincott Williams and Wilkins, Third Edition, 2002, 13 pages.

Towell et al., "High Frequency non-invasive stimulation over the spine: Effects on mood and mechanical pain tolerance in normal subjects," Behavioral Neurology, vol. 10, 1997, 6 pages.

Urban et al., "Percutaneous epidural stimulation of the spinal cord for relief of pain—Long Term Results," Journal of Neurosurgery, vol. 48, Mar. 1978, 7 pages.

Van Butyen et al., "High Frequency Spinal Cord Stimulation for the Treatment of Chronic Back Pain Patients: Results of a Prospective Multicenter European Clinical Study," Neuromodulation Technology at the Neural Interface, International Neuromodulation Society, 2012, 8 pages.

Van Buyten et al., "Pain Relief for Axial Back Pain Patients," INS Meeting Poster, 2011, 1 page.

Van Den Honert et al. "Generation of Unidirectionally Propagated Action Potentials Nerve by Brief Stimuli" Science, vol. 26, pp. 1311-1312.

Van Den Honert, Mortimer JT, "A Technique for Collision Block of Peripheral Nerve: Frequency Dependence," MP-11 IEEE Trans. Biomed, Eng. 28: 379-382, 1981.

Van Havenbergh et al., "Spinal Cord Stimulation for the Treatment of Chronic Back Pain Patients: 500-Hz vs. 1000-Hz Burst Stimulation," Neuromodulation: Technology at the Neural Interface, International Neuromodulation Society, 2014, 4 pages.

Verrills et al., "Peripheral Nerve Field Stimulation for Chronic Pain: 100 Cases and Review of the Literature," Pain Medicine, 2011, 11 pages.

Verrills et al., "Salvaging Failed Neuromodulation Implants with Nevro High Frequency Spinal Cord System, "NANS Poster, 2013, 1 page.

Von Korff et al., "Assessing Global Pain Severity by Self-Report in Clinical and Health Services Research," SPINE, vol. 25, No. 24, 2000, 12 pages.

Wallace et al., Poster: "Accelerate: A Prospective Multicenter Trial Evaluating the Use of High-Rate Spinal Cord Stimulation in the Management of Chronic Intractable Pain," Boston Scientific Corporation, 2015, 1 page.

Ward et al., "Electrical Stimulation Using Kilohertz-Frequency Alternating Current," Journal of the American Physical Therapy Association, vol. 89, No. 2, Feb. 2009, 12 pages.

Ward et al., "Variation in Motor Theshold with Frequency Using KHz Frequency Alternating Current," Muscle and Nerve, Oct. 2001, 9 pages.

Webster's Third New International Dictionary of the English Language Unabridge, "Paresthesia," 1993, 3 pages.

Weinberg et al., "Increasing the oscillation frequency of strong magnetic fields above 101 kHz significantly raises peripheral nerve excitation thresholds," Medical Physics Letter, May 2012, 6 pages.

Wolter et al., "Continuous Versus Intermittent Spinal Cord Stimulation: An Analysis of Factors Influencing Clinical Efficacy," Neuromodulation: Technology at Neural Interface, www.neuromodulationjournal.com, 2011, 8 pages.

Woo MY, Campbell B. "Asynchronous Firing and Block of Peripheral Nerve Conduction by 20KC Alternating Current," Los Angeles Neuro Society, Jun. 1964, 87-94, 5 pages.

Yearwood et al., "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Congress of Neurological Surgeons 56th Annual Meeting, Oct. 7-12, 2006, 2 pages.

Yearwood et al., "Pulse Width Programming in Spinal Cord Stimulation: A Clinical Study," Pain Physician Journal, Jul./Aug. 2010, 16 pages.

Yearwood et al., Case Reports: "A Prospective Comparison of Spinal Cord Stimulation (SCS) Using Dorsal Column Stimulation (DCS), Intraspinal Nerve Root Stimulation (INRS), and Varying Pulse Width in the Treatment of Chronic Low Back Pain," Presented at the Congress of Neurological Surgeons 56th Annual Meeting, Oct. 7-12, 2006, 7 pages.

Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.

Zhang et al., Changes Across Time in Spike Rate and Spike Amplitude of Auditory Nerve Fibers Stimulated by Electric Pulse Trains, Journal of the Association for Research of Otolaryngology, 2007, 17 pages.

Abejon et al., "Is Impedance a Parameter to be Taken into Account in Spinal Cord Stimulation?" Pain Physician, 2007, 8 pages.

Alo et al., "Factors Affecting Impedance of Percutaneous Leads in Spinal Cord Stimulation," International Neuromodulation Society, vol. 9, No. 2, 2006, 8 pages.

Al-Kaisy et al., "Prospective, Randomized, Sham-Control, Double Blind, Crossover Trial of Subthreshold Spinal Cord Stimulation at Various Kilohertz Frequencies in Subjects Suffering from Failed Back Surgery Syndrome," International Neuromodulation Society, Jan. 2018, 9 pages.

Bronstein et al., "The Rationale Driving the Evolution of Deep Brain Stimulation of Constant-Current Devices," International Neuromodulation Society 2014, 5 pages.

Burton, Charles, "Dorsal Column Stimulation: Optimization of Application," Surgical Neurology, vol. 4, No. 1, Jul. 1975, 10 pages.

Holsheimer—Effectiveness of Spinal Cord Stimulation in the Management of Chronic Pain: Analysis of Technical Drawbacks and Solutions, Neurosurgery, vol. 40, No. 5, May 1997, pp. 990-999.

McCreery et al., "Charge Density and Charge Per Phase as Cofactors in Neural Injury Induced by Electrical Stimulation," IEEE Transactions on Biomedical Engineering, vol. 37, No. 10, Oct. 1990, 6 pages.

McCreery et al., "Damage in Peripheral Nerve from Continuous Electrical Stimulation: Comparison of Two Stimulus Waveforms," Medical and Biological Engineering and Computing, Jan. 1992, 6 pages.

(56)                    References Cited

OTHER PUBLICATIONS

McCreery et al., "Relationship between Stimulus Amplitude, Stimulus Frequency and Neural Damage During Electrical Stimulation of Sciatic Nerve of a Cat," Medical and Biological Engineering and Computing, May 1995, 4 pages.

Nevro—Leadership Through Innovation, J. P. Morgan 36th Annual Healthcare Conference, Jan. 8, 2018, 21 pages.

Renew Neurostimulation System—Clinician's Manual—Advanced Neuromodulation Systems, Life Gets Better, 2000, 77 pages.

Rosenblueth et al., "The Blocking and Deblocking Effects of Alternating Currents on Nerve," Department of Physiology in Harvard Medical School, Nov. 1938, 13 pages.

St. Jude Medical, "Clinician's Manual—Percutaneous Lead Kit, Models 3143, 3146, 3149, 3153, 3156, 3159, 3183, 3186, 3189," 2016, 24 pages.

Thomson et al., "Effects of Rate on Analgesia in Kilohertz Frequency Spinal Cord Stimulation: Results of the PROCO Randomized Controlled Trial," Neuromodulation: Technology at the Neural Interface, 2017, 10 pages.

Wesselink et al., Analysis of Current Density and Related Parameters in Spinal Cord Stimulation, IEEE Transaction on Rehabilitation Engineering vol. 6, No. 2, Jun. 1998, 8 pages.

Siegel et al., "Prospective Randomized Feasibility Study Assessing the Effect of Cyclic Sacral Neuromodulation on Urinary Urge Incontinence in Women," Female Pelvic Med Reconstr Surg. 2018, 5 pages.

Cadish, "Stimulation Latency and Comparison of Cycling Regimens in Women Using Sacral Neuromodulation," Feb. 1, 2016, 4 pages.

Cappaert et al., "Efficacy of a New Charge-Balanced Biphasic Electrical Stimulus in the Isolated Sciatic Nerve and the Hippocampal Slice," International Journal of Neural Systems, vol. 23, No. 1, 2013, 16 pages.

Hofmann et al., "Modified Pulse Shapes for Effective Neural Stimulation," Frontiers in Neuroengineering, Sep. 28, 2011, 10 pages.

International Search Report and Written Opinion for International Patent Application No. PCT/US2022/030933, Applicant: Nevro Corp., mailed Sep. 16, 2022, 15 pages.

Dong et al., "Research on Stimulus Pattern for Inhibition of Detrusor Hyperreflexia," 3rd International Conference on Biomedical Engineering and Informatics, 2010, 4 pages.

Extended European Search Report for European Patent Application No. 22812075.4, Applicant: Nevro Corp., mailed Oct. 10, 2024, 9 pages.

* cited by examiner

Current at each electrode 621-623
during pulses 601a-c

650

651a

651b

651c

Current at each electrode 621-623
during pulses 651a-c

620

621

622

623

601a          601b          601c

MODIFIED HIGH FREQUENCY NEUROMODULATION SIGNALS, AND ASSOCIATED SYSTEMS AND METHODS

CROSS-REFERENCE TO RELATED APPLICATION(S)

The present application claims priority to U.S. Provisional Application No. 63/192,998, filed May 25, 2021, the disclosure of which is incorporated by reference herein in its entirety.

TECHNICAL FIELD

The present technology is directed generally to spinal cord modulation and associated systems and methods for treating patient conditions, including modified high frequency neuromodulation signals and administration patterns.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation ("SCS") have cylindrical leads that include a lead body with a circular cross-sectional shape and one or more conductive rings spaced apart from each other at the distal end of the lead body. The conductive rings operate as individual electrodes and, in many cases, the SCS leads are implanted percutaneously through a needle inserted into the epidural space, with or without the assistance of a stylet. Once implanted, the pulse generator applies electrical pulses to the electrodes, which in turn modify the function of the patient's nervous system, such as by altering the patient's responsiveness to sensory stimuli and/or altering the patient's motor-circuit output.

In the context of treating pain, electrical signals have been applied at low frequencies (e.g., frequencies less than 1.2 kHz) and high frequencies (e.g., frequencies greater than 1.2 kHz). When the electrical pulses are applied at a low frequency (e.g., less than 1.2 kHz), the signals can generate sensations that mask or otherwise alter the patient's sensation of pain. For example, in many cases, patients report a tingling or paresthesia that is perceived as more pleasant and/or less uncomfortable than the underlying pain sensation. While this may be the case for many patients, many other patients may report less beneficial effects and/or results. When the electrical pulses are applied at a high frequency (e.g., greater than 1.2 kHz), the signals generally do not generate paresthesia and produce generally effective pain relief. However, the onset of pain relief in response to high frequency signals is often delayed, leading to a period of several hours to several days during which the patient is still suffering from pain. Accordingly, there remains a need for improved techniques and systems for addressing patient pain.

DETAILED DESCRIPTION

Figure 1A:
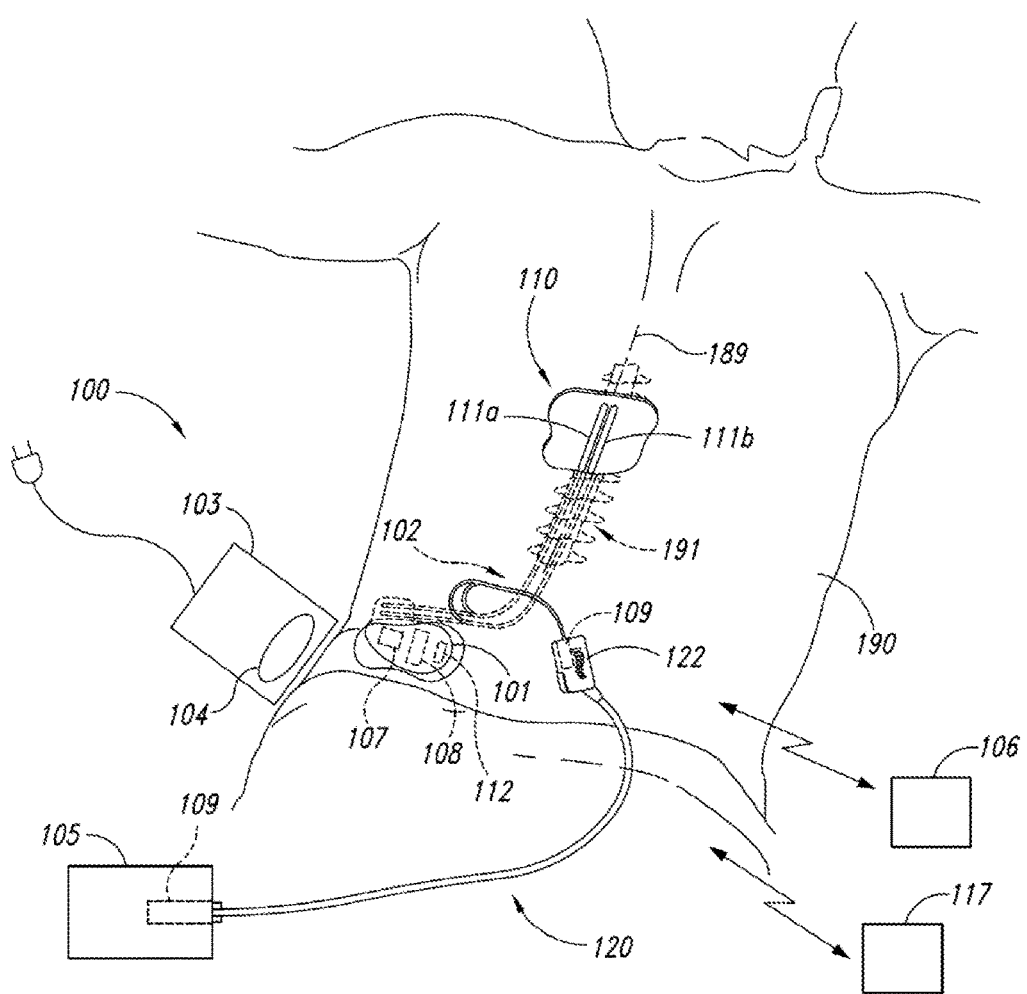
FIG. 1A is a partially schematic illustration of an implantable spinal cord modulation system positioned at a patient's spine to deliver therapeutic signals in accordance with some embodiments of the present technology.
Figure 1B:
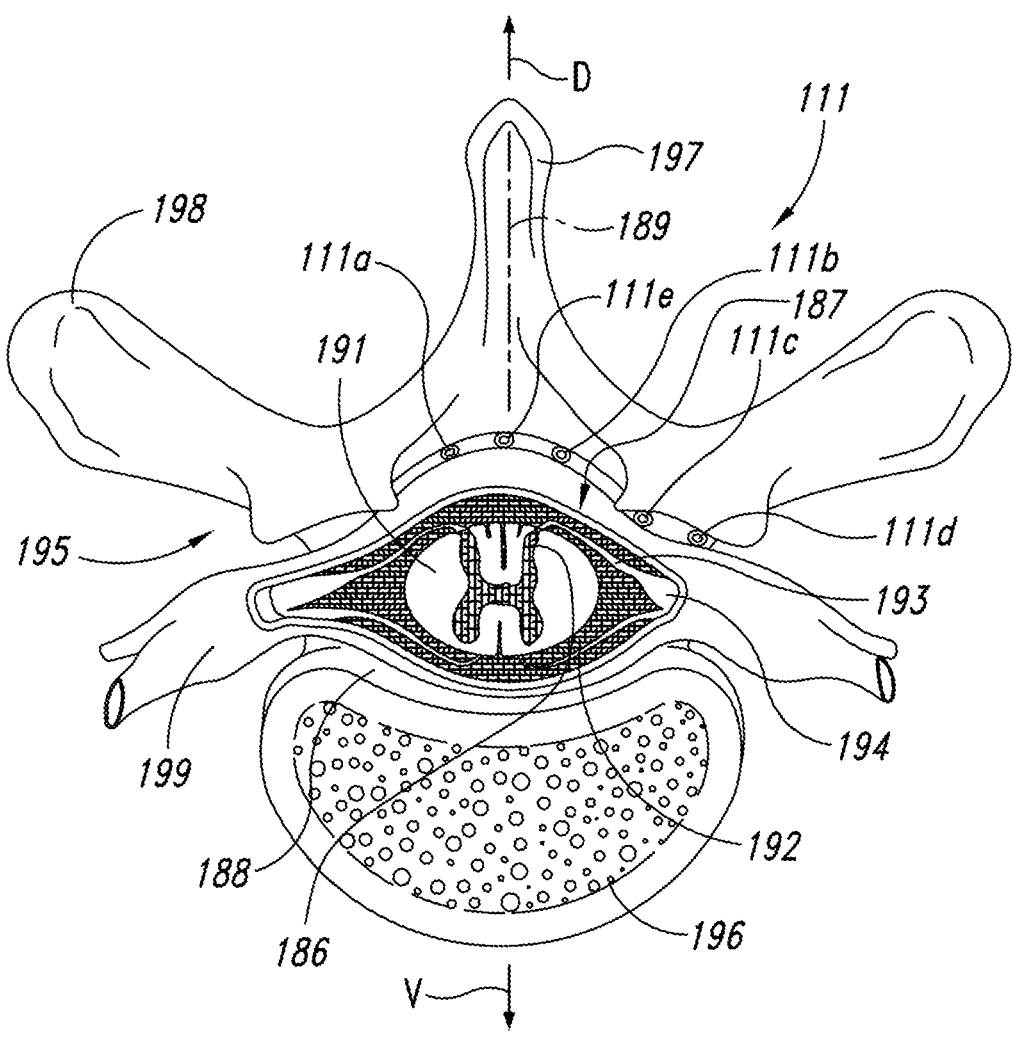
FIG. 1B is a partially schematic, cross-sectional illustration of a patient's spine, illustrating representative locations for implanted lead bodies in accordance with some embodiments of the present technology.
Figure 2:
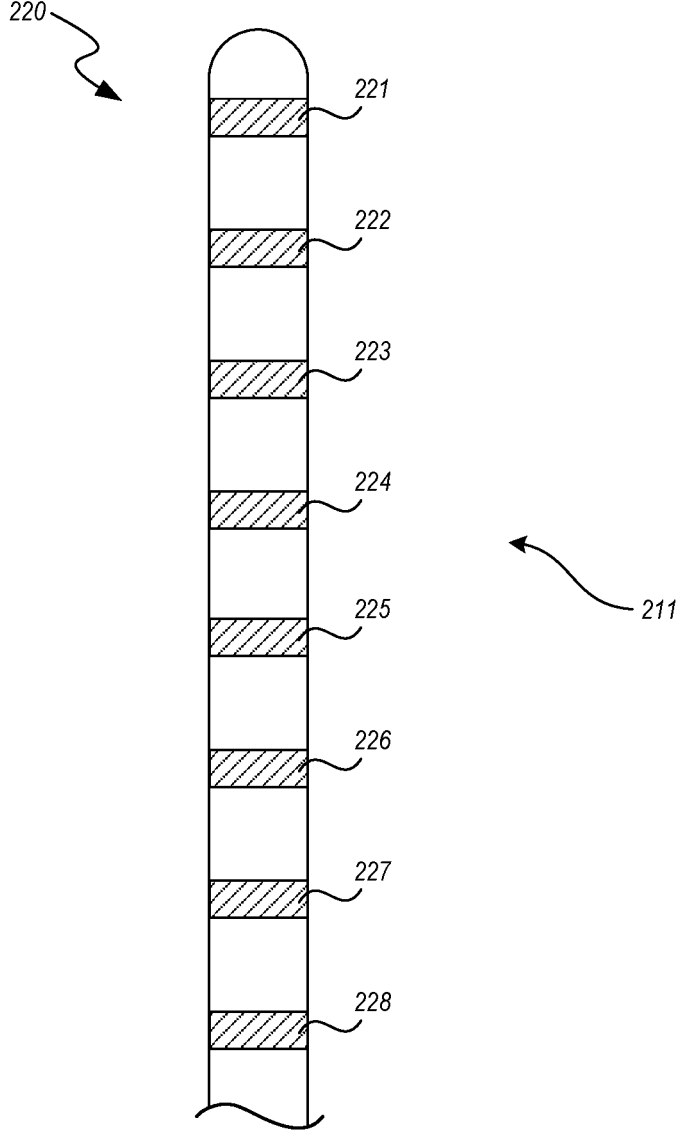
FIG. 2 is a schematic illustration of a representative lead body suitable for providing modulation to a patient in accordance with several embodiments of the present technology.
Figure 6A:
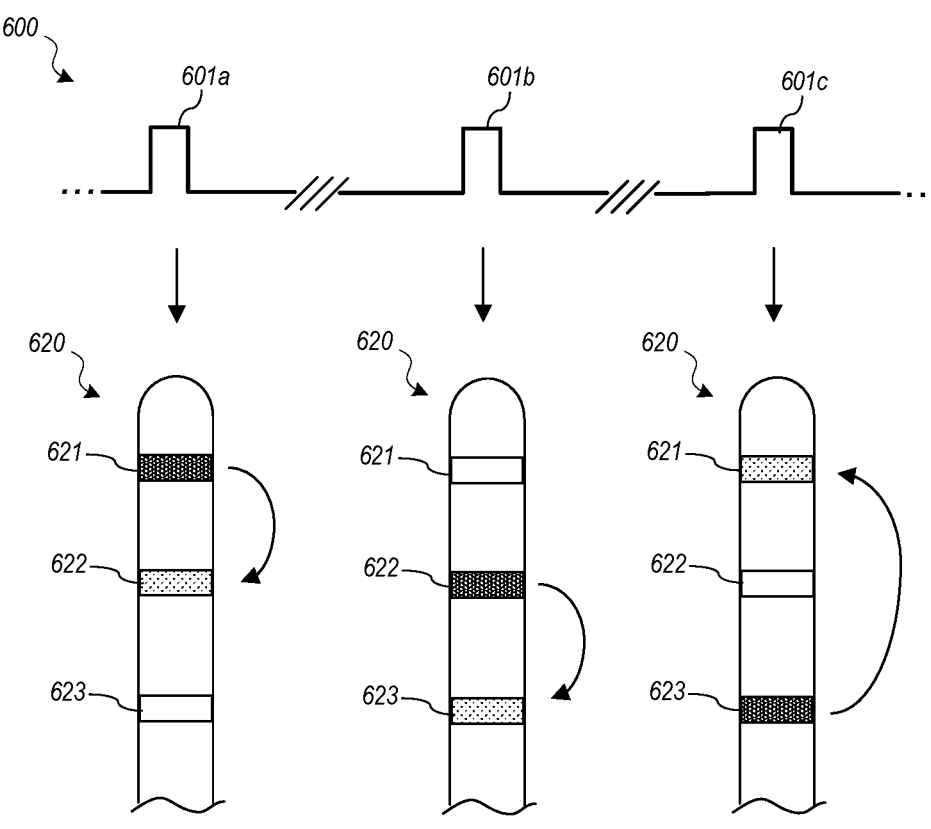
FIGS. 6A-6C are partially schematic illustrations of a pattern for administering an electrical therapy signal in accordance with embodiments of the present technology.
Figure 6B:
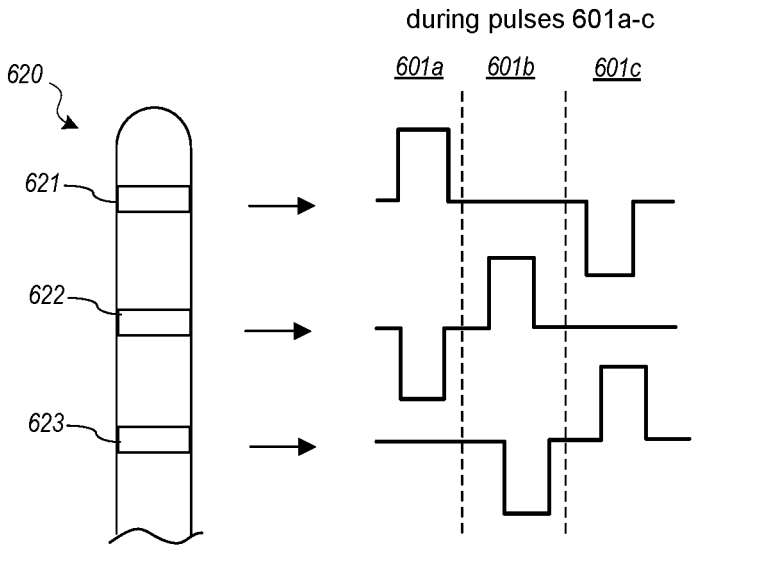
Figure 6C:
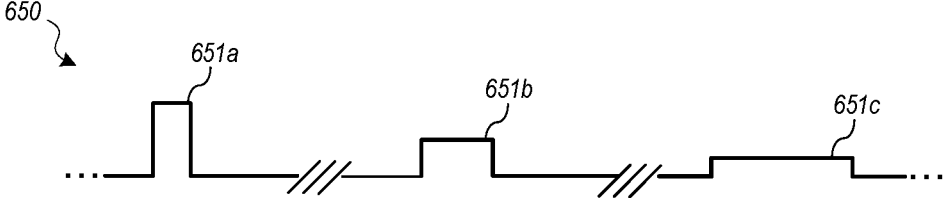
Figure 6C:
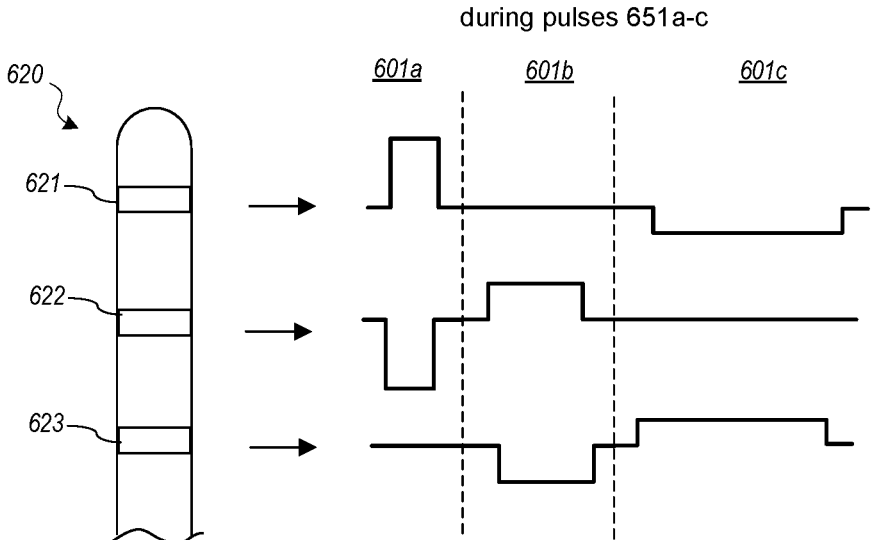
Figure 7:
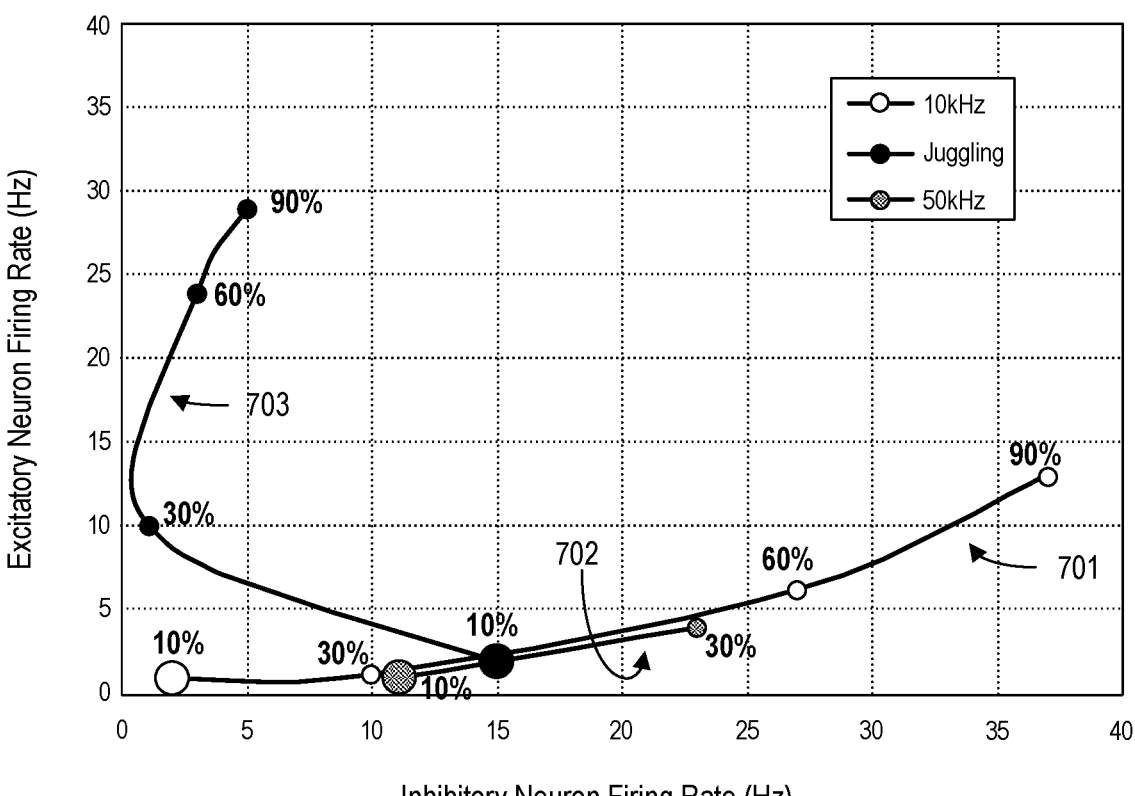
FIG. 7 is a line graph illustrating the relative firing rate of excitatory neurons versus inhibitory neurons in response to select high frequency electrical therapy signals.
Figure 8A:
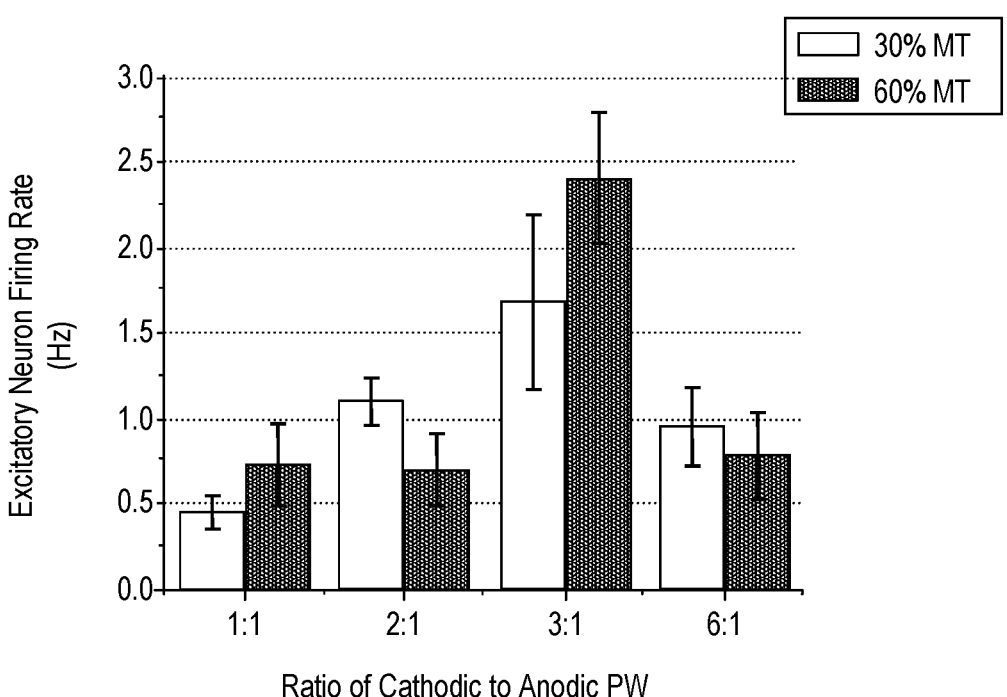
FIGS. 8A and 8B are bar graphs illustrating the relative firing rate of excitatory and inhibitory neurons in response to high frequency electrical therapy signals having asymmetric bi-phasic pulses.
Figure 8B:
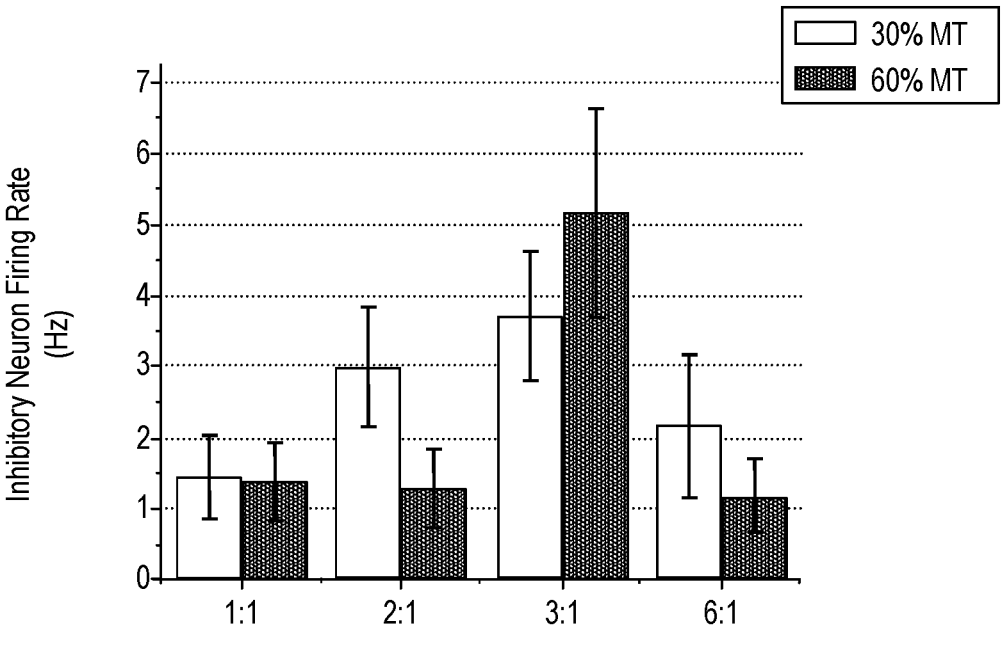
Figure 8C:
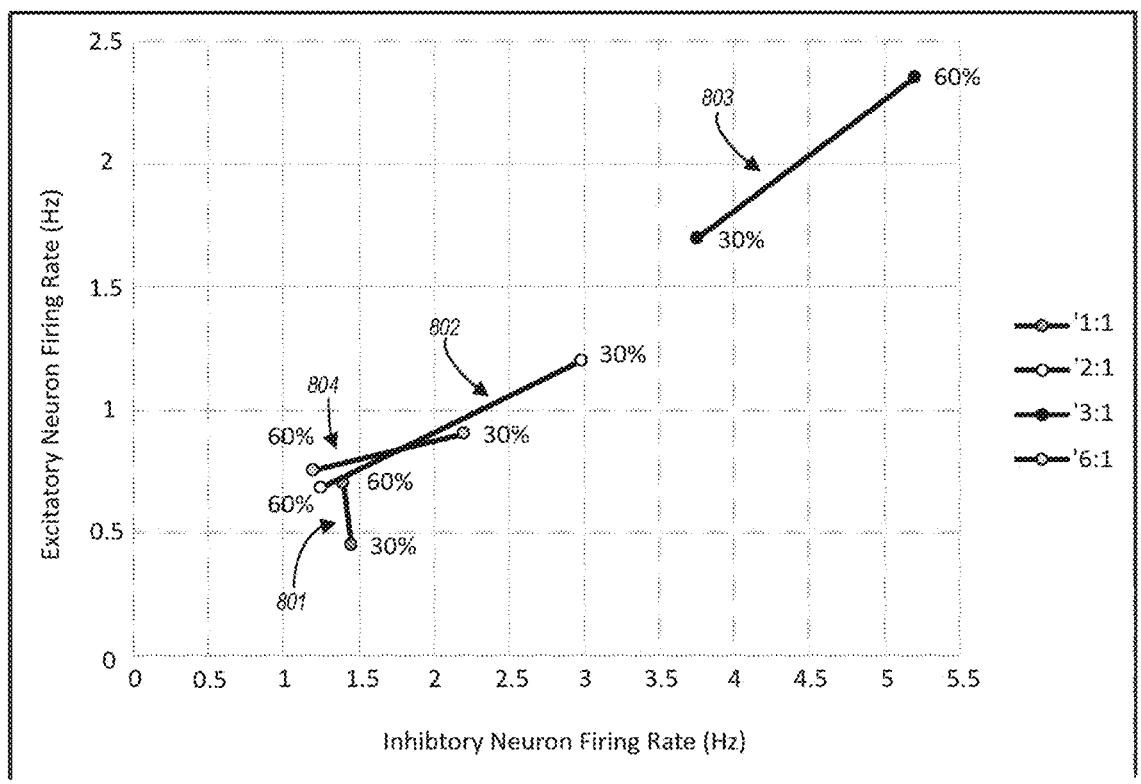
FIG. 8C is a line graph illustrating the relative firing rate of excitatory and inhibitory neurons in response to high frequency electrical therapy signals having asymmetric bi-phasic pulses.
Figure 9:
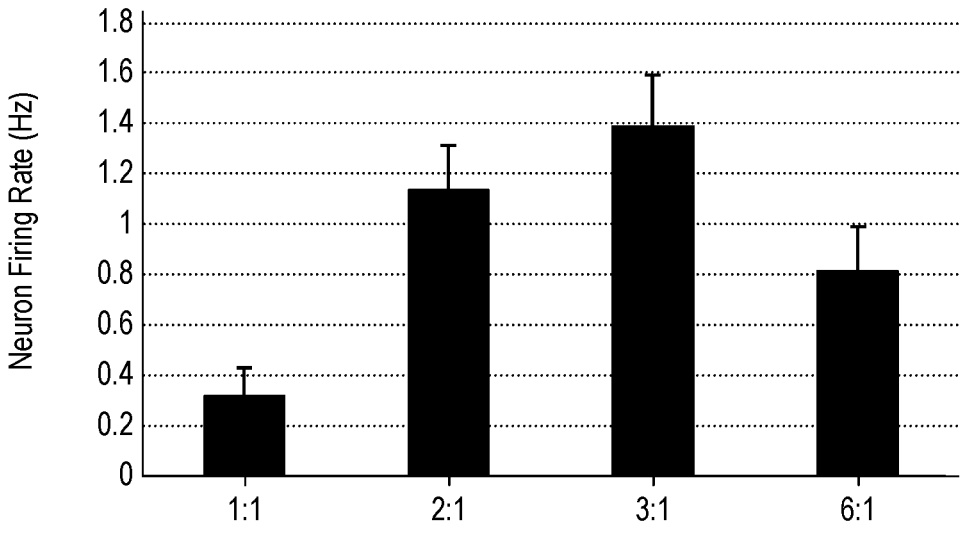
FIG. 9 is a bar graph illustrating the relative firing rate of neurons in response to high frequency electrical therapy signals having relatively long interphase intervals.
Figure 10:
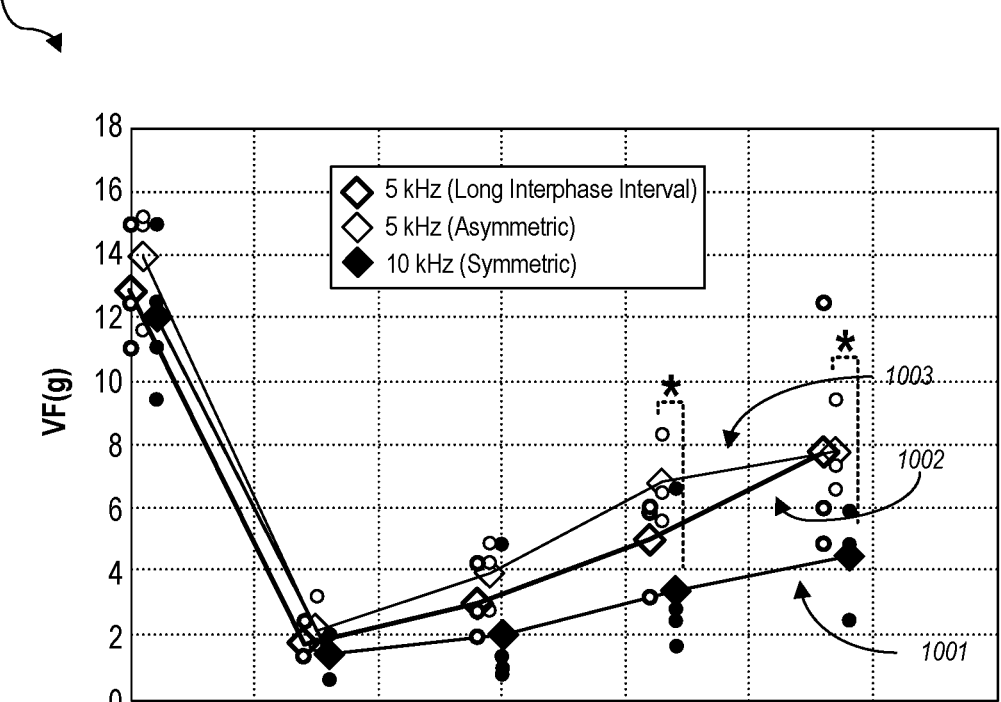
FIG. 10 is a graph comparing pain relief achieved using various high frequency electrical therapy signals described herein.
Figure 11:
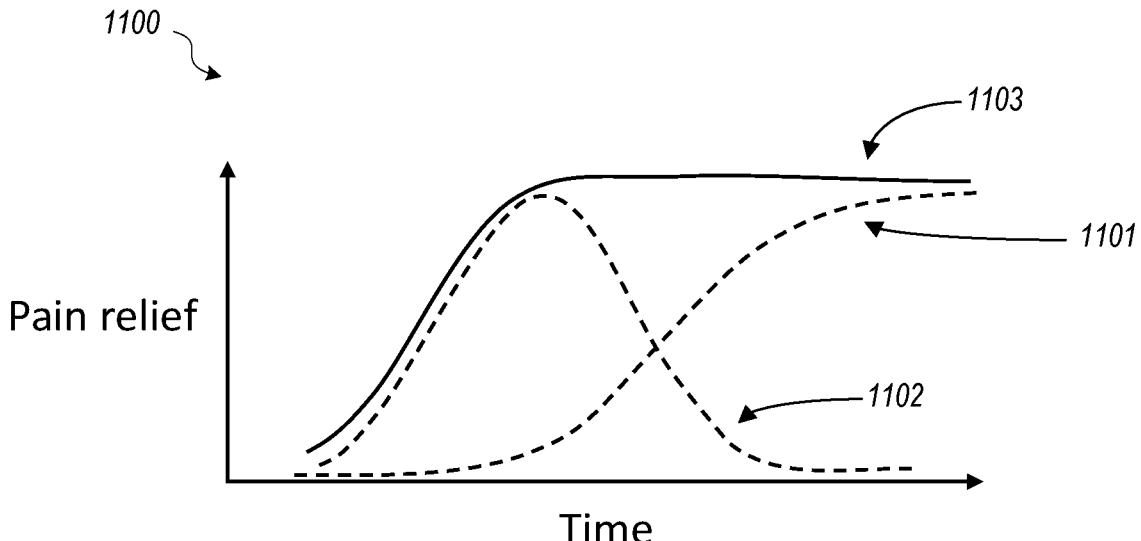
FIG. 11 is a graph demonstrating the expected pain relief over time of existing and modified high frequency electrical therapy signals.

This detailed description includes the following headers and sections, which are provided for convenience only and do not interpret the scope or meaning of the claimed present technology:

Definitions of selected terms are provided under Heading 1.0 ("Definitions");

General aspects of the present technology are described below under Heading 2.0 ("Overview of Present Technology");

Representative treatment systems and their characteristics are described under Heading 3.0 ("System Characteristics") with reference to FIGS. 1A, 1B and 2;

Representative electrical therapy signals for use in treating patients are described under Heading 4.0 ("Representative Therapy Signals") with reference to FIGS. 3A-5;

Representative patterns for administering electrical therapy signals for use in treating patients are described under Heading 5.0 ("Representative Patterns of Administration") with reference to FIGS. 6A-6C;

Potential effects of the representative therapy signals and patterns of administration are described under Heading 6.0 ("Selectivity of Modified High Frequency Electrical Therapy Signals") with reference to FIGS. 7-9;

Therapies combining existing high frequency signals with modified high frequency signals are described under Heading 7.0 ("Combined Therapy") with reference to FIGS. 10 and 11;

Additional expected benefits of certain embodiments of the present technology are described under Heading 8.0 ("Additional Expected Benefits Associated with Certain Embodiments"); and Representative examples are described under Heading 9.0 ("Representative Examples").

1.0 Definitions

Unless otherwise stated, the terms "generally," "about," and "approximately" refer to values within 10% of a stated value. For example, the use of the term "about 100" refers to a range of 90 to 110, inclusive. In instances where relative terminology is used in reference to something that does not include a numerical value, the terms are given their ordinary meaning to one skilled in the art.

As used herein, and unless otherwise noted, the terms "modulate," "modulation," "stimulate," and "stimulation" refer generally to signals that have an inhibitory, excitatory, and/or other effect on a target neural population. Accordingly, a spinal cord "stimulator" can have an inhibitory effect on certain neural populations, an excitatory effect on certain neural populations, and/or both an inhibitory and excitatory effect on certain neural populations.

As used herein, the terms "neuromodulation signal", "electrical therapy signal," "electrical signal," and "therapy signal" and other associated terms are used interchangeably and generally refer to an electrical signal that can be characterized by one more parameters, such as, frequency, pulse width, and/or amplitude.

Figure 3:
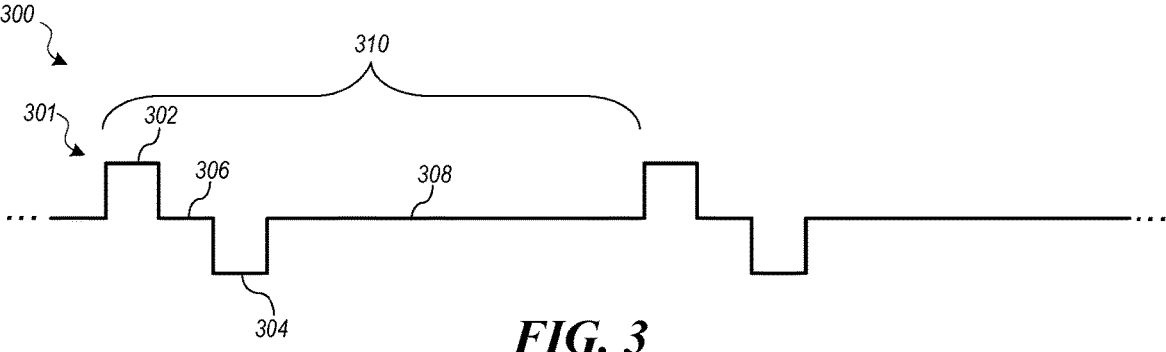
FIG. 3 is a schematic illustration of an existing high frequency electrical therapy signal.

As used herein, the term "existing high frequency neuromodulation signals," "existing high frequency signals," or the like generally refer to an electrical signal having symmetrical bi-phasic pulses having a relatively short interphase interval of about 20 microseconds or less and repeating at a frequency between about 1.2 kHz and about 100 kHz. An example of an existing high frequency neuromodulation signal is illustrated in FIG. 3.

As used herein, the terms "modified high frequency neuromodulation signals," "modified high frequency signals," or the like generally refer to an electrical signal that (a) has asymmetric bi-phasic pulses, (b) has relatively long interphase intervals, and/or (c) is administered across multiple different pairs of electrodes (also referred to herein as a "juggling pattern"). Examples of modified high frequency neuromodulation signals are illustrated in FIGS. 4A-6C.

As used herein, the term "pulse width" refers to the width of any phase of a repeating pulse, such as the portion of a pulse at a given polarity, unless explicitly described otherwise. For example, the use of the term pulse width with respect to a signal having bi-phasic pulses can refer to the duration of an anodic pulse phase or a cathodic pulse phase. The use of the term pulse width with respect to a signal having monophasic pulses can refer to the duration of the monophasic pulse phase.

As used herein, the use of the terms "delivery," "deliver," and variants thereof while describing the relationship between an electrical contact and the phase of a bi-phasic signal "delivered by" the contact describes the phase of the contact during administration of the bi-phasic pulse, and does not necessarily indicate current is flowing out of the contact. For example, if a first contact is said to "deliver" an anodic pulse phase of a bi-phasic pulse, the first contact is acting as an anode during delivery of the bi-phasic pulse. Similarly, if a second contact is said to "deliver" a cathodic pulse phase of the bi-phasic pulse, the second contact is acting as a cathode during delivery of the bi-phasic pulse.

As used herein, "proximate a spinal cord region" refers to the placement of a signal delivery element such that it can deliver electrical stimulation to a neural population associated with the spinal cord or associated nervous system structures. For example, "proximate a spinal cord region" includes, but is not limited to, the relative lead positions described and shown in FIG. 1B, as well as other positions not expressly described herein.

2.0 Overview of the Present Technology

The present technology is generally directed to spinal cord modulation and associated systems and methods for treating pain and other patient conditions. In particular, the present technology includes modified high frequency neuromodulation signals and administration patterns. For example, in some embodiments the present technology includes modified high frequency electrical therapy signals having asymmetric bi-phasic pulses. The bi-phasic pulses generally have an anodic pulse phase and a cathodic pulse phase. The anodic pulse phase and the cathodic pulse phase can have different pulse widths. For example, the cathodic pulse phase can have a greater pulse width than the anodic pulse phase. To ensure the signal is nevertheless charge balanced, the amplitude of the anodic pulse phase and the cathodic pulse phase can also be different. For example, in the foregoing example in which the cathodic pulse phase has a greater pulse width than the anodic pulse phase, the cathodic pulse phase can have a smaller amplitude than the anodic pulse phase to ensure that the total charge delivered during the bi-phasic pulse is equal and opposite.

In some embodiments, the present technology includes modified high frequency electrical therapy signals having relatively long interphase intervals between paired anodic and cathodic pulse phases. For example, the interphase interval can have a duration that is longer than the pulse width of the anodic pulse phase and/or the cathodic pulse phase. In some embodiments, the present technology includes modified high frequency electrical therapy signals administered across multiple different pairs of electrodes, such that each pulse of the signal is delivered via a pair of contacts that is different than the pair of contacts used to deliver the immediately preceding pulse.

Without being bound by any particular theory, the use of modified high frequency signals may modulate a target population of neurons in a different manner than existing high frequency signals and/or low frequency signals. For example, modified high frequency signals may preferentially modulate a first set of neurons (e.g., adapting neurons, excitatory neurons, etc.) within a target set of neurons, whereas existing high frequency signals may preferentially modulate a second set of neurons (e.g., nonadapting neurons, inhibitory neurons, etc.) within the target set of neurons. In some embodiments, the modified high frequency signals may modulate both the first set of neurons and the second set of neurons, but in a different manner than existing high frequency signals. Therefore, in some embodiments, modified high frequency signals can be administered to a patient to achieve a first physiological effect or result, and existing high frequency signals can be delivered to the patient to achieve a second physiological effect or result.

The first and second physiological effects can be complementary, synergistic, or antagonistic.

In some embodiments, the modified high frequency signals can induce a relatively rapid onset of pain relief in a patient. For example, the modified high frequency signals can induce pain relief within several hours of, within several minutes of, or simultaneous with the onset of signal administration. Accordingly, in some embodiments the modified high frequency signals can be delivered in combination with existing high frequency signals to provide more rapid onset of pain relief.

3.0 System Characteristics

FIG. 1A schematically illustrates a representative patient therapy system 100 for treating a patient's motor, sensory, and/or other functioning, arranged relative to the general anatomy of the patient's spinal column 191. The system 100 can include a signal generator 101 (e.g., an implanted or implantable pulse generator or IPG), which can be implanted subcutaneously within a patient 190 and coupled to one or more signal delivery elements or devices 110. The signal delivery elements or devices 110 can be implanted within the patient 190, at or off the patient's spinal cord midline 189. The signal delivery elements 110 carry features for delivering therapy to the patient 190 after implantation. The signal generator 101 can be connected directly to the signal delivery devices 110, or it can be coupled to the signal delivery devices 110 via a signal link, e.g., a lead extension 102. In some embodiments, the signal delivery devices 110 can include one or more elongated lead(s) or lead body or bodies 111 (identified individually as a first lead 111a and a second lead 111b). As used herein, the terms signal delivery device, signal delivery element, lead, and/or lead body include any of a number of suitable substrates and/or supporting members that carry electrodes/devices for providing therapy signals to the patient 190. For example, the lead or leads 111 can include one or more electrodes or electrical contacts that direct electrical signals into the patient's tissue, e.g., to provide for therapeutic relief. In some embodiments, the signal delivery elements 110 can include structures other than a lead body (e.g., a paddle) that also direct electrical signals and/or other types of signals to the patient 190, e.g., as disclosed in U.S. Patent Application Publication No. 2018/0256892, incorporated herein by reference in its entirety. For example, paddles can be more suitable for patients with spinal cord injuries that result in scarring or other tissue damage that impedes cylindrical leads.

In some embodiments, one signal delivery device can be implanted on one side of the spinal cord midline 189, and a second signal delivery device can be implanted on the other side of the spinal cord midline 189. For example, the first and second leads 111a, 111b shown in FIG. 1A can be positioned just off the spinal cord midline 189 (e.g., about 1 mm offset) in opposing lateral directions so that the two leads 111a, 111b are spaced apart from each other by about 2 mm. In some embodiments, the leads 111 can be implanted at a vertebral level ranging from, for example, about T4 to about T12. In some embodiments, one or more signal delivery devices can be implanted at other vertebral levels, e.g., as disclosed in U.S. Pat. No. 9,327,121, incorporated herein by reference in its entirety.

The signal generator 101 can transmit signals (e.g., electrical signals) to the signal delivery elements 110 that excite and/or suppress target nerves. The signal generator 101 can include a machine-readable (e.g., computer-readable or controller-readable) medium containing instructions for generating and transmitting suitable therapy signals, such as those described below with respect to FIGS. 3-5C. The signal generator 101 and/or other elements of the system 100 can include one or more processor(s) 107, memory unit(s) 108, and/or input/output device(s) 112. Accordingly, the process of providing modulation signals, providing guidance information for positioning the signal delivery devices 110, establishing battery charging and/or discharging parameters, and/or executing other associated functions can be performed by computer-executable instructions contained by, on, or in computer-readable media located at the pulse generator 101 and/or other system components. Further, the pulse generator 101 and/or other system components can include dedicated hardware, firmware, and/or software for executing computer-executable instructions that, when executed, perform any one or more methods, processes, and/or sub-processes described in the materials incorporated herein by reference. The dedicated hardware, firmware, and/or software also serve as "means for" performing the methods, processes, and/or sub-processes described herein. The signal generator 101 can also include multiple portions, elements, and/or subsystems (e.g., for directing signals in accordance with multiple signal delivery parameters), carried in a single housing, as shown in FIG. 1A, or in multiple housings. For example, the signal generator can include some components that are implanted (e.g., a circuit that directs signals to the signal delivery device 110), and some that are not (e.g., a power source). The computer-executable instructions can be contained on one or more media that are implanted within the patient and/or positioned external to the patient, depending on the embodiment.

The signal generator 101 can also receive and respond to an input signal received from one or more sources. The input signals can direct or influence the manner in which the therapy, charging, and/or process instructions are selected, executed, updated, and/or otherwise performed. The input signals can be received from one or more sensors (e.g., an input device 112 shown schematically in FIG. 1A for purposes of illustration) that are carried by the signal generator 101 and/or distributed outside the signal generator 101 (e.g., at other patient locations) while still communicating with the signal generator 101. The sensors and/or other input devices 112 can provide inputs that depend on or reflect patient state (e.g., patient position, patient posture, and/or patient activity level), and/or inputs that are patient-independent (e.g., time). Still further details are included in U.S. Pat. No. 8,355,797, incorporated herein by reference in its entirety.

In some embodiments, the signal generator 101 and/or signal delivery devices 110 can obtain power to generate the therapy signals from an external power source 103. For example, the external power source 103 can by-pass an implanted signal generator and generate a therapy signal directly at the signal delivery devices 110 (or via signal relay components). The external power source 103 can transmit power to the implanted signal generator 101 and/or directly to the signal delivery devices 110 using electromagnetic induction (e.g., RF signals). For example, the external power source 103 can include an external coil 104 that communicates with a corresponding internal coil (not shown) within the implantable signal generator 101, signal delivery devices 110, and/or a power relay component (not shown). The external power source 103 can be portable for ease of use.

In some embodiments, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial modulator 105 can be coupled to the signal delivery elements 110, e.g., during an initial procedure, prior to implanting the signal generator 101. For example, a practitioner (e.g., a physician and/or a company representative) can use the trial modulator 105 to vary the modulation parameters provided to the signal delivery elements 110 in real time, and select optimal or particularly efficacious parameters. These parameters can include the location from which the electrical signals are emitted, as well as the characteristics of the electrical signals provided to the signal delivery devices 110. In some embodiments, input is collected via the external stimulator or trial modulator 105 and can be used by the clinician to help determine what parameters to vary. In a typical process, the practitioner uses a cable assembly 120 to temporarily connect the trial modulator 105 to the signal delivery device 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner can move the partially implanted signal delivery devices 110 without disconnecting the cable assembly 120. Furthermore, in some embodiments, the iterative process of repositioning the signal delivery devices 110 and/or varying the therapy parameters may not be performed.

The signal generator 101, the lead extension 102, the trial modulator 105 and/or the connector 122 can each include a receiving element 109. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the pulse generator 101, the trial modulator 105 and/or the connector 122. The receiving elements 109 can be at least generally similar in structure and function to those described in U.S. Patent Application Publication No. 2011/0071593, which is incorporated by reference herein in its entirety.

After the signal delivery elements 110 are implanted, the patient 190 can receive therapy via signals generated by the trial modulator 105, generally for a limited period of time. During this time, the patient wears the cable assembly 120 and the trial modulator 105 outside the body. Assuming the trial therapy is effective or shows the promise of being effective, the practitioner then replaces the trial modulator 105 with the implanted signal generator 101, and programs the signal generator 101 with therapy programs selected based on the experience gained during the trial period. Optionally, the practitioner can also replace the signal delivery elements 110. In still further embodiments, the signal generator 101 can be implanted without first undergoing a trial period. Once the implantable signal generator 101 has been positioned within the patient 190, the therapy programs provided by the signal generator 101 can still be updated remotely via a wireless physician's programmer 117 (e.g., a physician's laptop, a physician's remote or remote device, etc.) and/or a wireless patient programmer 106 (e.g., a patient's laptop, patient's remote or remote device, etc.). Generally, the patient 190 has control over fewer parameters than does the practitioner. For example, the capability of the patient programmer 106 can be limited to starting and/or stopping the signal generator 101, and/or adjusting the signal amplitude within a present amplitude range. The patient programmer 106 can be configured to accept inputs corresponding to pain relief, motor functioning and/or other variables, such as medication use. Accordingly, more generally, embodiments of the present technology include receiving patient feedback, via a sensor, that is indicative of, or otherwise corresponds to, the patient's response to the signal. Feedback includes, but is not limited to, motor, sensory, and verbal feedback. In response to the patient feedback, one or more signal parameters can be adjusted, such as frequency, pulse width, amplitude, or delivery location.

FIG. 1B is a cross-sectional illustration of the spinal cord 191 and an adjacent vertebra 195 (based generally on information from Crossman and Neary, "Neuroanatomy," 1995 (published by Churchill Livingstone)), along with multiple leads 111 (shown as leads 111a-111e) implanted at representative locations. For purposes of illustration, multiple leads 111 are shown in FIG. 1B implanted in a single patient. In addition, for purposes of illustration, the leads 111 are shown as elongated leads however, leads 111 can be paddle leads. In actual use, any given patient will likely receive fewer than all the leads 111 shown in FIG. 1B.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193, and dorsal root ganglia 194. The dorsal roots 193 enter the spinal cord 191 at the dorsal root entry region 187, and communicate with dorsal horn neurons located at the dorsal horn 186. In some embodiments, the first and second leads 111a, 111b are positioned just off the spinal cord midline 189 (e.g., about 1 mm offset) in opposing lateral directions so that the two leads 111a, 111b are spaced apart from each other by about 2 mm, as discussed above. In some embodiments, a lead or pairs of leads can be positioned at other locations, e.g., toward the outer edge of the dorsal root entry portion 187 as shown by a third lead 111c, or at the dorsal root ganglia 194, as shown by a fourth lead 111d, or approximately at the spinal cord midline 189, as shown by a fifth lead 111e.

In some embodiments the devices and systems of the present technology include features other than those described herein. For example, one lead 111 to six leads 111 can be positioned generally end-to-end at or near the patient's midline M and span vertebral levels from about T4 to about T12. In some embodiments, two, three, or four leads 111 are positioned end-to-end at or near the patient's midline from T4 to T12. In some embodiments, the leads 111 and/or other signal delivery devices can have locations other than those expressly shown herein. For example, one or more signal delivery devices can be positioned at the dorsal side of the spinal cord 191. In addition, the devices and systems of the present technology can include more than one internal stimulator and/or more than one external stimulator that can be configured for wireless stimulation, such as by using electromagnetic waves.

Several aspects of the technology are embodied in computing devices, e.g., programmed/programmable pulse generators, controllers and/or other devices. The computing devices on/in which the described technology can be implemented can include one or more central processing units, memory, input devices (e.g., input ports), output devices (e.g., display devices), storage devices, and network devices (e.g., network interfaces). The memory and storage devices are computer-readable media that can store instructions that implement the technology. In some embodiments, the computer readable media are tangible media. In some embodiments, the data structures and message structures can be stored or transmitted via an intangible data transmission medium, such as a signal on a communications link. Various suitable communications links can be used, including but not limited to a local area network and/or a wide-area network.

FIG. 2 is a partially schematic illustration of a representative lead body 211 that can be used to apply modulation to a patient in accordance with any of the foregoing embodiments. In general, the lead body 211 includes a multitude of electrodes or contacts 220. When the lead body 211 has a circular cross-sectional shape, as shown in FIG. 2, the contacts 220 can have a generally ring-type shape and can be spaced apart axially along the length of the lead body 211. In a particular embodiment, the lead body 211 can include eight contacts 220, identified individually as first, second, third . . . eighth contacts 212, 222, 223 . . . 228. In general, one or more of the contacts 220 are used to provide signals, and another one or more of the contacts 220 provide a signal return path. Accordingly, the lead body 211 can be used to deliver monopolar modulation (e.g., if the return contact is spaced apart significantly from the delivery contact), or bipolar modulation (e.g., if the return contact is positioned close to the delivery contact and in particular, at the same target neural population as the delivery contact). In still further embodiments, the pulse generator 101 (FIG. 1A) can operate as a return contact for monopolar modulation.

4.0 Representative Therapy Signals

The present technology includes electrical therapy signals that can be delivered to a patient to treat one or more patient conditions (e.g., pain). For example, the system 100 described above can be programmed to generate and/or deliver any of the therapy signals described below. However, the therapy signals described herein can be generated and delivered using other neurostimulation systems, and are thus not limited to the systems explicitly described herein. Moreover, therapy regimens delivered in accordance with methods of the present technology can include any of the following therapy signals, including combinations thereof.

4.1 Existing High Frequency Therapy Signals

FIG. 3 is a partially schematic illustration of an existing high frequency neuromodulation signal 300. The signal 300 includes biphasic pulses 301 repeating in a continuous manner. Each individual pulse 301 includes an anodic pulse phase 302, a cathodic pulse phase 304, and an interphase interval 306 separating the anodic pulse phase 302 and the cathodic pulse phase 304. As described in greater detail below, the anodic pulse phase 302 and the cathodic pulse phase 304 are symmetrical (e.g., having generally equal pulse widths and generally equal and opposite amplitudes) such that individual pulses 301 are charge balanced. Individual pulses 301 are separated by an interpulse interval 308. Together, the pulse 301 and the interpulse interval 308 define a pulse period 310. The pulse period 310 repeats in cycles that define a frequency of the therapy signal 300.

As noted above, the pulse width of the anodic pulse phase 302 is generally equal to the pulse width of the cathodic pulse phase 304 for existing high frequency signals such as the illustrated signal 300. The anodic pulse phase 302 and the cathodic pulse phase 304 can each have a pulse width in a pulse width range of from about 1 microsecond or less and about 416 microseconds. In further embodiments, the anodic pulse phase 302 and the cathodic pulse phase 304 can each have a pulse width in a pulse width range of from about 10 microseconds to about 333 microseconds, or from about 25 microseconds to about 166 microseconds, or from about 33 microseconds to about 100 microseconds, or from about 50 microseconds to about 166 microseconds. The amplitude of the anodic pulse phase 302 and the cathodic pulse phase 304 also generally have equal values of opposite polarity. In some embodiments, the anodic pulse phase 302 and the cathodic pulse phase 304 can each have an amplitude in an amplitude range of from about 0.1 mA to about 20 mA. In further embodiments, the anodic pulse phase 302 and the cathodic pulse phase 304 can each have an amplitude in an amplitude range of from about 0.5 mA to about 10 mA, or about 0.5 mA to about 4 mA, or about 0.5 mA to about 2.5 mA. The amplitude of the therapy signal 300 can optionally be ramped up and/or down. The frequency of the therapy signal 300 can be in a frequency range of from about 1.2 kHz to about 100 kHz. In further embodiments, the therapy signal 300 can have a frequency in a frequency range of from about 1.2 kHz to about 50 kHz, from about 1.2 kHz to about 25 kHz, from about 3 kHz to about 15 kHz, or from about 5 kHz to about 15 kHz. For example, in some embodiments the therapy signal 300 has a frequency of about 5 kHz, about 10 kHz, about 15 kHz, about 20 kHz, about 25 kHz, about 50 kHz, or about 100 kHz. Additional details of symmetric therapy signals are described in U.S. Pat. No. 8,712,533, which is incorporated by reference herein in its entirety.

4.2 Therapy Signals with Asymmetric Bi-Phasic Pulses

Figure 4A:
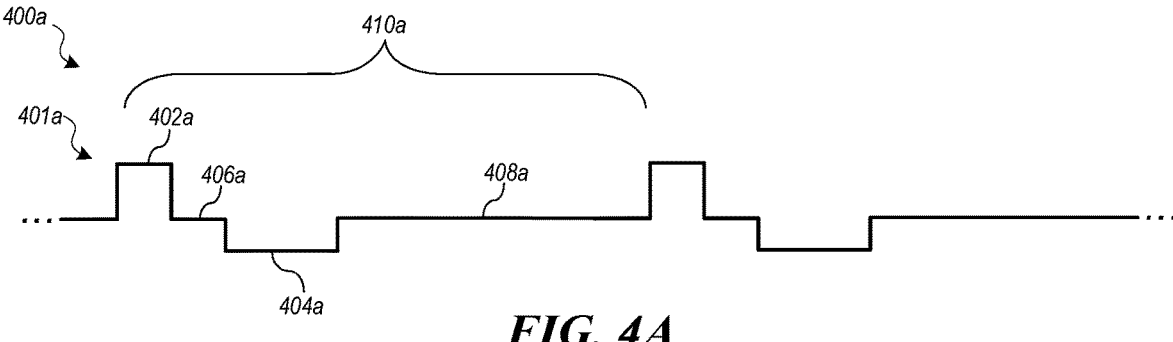
FIGS. 4A-4C are schematic illustrations of modified high frequency electrical therapy signals having asymmetric bi-phasic pulses in accordance with embodiments of the present technology.
Figure 4B:
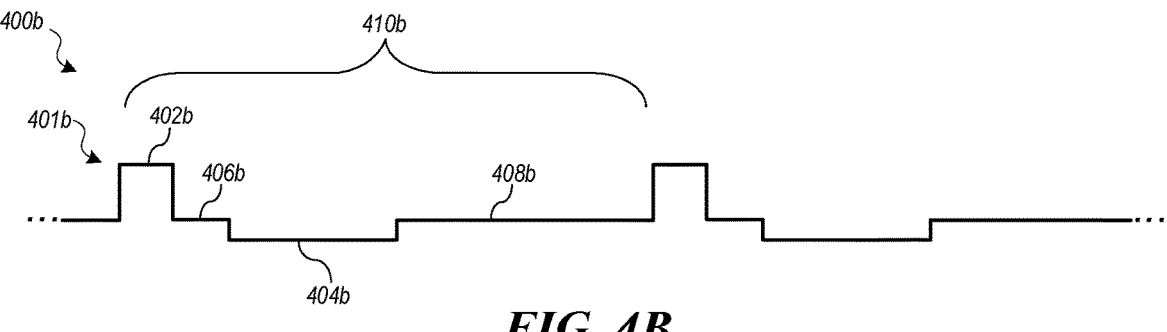
Figure 4C:
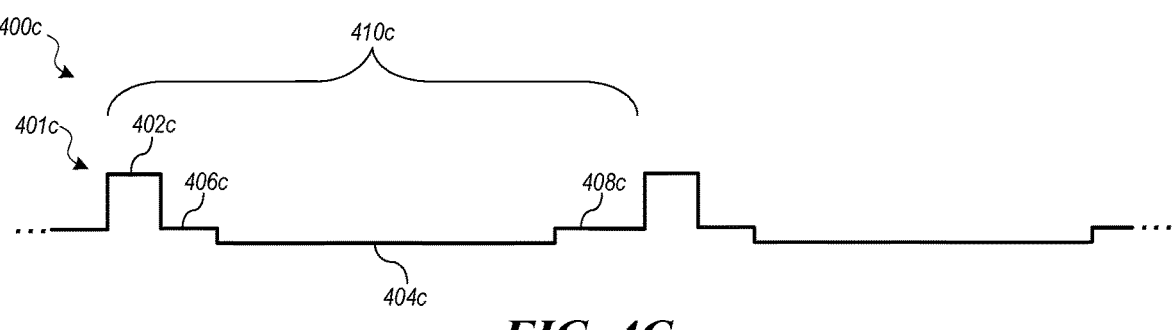

FIGS. 4A-4C are partially schematic illustrations of representative asymmetric electrical therapy signals 400a-400c (collectively referred to as the "signals 400") used to deliver therapy in accordance with embodiments of the present technology. The signals 400 each include asymmetric bi-phasic pulses 401a-c (collectively referred to as the "asymmetric bi-phasic pulses 401," or simply "pulses 401"), with each asymmetric bi-phasic pulse 401 including an anodic pulse phase 402a-c (collectively referred to as the "anodic pulse phase 402"), a cathodic pulse phase 404a-c (collectively referred to as the "cathodic pulse phase 404"), and an interphase interval 406a-c (collectively referred to as the "interphase interval 406") separating the anodic pulse phase 402 and the cathodic pulse phase 404. Although the signals 400 are shown in FIGS. 4A-4C with the anodic pulse phase 402 as the "leading phase" of the pulses 401, in other embodiments the cathodic pulse phase 404 can be the "leading phase" of the pulses 401, followed by the anodic pulse phase 402. Unlike the therapy signal 300 described with reference to FIG. 3, the anodic pulse phases 402 and the cathodic pulse phase 404 are asymmetric (e.g., they have unequal pulse widths and amplitudes). As described in greater detail below, the individual pulses 401 are nevertheless charge balanced if the total charge delivered during the anodic pulse phase 402 and the cathodic pulse phase 404 are equal and opposite. Individual bi-phasic pulses 401 are separated by an interpulse interval 408a-c (collectively referred to as the "interpulse interval 408"). Together, the pulses 401 and the interpulse intervals 408 define a pulse period 410a-c (collectively referred to as the "pulse period 410"). The pulse period 410 repeats in cycles that define a frequency of the signal 400.

As noted above, the asymmetric bi-phasic pulses 401 have anodic pulse phases 402 and cathodic pulse phases 404 having unequal pulse widths and amplitudes. In some embodiments, the cathodic pulse phases 404 have greater pulse widths than the corresponding anodic pulse phases 402. For example, the ratio between the cathodic pulse phase 404 pulse width and the anodic pulse phase 402 pulse width can be between about 1.2:1 and about 8:1, or between about 2:1 and about 6:1, or between about 2:1 and about 5:1, or between about 2:1 and about 4:1. In particular examples, the ratio can be about 2:1, about 3:1, about 4:1, about 5:1, about 6:1, about 7:1 or about 8:1. To maintain an equal and offset charge during a single bi-phase pulse 401, the cathodic pulse phases 404 can have a smaller amplitude than the corresponding anodic pulse phase 402. For example, the ratio between the cathodic pulse phase 404 amplitude absolute value and the anodic pulse phase 402 amplitude absolute value can be between about 1:1.2 and about 1:8, or between about 1:2 and about 1:6, or between about 1:2 and about 1:5, or between about 1:2 and about 1:4. In particular examples, the ratio can be about 1:2, about 1:3, about 1:4, about 1:5, about 1:6, about 1:7, or about 1:8. In some embodiments, the ratio of the cathodic pulse phase amplitude to the anodic pulse phase amplitude is the inverse of the ratio of the cathodic pulse phase pulse width to the anodic pulse phase pulse width to ensure an equal and opposite charge is delivered during each pulse 401.

In other embodiments, the anodic pulse phases 402 can have greater pulse widths than the corresponding cathodic pulse phases 404. For example, the ratio between the anodic pulse phase 402 pulse width and the cathodic pulse phase 404 pulse width can be between about 1.2:1 and about 8:1, or between about 2:1 and about 6:1, or between about 2:1 and about 5:1, or between about 2:1 and about 4:1. In such embodiments, the anodic pulse phases 402 can have a smaller amplitude than the corresponding cathodic pulse phases 404. For example, the ratio between the anodic pulse phase 402 amplitude absolute value and the cathodic pulse phase 404 amplitude absolute value can be between about 1:1.2 and about 1:8, or between about 1:2 and about 1:6, or between about 1:2 and about 1:5, or between about 1:2 and about 1:4.

In some embodiments, one pulse phase (e.g., the anodic pulse phase 402 or the cathodic pulse phase 404) provides a therapeutic effect and the other pulse phase (e.g., the other of the anodic pulse phase 402 or the cathodic pulse phase 404) provides charge balancing. Accordingly, in some embodiments the signals 400 can be described as having a therapy pulse phase and a charge balancing pulse phase. In some embodiments, the combination of the two pulse phases (e.g., the anodic pulse phase 402 and the cathodic pulse phase 404) provide the therapeutic effect.

In embodiments in which the cathodic pulse phase 404 pulse width is greater than the anodic pulse phase 402 pulse width, the anodic pulse phase 402 can have a pulse width in a pulse width range of from about 1 microsecond or less and about 416 microseconds, and the cathodic pulse phase 404 can have a pulse width in a pulse width range of from about 1.2 microseconds or less to about 740 microseconds. In further embodiments, the anodic pulse phase 402 can have a pulse width in a pulse width range of from about 10 microseconds to about 333 microseconds, or from about 25 microseconds to about 166 microseconds, or from about 33 microseconds to about 100 microseconds, or from about 50 microseconds to about 166 microseconds, and the cathodic pulse phase 404 can have a pulse width in a pulse width range of from about 12 microseconds and about 740 microseconds, or from about 30 microseconds to about 333 microseconds, or from about 40 microseconds to about 200 microseconds, or from about 60 microseconds to about 333 microseconds. In embodiments in which the anodic pulse phase 402 pulse width is greater than the cathodic pulse phase 404 pulse width, the foregoing ranges of pulse widths are reversed (e.g., the cathodic pulse phase can have a pulse width in a pulse width range of from about 1 microsecond or less to about 416 microseconds, and the anodic pulse phase can have a pulse width in a pulse width range of from about 1.2 microseconds or less to about 700 microseconds). The foregoing pulse widths are a function of the frequency of the signals 400 shown in FIGS. 4A-4C, the ratio of the cathodic pulse phase 402 pulse width to the anodic pulse phase 404 pulse width, and any interpulse or interphase interval.

In embodiments for which the anodic pulse phase 402 amplitude is greater than the cathodic pulse phase 404 amplitude, the anodic pulse phase 402 can have an amplitude in an amplitude range of from about 0.1 mA to about 20 mA, and the cathodic pulse phase 404 can have an amplitude in an amplitude range of from about 0.02 mA to about 16 mA. In further embodiments, the anodic pulse phase 402 can have an amplitude in an amplitude range of from about 0.5 mA to about 10 mA, or about 0.5 mA to about 4 mA, or about 0.5 mA to about 2.5 mA, and the cathodic pulse phase 404 can have an amplitude in an amplitude range of from about 0.1 mA to about 8 mA, or about 0.1 mA to about 3.2 mA, or about 0.1 mA to about 2 mA. In embodiments in which the anodic pulse phase 402 amplitude is less than the cathodic pulse phase 404 amplitude, the foregoing ranges of amplitudes are reversed (e.g., the cathodic pulse phase 404 can have an amplitude in an amplitude range of from about 0.1 mA to about 20 mA, and the anodic pulse phase 402 can have an amplitude in an amplitude range of from about 0.2 mA to about 16 mA).

The signals 400 can have a frequency in a frequency range of from about 1.2 kHz to about 500 kHz or even higher at narrow pulse widths. In some embodiments, the signals 400 have a frequency of from about 1.2 kHz to about 100 kHz, from about 1.2 kHz to about 50 kHz, from about 1.2 kHz to about 25 kHz, from about 3 kHz to about 15 kHz, or from about 5 kHz to about 15 kHz. For example, in some embodiments the signal 400 has a frequency of about 1.2 kHz, about 1.5 kHz, about 5 kHz, about 10 kHz, about 15 kHz, about 20 kHz, about 25 kHz, about 50 kHz, or about 100 kHz.

FIG. 4A illustrates a representative asymmetric electrical signal 400a comprising asymmetric bi-phasic pulses 401a having a cathodic pulse phase 404a with a pulse width that is approximately twice as long as the anodic pulse phase 402a pulse width (e.g., the ratio between the cathodic pulse phase 404a pulse width and the anodic pulse phase 402a pulse width is 2:1). To maintain an equal and offset charge during the bi-phase pulse 401a, the cathodic pulse phase 404a has an amplitude that has an absolute value that is approximately one-half of the absolute value of the amplitude of the anodic pulse phase 402a (e.g., the ratio between the absolute value of the cathodic pulse phase 404a amplitude and the anodic pulse phase 402a amplitude is 1:2). Accordingly, the total charge delivered during the anodic pulse phase 402a and the cathodic pulse phase 404a is equal and opposite, and the asymmetric bi-phasic pulse 401a is charge balanced. In one example, the anodic pulse phase 402a has a pulse width of about 20 microseconds, the cathodic pulse phase 404a has a pulse width of about 40 microseconds, and the signal 400a has a frequency of about 5 kHz.

FIG. 4B illustrates a representative asymmetric electrical signal 400b comprising asymmetric bi-phasic pulses 401b having a cathodic pulse phase 404b with a pulse width that is approximately three times as long as the anodic pulse phase 402b pulse width (e.g., the ratio between the cathodic pulse phase 404b pulse width and the anodic pulse phase 402b pulse width is 3:1). To maintain an equal and offset charge during the bi-phase pulse 401b, the cathodic pulse phase 404b has an amplitude that has an absolute value that is approximately one-third of the absolute value of the amplitude of the anodic pulse phase 402b (e.g., the ratio between the absolute value of the cathodic pulse phase 402b amplitude and the anodic pulse phase 402b amplitude is 1:3). Accordingly, the total charge delivered during the anodic pulse phase 402b and the cathodic pulse phase 404b is equal and opposite, and the asymmetric bi-phasic pulse 401b is charge balanced. In one example, the anodic pulse phase 402b has a pulse width of about 20 microseconds, the cathodic pulse phase 404b has a pulse width of about 60 microseconds, and the signal 400a has a frequency of about 5 kHz.

FIG. 4C illustrates a representative asymmetric electrical signal 400c comprising asymmetric bi-phasic pulses 401c having a cathodic pulse phase 404c with a pulse width that is approximately six times as long as the anodic pulse phase 402c pulse width (e.g., the ratio between the cathodic pulse phase 404c pulse width and the anodic pulse phase 402c pulse width is 6:1). To maintain an equal and offset charge during the bi-phase pulse 401c, the cathodic pulse phase 404c has an amplitude that has an absolute value that is approximately one-sixth of the absolute value of the amplitude of the anodic pulse phase 402c (e.g., the ratio between the absolute value of the cathodic pulse phase 402c amplitude and the anodic pulse phase 402c amplitude is 1:6). Accordingly, the total charge delivered during the anodic pulse phase 402c and the cathodic pulse phase 404c is equal and opposite, and the asymmetric bi-phasic pulse 401c is charge balanced. In one example, the anodic pulse phase 402c has a pulse width of about 20 microseconds, the cathodic pulse phase 404c has a pulse width of about 120 microseconds, and the signal 400a has a frequency of about 5 kHz.

Without being bound by any particular theory, the use of asymmetric pulses during neurostimulation therapy may modulate a target population of neurons in a different manner than the use of existing symmetrical pulses. For example, asymmetric pulses may preferentially modulate a first set of neurons (e.g., adapting neurons, excitatory neurons, etc.) within a target set of neurons, whereas existing symmetrical pulses may preferentially modulate a second set of neurons (e.g., nonadapting neurons, inhibitory neurons, etc.) within the target set of neurons. In some embodiments, the asymmetric pulses may modulate both the first set of neurons and the second set of neurons, but in a different manner than and/or to a different degree than (e.g., greater than, less than, etc.) existing symmetrical pulses. Therefore, in some embodiments, signals having asymmetric pulses can be delivered to achieve a first physiological effect or result, and signals having symmetric pulses can be delivered to achieve a second physiological effect or result. The first and second physiological effects can be complementary, synergistic, or antagonistic. Additional details regarding potential effects of, and mechanisms of action for, asymmetric pulses are described in Section 6.0 below.

4.3 Therapy Signals with Relatively Long Inter-Phase Intervals

Figure 5A:
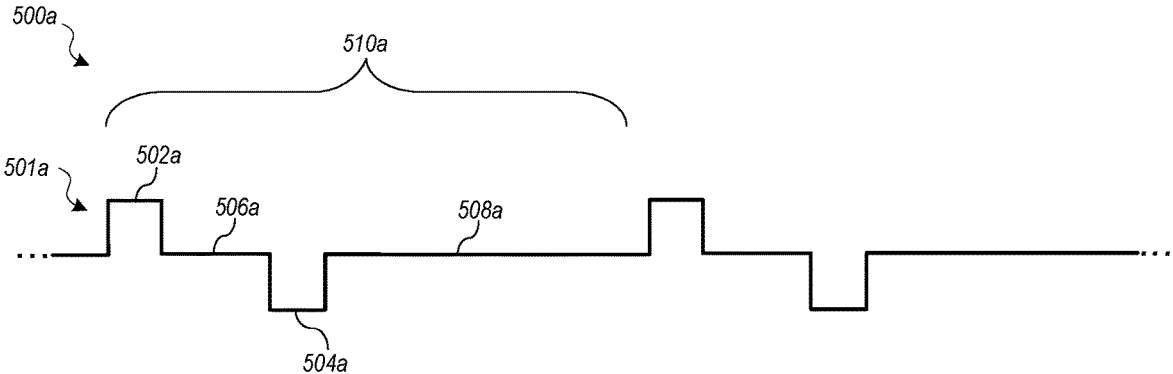
FIGS. 5A-5C are schematic illustrations of additional modified high frequency electrical therapy signals having relatively long interphase intervals in accordance with embodiments of the present technology.
Figure 5B:
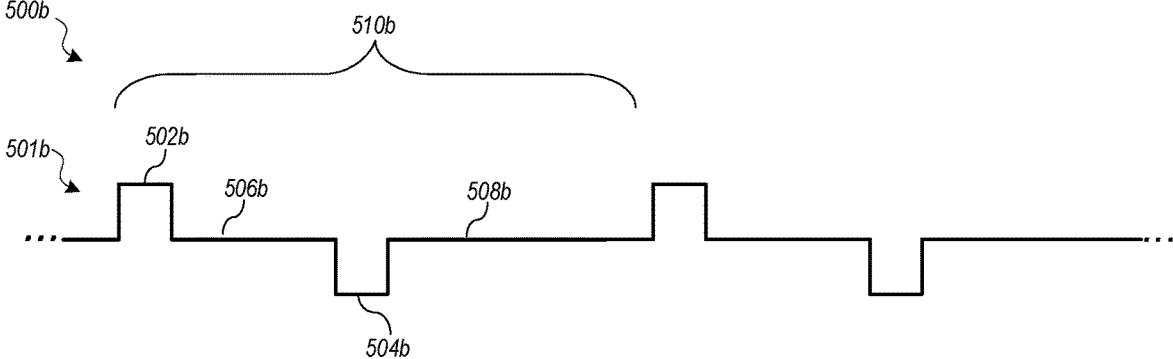
Figure 5C:
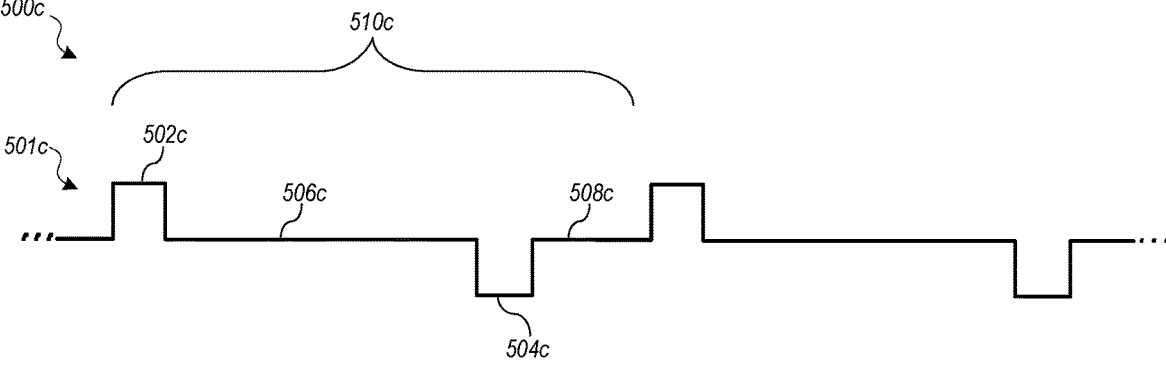

FIGS. 5A-5C are partially schematic illustrations of representative electrical therapy signals 500a-500c (collectively referred to as the "signals 500") used to deliver therapy in accordance with embodiments of the present technology. The signals 500 each include bi-phasic pulses 501a-c (collectively referred to as the "bi-phasic pulses 501," or simply "pulses 501"), with each bi-phasic pulse 501 including an anodic pulse phase 502a-c (collectively referred to as the "anodic pulse phase 502"), a cathodic pulse phase 504a-c (collectively referred to as the "cathodic pulse phase 504"), and an interphase interval 506a-c (collectively referred to as the "interphase interval 506") separating the anodic pulse phase 502 and the cathodic pulse phase 504. Although the therapy signals 500 are shown in FIGS. 5A-5C with the anodic pulse phase 502 as the "leading phase" of the pulses 501, in other embodiments the cathodic pulse phase 504 can be the "leading phase" of the pulses 501, followed by the anodic pulse phase 502. Moreover, although described as having anodic pulse phases and cathodic pulse phases, the signals 500 can also be described as having a therapy pulse phase (e.g., shown in FIGS. 5A-5C as the anodic pulse phase 502) followed by a charge balancing pulse phase (e.g., shown in FIGS. 5A-5C as the cathodic pulse phase 504). The interphase interval 506 is the duration between the leading pulse phase (e.g., the therapy pulse phase) and the following pulse phase (e.g., the charge balancing pulse phase). Individual bi-phasic pulses 501 are separated by an interpulse interval 508a-c (collectively referred to as the "interpulse interval 508"). Together, the pulses 501 and the interpulse intervals 508 define a pulse period 510a-c (collectively referred to as the "pulse period 510"). The pulse period 510 repeats in cycles that define a frequency of the signal 500.

Unlike the therapy signals 300 and 400 described with reference to FIGS. 3-4C, the signals 500 shown in FIGS. 5A-5C have an interphase interval 506 that is greater than the pulse width of the leading pulse phase, which in the embodiment illustrated in FIGS. 5A-5C is the anodic pulse phase 502. Accordingly, the term "relatively long interphase interval" is used herein to refer to an interphase interval having a duration greater than the pulse width of the leading pulse phase. A ratio between the duration of the interphase interval 506 and the pulse width of the leading pulse phase can be between about 1.2:1 and about 8:1, or between about 2:1 and about 6:1, or between about 2:1 and about 5:1, or between about 2:1 and about 4:1. In some embodiments, the ratio is about 2:1, about 3:1, about 4:1, about 5:1, about 6:1, about 7:1, or about 8:1. In some embodiments, the duration of the relatively long interphase interval is between about 24 microseconds and about 160 microseconds, or between about 30 microseconds and about 120 microseconds, or between about 40 microseconds and about 80 microseconds, or about 60 microseconds. In some embodiments, an increase in the interphase interval 506 is accompanied by a corresponding decrease in the interpulse interval 508, such that the duration of the pulse period 610, and therefore the frequency, remains unchanged.

While the interphase interval 506 is proportionally larger than the interphase interval 306 of the signal 300 shown in FIG. 3, the pulse width, amplitudes, and frequencies of the signal 500 can be generally the same as those described with respect to the signals 300 and/or 400. For example, in some embodiments the pulse width of the anodic pulse phase 502 is generally equal to the pulse width of the cathodic pulse phase 504, although in other embodiments the anodic pulse phase 502 pulse width is not equal to the cathodic pulse phase 504 pulse width. In some embodiments, the anodic pulse phase 502 and the cathodic pulse phase 504 can each have a pulse width in a pulse width range of from about 1 microsecond or less and about 416 microseconds. In further embodiments, the anodic pulse phase 502 and the cathodic pulse phase 504 can each have a pulse width in a pulse width range of from about 10 microseconds to about 333 microseconds, or from about 25 microseconds to about 166 microseconds, or from about 33 microseconds to about 100 microseconds, or from about 50 microseconds to about 166 microseconds.

The amplitude of the anodic pulse phase 302 and the cathodic pulse phase 304 also generally have equal values of opposite polarity. In some embodiments, the anodic pulse phase 502 and the cathodic pulse phase 504 can each have an amplitude in an amplitude range of from about 0.1 mA to about 20 mA. In some embodiments, the anodic pulse phase 502 and the cathodic pulse phase 504 can each have an amplitude in an amplitude range of from about 0.5 mA to about 10 mA, or about 0.5 mA to about 4 mA, or about 0.5 mA to about 2.5 mA. The amplitude of the signals 500 can optionally be ramped up and/or down. The frequency of the signals 500 can be in a frequency range of from about 1.2 kHz to about 500 kHz. In some embodiments, the therapy signals 500 can have a frequency in a frequency range of from about 1.2 kHz to about 100 kHz, from about 1.2 kHz to about 50 kHz, from about 1.2 kHz to about 25 kHz, from about 3 kHz to about 15 kHz, or from about 5 kHz to about 15 kHz. For example, in some embodiments the signals 500 have a frequency of about 1.2 kHz, about 1.5 kHz, about 5 kHz, about 10 kHz, about 15 kHz, about 20 kHz, about 25 kHz, about 50 kHz, or about 100 kHz.

FIG. 5A illustrates a representative electrical signal 500a having an interphase interval 506a that is twice as long as the pulse width of the anodic pulse phase 502a (e.g., the ratio between the duration of the interphase interval 506a and the anodic pulse phase 502a pulse width is 2:1). In one example, the anodic pulse phase 502a has a pulse width of about 20 microseconds, the interphase interval 506b has a duration of about 40 microseconds, and the signal 500a has a frequency of about 5 kHz.

FIG. 5B illustrates a representative electrical signal 500b having an interphase interval 506b that is three times as long as the pulse width of the anodic pulse phase 502b (e.g., the ratio between the duration of the interphase interval 506b and the anodic pulse phase 502b pulse width is 3:1). In one example, the anodic pulse phase 502b has a pulse width of about 20 microseconds, the interphase interval 506b has a duration of about 60 microseconds, and the signal 500b has a frequency of about 5 kHz.

FIG. 5C illustrates a representative electrical signal 500c having an interphase interval 506c that is six times as long as the pulse width of the anodic pulse phase 502c (e.g., the ratio between the duration of the interphase interval 506c and the anodic pulse phase 502c pulse width is 6:1). In one example, the anodic pulse phase 502c has a pulse width of about 20 microseconds, the interphase interval 506c has a duration of about 120 microseconds, and the signal 500a has a frequency of about 5 kHz.

Without being bound by any particular theory, the use of electrical signals having relatively long interphase intervals may modulate a target population of neurons in a different manner than existing electrical signals. For example, the signals 500 may preferentially modulate a first set of neurons (e.g., adapting neurons, excitatory neurons, etc.) within a target set of neurons, whereas existing signals (e.g., those in which the interphase interval is equal to or less than the pulse width of the anodic pulse phase) may preferentially modulate a second set of neurons (e.g., nonadapting neurons, inhibitory neurons, etc.) within the target set of neurons. In some embodiments, the signals 500 may modulate both the first set of neurons and the second set of neurons, but in a different manner and/or to a different degree than (e.g., greater than, less than, etc.) existing signals. Therefore, in some embodiments, signals having relatively long interphase intervals can be delivered to achieve a first physiological effect or result, and signals having existing interphase intervals can be delivered to achieve a second physiological effect or result. The first and second physiological effects can be complementary, synergistic, or antagonistic. Additional details regarding potential effects of, and mechanisms of action for, biphasic pulses having relatively long interphase intervals are described in Section 6.0 below.

5.0 Representative Patterns of Administration

In some embodiments, electrical signals in accordance with the present technology can be administered via more than two electrodes or contacts, with each pulse of the signal delivered via a pair of contacts that is different than the pair of contacts used to deliver the immediately preceding pulse. FIG. 6A illustrates an example of such a pattern of administration, which can also be referred to herein as a "juggling" pattern. More specifically, FIG. 6A illustrates an electrical therapy signal 600 having mono-phasic pulses (shown as a first mono-phasic pulse 601a, a second mono-phasic pulse 601b, and a third mono-phasic pulse 601c).

FIG. 6A further illustrates a signal delivery element or lead 620 having a first contact or electrode 621, a second contact or electrode 622, and a third contact or electrode 623. The signal delivery element 620 is shown three times in FIG. 6A to illustrate the pattern of contact(s) used to deliver the pulses. The first pulse 601a is delivered via the first contact 621 and the second contact 622 (e.g., electrical current flows out of the first contact 621 and into the second contact 622). The second pulse 601b is subsequently delivered via the second contact 622 and the third contact 623 (e.g., electrical current flows out of the second contact 622 and into the third contact 623). The third pulse 601c is subsequently delivered via the third contact 623 and the first contact 621 (e.g., electrical current flows out of the third contact 623 and into the first contact 622). This pattern of administration can be repeated with subsequent pulses of the signal 600, such that no two adjacent pulses are delivered via the same pair of contacts. Although shown with three contacts, the signal 600 can be administered according to the juggling pattern described above with any number of contacts greater than two, such as three, four, five, six, seven, eight, nine, ten, or more contacts. The pairing of electrodes can also be changed for any given pulse. For example, electrical current could flow from the first contact 621 to the third contact 623 during a first pulse, from the third contact 623 to the second contact 622 during a second pulse, and from the second contact 622 to the first contact 621 during a first pulse.

Despite the signal 600 being mono-phasic, the contacts 621-623 do not build up significant charge because each contact delivers and receives the same amount of current. FIG. 6B is a schematic representation of the charge at each contact 621-623 during administration of the pulses 601a-

601c. For the first pulse 601a, the first contact 621 has a positive charge change, the second contact 622 has a negative charge change, and the third contact has no charge change. For the second pulse 601b, the first contact 621 has no charge change, the second contact 622 has a positive charge change, and the third contact 623 has a negative charge change. For the third pulse 601c, the first contact has a negative charge change, the second contact 622 has no charge change, and the third contact has a positive charge change. Therefore, the first contact 621 experiences a positive charge during the first pulse 601a that is balanced by the negative charge during the third pulse 601c, the second contact 622 experiences a negative charge during the first pulse 601a that is balanced by the positive charge during the second pulse 601b, and the third contact 623 experiences a negative charge during the second pulse 601b that is balanced by the positive charge during the third pulse 601c. Accordingly, for delivery patterns using three contacts such as those illustrated, combining three mono-phasic pulses forms a set of pulses that results in each electrode being charge balanced. The number of mono-phasic pulses forming the charge balanced pulse set depends on the number of electrodes used. For example, if four electrodes are used then four monophasic pulses form the charge balanced set of pulses, if five electrodes are used then five monophasic pulses form the charge balanced set of pulses, and so on.

Signals having asymmetric pulses can also be delivered according to the juggling pattern while maintaining charge-balancing at the contacts 621-623, provided the total charge at each electrode is offset. For example, FIG. 6C illustrates a monophasic signal 650 having a plurality of pulses, each having a different amplitude and pulse width (e.g., shown as a first monophasic pulse 651a, a second monophasic pulse 651b, and a third monophasic pulse 651c). Of note, the amplitude and pulse widths of the pulses 651a-c are inversely proportional such that the total charge delivered by each pulse is the same or at least substantially the same. FIG. 6C also shows the charge at each contact 621-623 during administration of the pulses 651a-c. Because the total charge delivered by each pulse 651a-c is the same, the contacts 621-623 remain substantially charge balanced after delivery of the three pulses 651a-651c.

The foregoing pattern is different than both existing bipolar and tripolar patterns of administration (referred to herein as "existing administration patterns"), which are used to administer conventional bi-phasic pulses. In existing bipolar administrations, a single pair of contacts is used to deliver the signal, with a first contact delivering the anodic pulse and a second contact delivering the cathodic pulse. In existing tripolar patterns of administration, three contacts are used to deliver the signal, with a first contact delivering the anodic pulse and second and third contacts positioned on opposing sides of the first contact delivering the anodic pulses (or vice versa). In both existing bipolar and tripolar patters, the contacts generally remain as either an anode or a cathode, and do not switch between phases. In contrast, when using the juggling pattern described herein, a single contact can act as an anode for a first pulse, a cathode for a second pulse, and be neutral for a third pulse. This increases the area of the current loop extending between the contacts during administration of the electrical signal, and thus may increase the biological area that is affected by (e.g., the number of neurons recruited by) the electrical signals.

Without being bound by any particular theory, administering electrical signals via a juggling pattern may modulate a target population of neurons in a different manner than administering the same electrical signal via existing patterns. For example, administering a signal using the juggling pattern may preferentially modulate a first set of neurons (e.g., adapting neurons, excitatory neurons, etc.) within a target set of neurons, whereas administering the signal using an existing pattern may preferentially modulate a second set of neurons (e.g., nonadapting neurons, inhibitory neurons, etc.) within the target set of neurons. In some embodiments, administering a signal using the juggling pattern may modulate both the first set of neurons and the second set of neurons, but in a different manner than and/or to a different degree than administering a signal using an existing pattern of administration. In some embodiments, administering a signal using the juggling patterns may modulate a larger target area (thus modulating more neurons) than the same signal administered via an existing pattern. Therefore, in some embodiments, signals can be delivered using the juggling pattern to achieve a first physiological effect or result, and signals can be delivered using the existing pattern to achieve a second physiological effect or result. The first and second physiological effects can be complementary, synergistic, or antagonistic. Additional details regarding potential effects of, and mechanisms of action for, the juggling pattern of administration are described in Section 6.0 below.

6.0 Selectivity of Modified High Frequency Neuromodulation Signals

As described above, the modified high frequency neuromodulation signals (e.g., the asymmetric signals described with respect to FIGS. 4A-4C, the signals having relatively long interphase intervals described with respect to FIGS. 5A-5C, and signals delivered in accordance with a juggling pattern as described with respect to FIGS. 6A-6C) can modulate a target population of neurons in a different manner than existing high frequency neuromodulation signals administered via an existing pattern. FIG. 7 is a graph showing the firing rate of excitatory neurons and inhibitory neurons in response to select high frequency neuromodulation signals. Line 701 reflects the relative firing rate of excitatory versus inhibitory neurons for an existing 10 kHz electrical signal administered at various percentages of a motor threshold. Line 702 reflects the relative firing rate of excitatory versus inhibitory neurons for an existing 50 kHz electrical signal administered at various percentages of a motor threshold. Line 703 reflects the relative firing rate of excitatory versus inhibitory neurons for an electrical signal administered according to a "juggling" pattern and at various percentages of a motor threshold.

Without intending to be bound by any particular theory, and as shown by lines 701 and 702, existing high frequency electrical signals can preferentially activate inhibitory neurons relative to excitatory neurons regardless of the intensity of the signal. For example, a 10 kHz electrical signal administered at 30% of motor threshold induces a 10 Hz firing rate in inhibitory neurons but only a 2 Hz firing rate in excitatory neurons, while the same 10 kHz electrical signal administered at 60% of motor threshold induces a 27 Hz firing rate in excitatory neurons but only a 6 Hz firing rate in excitatory neurons. Likewise, a 50 kHz electrical signal administered at 30% of motor threshold induces about a 23 Hz firing rate in inhibitory neurons but only about a 4 Hz firing rate in excitatory neurons.

In contrast, modified high frequency neuromodulation signals can modulate a target population of neurons in a different manner. As shown by line 703, administering an electrical signal according to a juggling pattern can have a greater influence on excitatory neurons than inhibitory neurons, particularly as the intensity of the administered signal increases toward motor threshold. For example, while administering the signal at 10% motor threshold appears to preferentially activate inhibitory neurons, administering the signal at 30% motor threshold and above appears to preferentially activate excitatory neurons.

FIGS. 8A-8C are graphs further demonstrating the effects of modified high frequency neuromodulation signals having asymmetric bi-phasic pulses (e.g., the signals 400 described with respect to FIGS. 4A-4C). More specifically, FIG. 8A illustrates the firing rate of excitatory neurons in response to an existing 5 kHz electrical signal having symmetric bi-phasic pulses with a cathodic pulse phase pulse width to anodic pulse phase pulse width ratio of 1:1, and several modified 5 kHz neuromodulation signals having asymmetric bi-phasic pulses with cathodic pulse phase pulse width to anodic pulse phase pulse width ratios of 2:1, 3:1, and 6:1. Data is shown for signals administered at both 30% motor threshold and 60% motor threshold. FIG. 8B illustrates the same, but for inhibitory neurons. FIG. 8C is a line graph comparing the firing rate of excitatory neurons versus the firing rate of inhibitory neurons. In particular, line 801 reflects the relative firing rate of excitatory versus inhibitory neurons for the existing 5 kHz symmetric signal having a 1:1 ratio at various percentages of motor threshold, and line 802 reflects the relative firing rate of excitatory versus inhibitory neurons for the 5 kHz asymmetric signal having a 2:1 ratio at various percentages of motor threshold. Additionally, line 803 reflects the relative firing rate of excitatory versus inhibitory neurons for the 5 kHz asymmetric signal having a 3:1 ratio at various percentages of motor threshold, and line 804 reflects the relative firing rate of excitatory versus inhibitory neurons for the 5 kHz asymmetric signal having a 6:1 ratio at various percentages of motor threshold.

As shown in FIGS. 8A-8C, the 5 kHz signals with asymmetric bi-phasic pulses did not preferentially activate excitatory neurons but nevertheless generally activated excitatory neurons at a greater rate than did the existing symmetric 5 kHz signal. Moreover, the 5 kHz asymmetric signal with a 3:1 ratio between the cathodic pulse phase pulse width and the anodic pulse phase pulse width generally activated both inhibitory neurons and excitatory neurons at the highest rate compared to the other signals. Without intending to be bound by any particular theory, a ratio of 3:1 may induce the strongest activation because, at such ratio, the cathodic pulse phase has the least impact on neuronal response to the anodic pulse phase. At higher ratios, the cathodic pulse phase may impact neuronal response to the anodic pulse phase of the next pulse. At lower ratios, the cathodic pulse phase may impact neuronal response to the paired anodic pulse phase.

FIG. 9 is a graph further demonstrating the selective modulation effects of modified high frequency neuromodulation signals having relatively long interphase intervals (e.g., the signals 500 described with respect to FIGS. 5A-5C). More specifically, FIG. 9 illustrates the firing rate of neurons in response to an existing 5 kHz electrical signal having bi-phasic pulses with an interphase interval to leading phase pulse width ratio of 1:1 (e.g., pulses having a leading anodic pulse phase pulse width of 20 microseconds and an interphase interval of 20 microseconds). FIG. 9 also illustrates several modified 5 kHz neuromodulation signals having relatively long interphase intervals, and having interphase interval to leading phase pulse width ratios of 2:1, 3:1, and 6:1 (e.g., pulses having a leading anodic pulse phase pulse width of 20 microseconds and an interphase interval of 40 microseconds, 60 microseconds, and 120 microseconds, respectively). The data shown in FIG. 9 was obtained invitro by increasing the amplitude of the various signals until a neuronal response was detected.

The modified 5 kHz signals with relatively long interphase intervals generally activated neurons at a greater rate than did the existing 5 kHz signal. Moreover, the modified 5 kHz signal with a 3:1 ratio between the interphase interval and the leading phase pulse width generally activated neurons at the highest rate compared to the other signals. Without intending to be bound by any particular theory, a ratio of 3:1 may induce the strongest neuronal response because, at such a ratio, the second pulse phase of the pulse (e.g., the cathodic pulse phase) may have less impact on neuron response to the leading pulse phase of the pulse (e.g., the anodic pulse phase). At high ratios, the second pulse phase of the pulse may impact neuronal response to the leading pulse phase of the next pulse. At lower ratios, the second pulse phase of the pulse may impact neuronal response to the paired leading pulse phase.

In some embodiments, and without being bound by theory, the different activation patterns induced by existing (e.g., symmetric bi-phasic signals having relatively short interphase intervals and delivered using standard patterns) versus modified high frequency neuromodulation signals can also be described in terms of adapting versus non-adapting neurons. For example, existing high frequency signals can preferentially activate non-adapting neurons, while modified high frequency signals can preferentially activate adapting neurons (or at least activate a different fraction of adapting versus non-adapting neurons).

In some patients, the different activation patterns induced by existing versus modified high frequency neuromodulation signals may be explained based on the reach of the signals. Without being bound by theory, modified high frequency signals may activate neurons in a larger and/or different area than existing high frequency signals. For example, the modified high frequency signals may activate excitatory neurons that project to and therefore activate inhibitory interneurons that are outside the reach of existing high frequency signals. By activating neurons in a larger and/or different area, the modified high frequency neuromodulation signals increase the "reach" of the signal and thus result in increased activation of both excitatory and inhibitory neurons.

7.0 Combination Therapy

Any of the neuromodulation signals and administration patterns described herein can be used in combination. For example, the neuromodulation systems can be programmed with instructions for delivering existing high frequency signals, modified high frequency signals having asymmetric bi-phasic pulses, and/or modified high frequency signals having relatively long interphase intervals. Combination therapy can include delivering two or more different waveforms temporally (e.g., delivering a modified high frequency signal having asymmetric bi-phasic pulses or relatively long interphase intervals for a first period of time, and delivering existing high frequency signals for a second period of time after the first period of time using). In some embodiments, the first period of time may at least partially overlap with the second period of time. In other embodiments, the first period of time does not overlap with the second period of time. Combination therapy can also include delivering two or more different waveforms spatially (e.g., delivering a modified high frequency signal having asymmetric bi-phasic pulses or relatively long interphase intervals using a first set of electrodes, and delivering existing high frequency signals using a second set of electrodes). Combination therapy can also include delivering two or more different waveforms temporo-spatially (e.g., delivering a modified high frequency signal having asymmetric bi-phasic pulses or relatively long interphase intervals for a first period of time using a first set of electrodes, and delivering existing high frequency signals for a second period of time after the first period of time using a second set of electrodes). The systems can also be programmed to deliver neuromodulation signals via an existing administration pattern and/or a juggling pattern. In some embodiments, combining multiple therapies is expected to provide one or more advantages, described below.

It has been demonstrated that existing high frequency neuromodulation signals having a frequency in a frequency range of 1.2 kHz to 100 kHz can exhibit a "wash-in" period when administered to treat pain in a patient. The wash-in period refers to the period of time between the onset of signal administration and the onset of therapeutic relief (e.g., pain relief) provided by the signal. This wash-in period can last for a period of time extending from several hours to several days. This wash-in period can be disadvantageous because (1) patients can continue to suffer from pain during this period, and (2) it can make it more challenging to identify which patients respond best to the therapy (e.g., a healthcare provider may need to wait for several days after initial administration to determine if the therapy will be effective in any given patient). Of course, existing high frequency neuromodulation nevertheless provides many benefits, such as those described in U.S. Pat. No. 8,712,533, previously incorporated by reference herein, that make it an attractive therapy option for many patients despite the delayed onset of pain relief.

The modified high frequency neuromodulation signals described herein (e.g., the asymmetric signals described with respect to FIGS. 4A-4C, the signals having relatively long interphase intervals described with respect to FIGS. 5A-5C, and signals delivered in accordance with a juggling pattern as described with respect to FIGS. 6A-6C) can exhibit a more rapid onset of pain relief (e.g., within seconds, within minutes, within hours, etc.) and thus may not be subject to the foregoing disadvantages. For example, FIG. 10 is a graph 1000 illustrating Von Frey paw withdrawal thresholds for rats subjected to various therapies described herein. In particular, the x-axis measures time and the y-axis measures the Von Frey paw withdrawal threshold in grams. For the x-axis, the "baseline" data set was obtained by performing the Von Frey paw withdrawal test on healthy rats, the "prestim" data set was obtained by performing the Von Frey paw withdrawal test following surgical intervention to sensitize the rats, and the "day 1", "day 3", and "day 7" data sets were obtained by performing the Von Frey paw withdrawal test after the sensitized rat received stimulation for one day, three days, and 7 days, respectively. Line 1001 illustrates results for rats receiving existing 10 kHz stimulation comprising symmetric bi-phasic pulses, line 1002 illustrates results for rats receiving 5 kHz stimulation with a relatively long interphase interval (e.g., the signals 500a-500c described with respect to FIGS. 5A-5C), and line 1003 illustrates results for rats receiving 5 kHz stimulation with asymmetric pulses (e.g., the signals 400a-400c described with respect to FIGS. 4A-4C). More specifically, the 5 kHz stimulation with the relatively long interphase interval (line 1002) had a leading pulse phase pulse width of 20 microseconds, an interphase interval of 60 microseconds, and a charge balancing phase pulse width of 20 microseconds. Similarly, the 5 kHz asymmetric stimulation (line 1003) had a leading pulse phase pulse width of 20 microseconds and a charge balancing phase pulse width of 60 microseconds.

As shown in FIG. 10, both the 5 kHz long interphase interval stimulation (line 1002) and the 5 kHz asymmetric stimulation (line 1003) resulted in greater pain relief than the existing 10 kHz stimulation (line 1001) at days 1, 3, and 7, as measured by the rat being able to withstand a greater stimulus before the paw withdrawal reflex was activated. In other words, the 5 kHz long interphase interval stimulation and the 5 kHz asymmetric stimulation both demonstrated a more rapid onset of pain relief that was greater in magnitude than pain relief achieved with existing signals for at least the first week of stimulation. Without intending to be bound by theory, this may be in part a result of the modified high frequency neuromodulation signals directly activating excitatory neurons, which, once activated, can activate neighbor inhibitory interneurons not reachable by existing symmetric waveforms because existing symmetric waveforms preferentially activate inhibitory neurons proximate the lead and therefore do not trigger network effects. The activated neighbor inhibitory interneurons could drive inhibition of the second order projection neurons that may be at least partially responsible for the patient's pain. Accordingly, the foregoing signals can be delivered to a patient in combination with existing high frequency neuromodulation to (1) provide a more rapid onset of pain relief, and/or (2) assist in more rapidly identifying which patients respond to high frequency neuromodulation.

FIG. 11 illustrates a graph 1100 illustrating the potential therapeutic effect of combining different types of high frequency neuromodulation signals. Line 1101 illustrates the expected level of pain relief over time for an existing high frequency neuromodulation signal. Line 1102 illustrates the expected level of pain relief over time for a modified high frequency neuromodulation signal (e.g., an asymmetric signal, a signal having a relatively long interphase interval, and/or a signal administered according to a juggling pattern). Line 1103 illustrates the expected level of pain relief over time if an existing high frequency neuromodulation signal is delivered in combination with a modified neuromodulation signal. As illustrated, the existing high frequency neuromodulation signal is expected to demonstrate a delayed onset of pain relief, but, after the initial wash in period, is expected to provide prolonged and robust pain relief. In contrast, the modified high frequency neuromodulation signal is expected to demonstrate a relatively rapid onset of pain relief, but, in certain patients, the pain relief may fall off after an initial period (e.g., due to adaptation of the modulated neurons, as described in Section 6.0). However, the combined effect of the existing high frequency neuromodulation signal is expected to provide both relatively rapid onset of pain relief (from the modified high frequency neuromodulation signal) and prolonged pain relief (from the existing high frequency neuromodulation signal). In some patients, the modified high frequency neuromodulation signal may provide a relatively rapid onset of pain relief that persists for a prolonged period, and therefore may not need to be combined with an existing high frequency neuromodulation signal.

In addition to the foregoing benefit, delivering one or more of the modified signals described herein with existing high frequency signals can help identify if a patient is more likely to respond to high frequency therapy. As previously described, it can take several hours to several days for a patient to have a therapeutic effect from existing high frequency neuromodulation. In contrast, the modified high frequency neuromodulation signals described herein can induce a relatively rapid (e.g., less than several hours, less than several minutes, simultaneous, etc.) onset of pain relief. The patient's response to the modified high frequency neuromodulation signals can therefore be used to project whether the patient will respond to existing high frequency signals. This can decrease time and costs, since an entire trial procedure could be conducted during a single patient visit to a healthcare provider.

In some embodiments, systems in accordance with the present technology can be programmed to simultaneously generate and/or deliver existing high frequency signals and modified high frequency signals (e.g., modified high frequency signals having asymmetric bi-phasic pulses, modified high frequency signals having relatively long interphase intervals, and/or mono-phasic high frequency pulses administered via a juggling pattern). For example, the systems can deliver a modified high frequency signal to provide initial pain relief and/or determine whether the patient responds to high frequency neurostimulation. At the same time, the systems can also deliver an existing high frequency signal to initiate the wash-in period.

In some embodiments, systems in accordance with the present technology can be programmed to generate and/or deliver a modified high frequency signal (e.g., modified high frequency signals having asymmetric bi-phasic pulses, modified high frequency signals having relatively long interphase intervals, and/or mono-phasic high frequency pulses administered via a juggling pattern) before generating and/or delivering an existing high frequency signal. For example, the systems can deliver a modified high frequency signal to provide initial pain relief and/or determine whether the patient responds to high frequency neurostimulation. If it is determined that the patient responds to high frequency neurostimulation, the system can then initiate delivery of the existing high frequency signal. In some embodiments, the delivery of the modified and existing high frequency signals overlap. In other embodiments, the delivery of the modified high frequency signals is terminated before delivering the existing high frequency signals.

In some embodiments, systems in accordance with the present technology can deliver a modified high frequency signal (e.g., modified high frequency signals having asymmetric bi-phasic pulses, modified high frequency signals having relatively long interphase intervals, and/or mono-phasic high frequency pulses administered via a juggling pattern) to one or more electrodes implanted in a patient at a first position having a relatively high perception threshold and deliver an existing high frequency signal to one or more electrodes implanted in the patient at a second position having a relatively low perception threshold. In some embodiments, the modified high frequency signals may require less energy than existing (e.g., symmetric) high frequency signals for a given amplitude. Accordingly, the modified high frequency signals can be administered to the first position having the relatively high perception threshold at a relatively high amplitude without substantially draining the system's power source.

In some embodiments, systems in accordance with the present technology can be programmed to generate both modified and existing high frequency signals. A user (e.g., the patient, a healthcare provider, etc.) can selectively activate the modified high frequency signal, the existing high frequency signal, or both the modified and existing high frequency signal. The user can select which signal to deliver using a user interface on a controller operably coupled to the signal generator.

8.0 Additional Expected Benefits Associated with Certain Embodiments

The foregoing embodiments can produce one or more of a variety of advantages, for the patient and/or practitioner, when compared with existing SCS therapy. Some of these benefits were described above. For example, the modified high frequency neuromodulation signals described herein can induce a more rapid onset of pain relief in a patient, which is beneficial to both the patient (faster pain relief) and the practitioner (easier to identify patient responders). In addition, the modified high frequency neuromodulation signals can modulate a target population of neurons in a different manner than existing high frequency neuromodulation signals, and thus can provide a supplementary and/or synergistic effect when delivered with existing high frequency neuromodulation.

In addition to the foregoing, the modified high frequency signals described herein can induce effective pain relief without patient-detectable disruptions to normal sensory and motor signals along the spinal cord. While the therapy may create some effect on normal motor and/or sensory signals, the effect is below a level that the patient can reliably detect intrinsically, e.g., without the aid of external assistance via instruments or other devices. Accordingly, the patient's levels of motor signaling and other sensory signaling (other than signaling associated with the target pain) can be maintained at pre-treatment levels. For example, the patient can experience a significant pain reduction that is largely independent of the patient's movement and position. In particular, the patient can assume a variety of positions and/or undertake a variety of movements associated with activities of daily living and/or other activities, without the need to adjust the parameters in accordance with which the therapy is applied to the patient (e.g., the signal amplitude). This result can greatly simplify the patient's life and reduce the effort required by the patient to experience pain relief while engaging in a variety of activities. This result can also provide an improved lifestyle for patients who experience pain during sleep.

Another expected benefit is that, similar to existing high frequency neuromodulation signals, the modified high frequency signals described herein are expected to produce pain relief in the patient without generating paresthesia. In contrast, existing low frequency neuromodulation (e.g., signals with frequencies less than 1.2 kHz) typically are commonly understood to rely on paresthesia (i.e., masking) to provide a therapeutic effect (i.e., pain relief). However, although described in the context of high frequency signals, the waveforms and administration patterns described herein could also be applied to low frequency signals, such as those having frequencies less than 1.2 kHz.

9.0 Representative Examples

The following examples are provided to further illustrate embodiments of the present technology and are not to be interpreted as limiting the scope of the present technology. To the extent that certain embodiments or features thereof are mentioned, it is merely for purposes of illustration and, unless otherwise specified, is not intended to limit the present technology. It will be understood that many variations can be made in the procedures described herein while still remaining within the bounds of the present technology. Such variations are intended to be included within the scope of the presently disclosed technology.

1. A patient treatment system, comprising:

a signal generator having a computer readable storage medium, wherein, in operation, the signal generator generates an electrical signal having bi-phasic pulses repeating at a frequency within a frequency range of about 1.2 kHz to about 500 kHz, wherein each bi-phasic pulse includes a first pulse phase having a first pulse width and a first polarity, a second pulse phase having a second pulse width and a second polarity opposite the first polarity, and an interphase interval between the first pulse phase and the second pulse phase, and wherein:

(a) a ratio of the second pulse phase pulse width to the first pulse phase pulse width is between 2:1 and 6:1, or (b) a ratio of a duration of the of the interphase interval to the first pulse phase pulse width is between 2:1 and 6:1, or (c) both (a) and (b); and a signal delivery element coupleable to the signal generator, wherein the signal delivery element is positionable proximate a target region, and, in operation, delivers the electrical signal to the target region.

2. The system of example 1 wherein the ratio of the second pulse phase pulse width to the first pulse phase pulse width is between 2:1 and 6:1.

3. The system of example 2 wherein the ratio of the second pulse phase pulse width to the first pulse phase pulse width is between 2:1 and 5:1.

4. The system of example 2 wherein the ratio of the second pulse phase pulse width to the first pulse phase pulse width is between 2:1 and 4:1.

5. The system of example 2 wherein the ratio of the second pulse phase pulse width to the first pulse phase pulse width is about 3:1.

6. The system of example 2 wherein the first pulse phase pulse width is in a pulse width range of about 1 microsecond to about 416 microseconds, and wherein the second pulse phase pulse width is in a pulse width range of about 2 microseconds to about 740 microseconds.

7. The system of any of examples 2-6 wherein the first pulse phase has a first amplitude and the second pulse phase has a second amplitude, and wherein the ratio between the second amplitude and the first amplitude is between 1:2 and 1:6.

8. The system of example 7 wherein the ratio between the second pulse phase amplitude and the first pulse phase amplitude is the inverse of the ratio between the second pulse phase pulse width and the first pulse phase pulse width such that the total charge delivered during the first pulse phase and the total charge delivered during the second pulse phase are equal and opposite.

9. The system of example 1 wherein the ratio of the duration of the interphase interval to the first pulse phase pulse width is between 2:1 and 6:1.

10. The system of example 9 wherein the ratio of the duration of the interphase interval to the first pulse phase pulse width is between 2:1 and 5:1.

11. The system of example 9 wherein the ratio of the duration of the interphase interval to the first pulse phase pulse width is between 2:1 and 4:1.

12. The system of example 9 wherein the ratio of the duration of the interphase interval to the first pulse phase pulse width is about 3:1.

13. The system of any of examples 9-12 wherein the duration of the interphase interval is between about 24 microseconds and about 160 microseconds.

14. The system of any of examples 9-12 wherein the duration of the interphase interval is between about 40 microseconds and about 80 microseconds.

15. The system of any of examples 1-14 wherein both (a) the ratio of the second pulse phase pulse width to the first pulse phase pulse width is between 2:1 and 6:1, and (b) the ratio of the duration of the interphase interval to the first pulse phase pulse width is between 2:1 and 6:1.

16. The system of any of examples 1-15 wherein the first pulse phase is an anodic pulse phase and the second pulse phase is a cathodic pulse phase.

17. The system of any of examples 1-15 wherein the first pulse phase is a cathodic pulse phase and the second pulse phase is an anodic pulse phase.

18. The system of any of examples 1-17 wherein the first pulse phase is a therapy pulse phase and the second pulse phase is a charge balancing pulse phase.

19. The system of any of examples 1-18 wherein the frequency is in a frequency range of from about 1.2 kHz to about 50 kHz.

20. The system of any of examples 1-18 wherein the frequency is in a frequency range of from about 3 kHz to about 15 kHz.

21. The system of any of examples 1-20 wherein the electrical signal is a first electrical signal, and wherein, in operation, the signal generator further generates a second electrical signal having bi-phasic pulses repeating at a frequency within a frequency range of about 1.2 kHz to about 500 kHz, wherein the bi-phasic pulses of the second electrical signal have a third pulse phase having a third pulse width and a third polarity, a fourth pulse phase having a fourth pulse width and a fourth polarity opposite the third polarity, and an interphase interval between the third pulse phase and the second pulse phase, and wherein:

(a) the third pulse phase pulse width is approximately equal to the fourth pulse phase pulse width; and (b) the duration of the interphase interval is less than or equal to the third pulse phase pulse width.

22. The system of example 21 wherein, in operation, the system generates and delivers the first electrical signal and the second electrical signal simultaneously.

23. The system of example 21 wherein, in operation, the system generates and delivers the first electrical signal and the second electrical signal sequentially.

24. A method of treating a patient, comprising:

programming a signal generator to generate an electrical signal having bi-phasic pulses repeating at a frequency within a frequency range of about 1.2 kHz to about 500 kHz, wherein each bi-phasic pulse includes a first pulse phase having a first pulse width and a first polarity, a second pulse phase having a second pulse width and a second polarity opposite the first polarity, and an interphase interval between the first pulse phase and the second pulse phase, and wherein:

(a) a ratio of the second pulse phase pulse width to the first pulse phase pulse width is between 2:1 and 6:1, or (b) a ratio of a duration of the of the interphase interval to the first pulse phase pulse width is between 2:1 and 6:1, or (c) both (a) and (b).

25. The method of example 24 wherein the ratio of the second pulse phase pulse width to the first pulse phase pulse width is between 2:1 and 6:1.

26. The method of example 25 wherein the ratio of the second pulse phase pulse width to the first pulse phase pulse width is between 2:1 and 5:1.

27. The method of example 25 wherein the ratio of the second pulse phase pulse width to the first pulse phase pulse width is between 2:1 and 4:1.

28. The method of example 25 wherein the ratio of the second pulse phase pulse width to the first pulse phase pulse width is about 3:1.

29. The method of example 25 wherein the first pulse phase pulse width is in a pulse width range of about 1 microsecond to about 416 microseconds, and wherein the second pulse phase pulse width is in a pulse width range of about 2 microseconds to about 740 microseconds.

30. The method of any of examples 25-29 wherein the first pulse phase has a first amplitude and the second pulse phase has a second amplitude, and wherein the ratio between second amplitude and the first amplitude is between 1:2 and 1:6.

31. The method of example 30 wherein the ratio between the second pulse phase amplitude and the first pulse phase amplitude is the inverse of the ratio between the second pulse phase pulse width and the first pulse phase pulse width such that the total charge delivered during the first pulse phase and the total charge delivered during the second pulse phase are equal and opposite.

32. The method of example 24 wherein the ratio of the duration of the interphase interval to the first pulse phase pulse width is between 2:1 and 6:1.

33. The method of example 32 wherein the ratio of the duration of the interphase interval to the first pulse phase pulse width is between 2:1 and 5:1.

34. The method of example 32 wherein the ratio of the duration of the interphase interval to the first pulse phase pulse width is between 2:1 and 4:1.

35. The method of example 32 wherein the ratio of the duration of the interphase interval to the first pulse phase pulse width is about 3:1.

36. The method of any of examples 32-35 wherein the duration of the interphase interval is between about 24 microseconds and about 160 microseconds.

37. The method of any of examples 32-35 wherein the duration of the interphase interval is between about 40 microseconds and about 80 microseconds.

38. The method of any of examples 24-37 wherein both (a) the ratio of the second pulse phase pulse width to the first pulse phase pulse width is between 2:1 and 6:1, and (b) the ratio of a duration of the of the interphase interval to the first pulse phase pulse width is between 2:1 and 6:1.

39. The method of any of examples 24-38 wherein the first pulse phase is an anodic pulse phase and the second pulse phase is a cathodic pulse phase.

40. The method of any of examples 24-38 wherein the first pulse phase is a cathodic pulse phase and the second pulse phase is an anodic pulse phase.

41. The method of any of examples 24-40 wherein the first pulse phase is a therapy pulse phase and the second pulse phase is a charge balancing pulse phase.

42. The method of any of examples 24-41 wherein the frequency is in a frequency range of from about 1.2 kHz to about 50 kHz.

43. The method of any of examples 24-41 wherein the frequency is in a frequency range of from about 3 kHz to about 15 kHz.

44. The method of any of examples 24-43 wherein the electrical signal is a first electrical signal, the method further comprising:

programming the signal generator to generate a second electrical signal having bi-phasic pulses repeating at a frequency within a frequency range of about 1.2 kHz to about 500 kHz, wherein the bi-phasic pulses of the second electrical signal have a third pulse phase having a third pulse width and a third polarity, a fourth pulse phase having a fourth pulse width and a fourth polarity opposite the third polarity, and an interphase interval between the third pulse phase and the second pulse phase, and wherein:
  (a) the third pulse phase pulse width is approximately equal to the fourth pulse phase pulse width; and
  (b) the duration of the interphase interval is less than or equal to the third pulse phase pulse width.

45. The method of example 44 wherein programming the signal generator includes programming the signal generator to simultaneously generate the first electrical signal and the second electrical signal.

46. The method of example 44 wherein programming the signal generator includes programming the signal generator to generate the first electrical signal before generating the second electrical signal.

47. The method of any of examples 44-46 wherein the first electrical signal preferentially activates a first set of target neurons, and wherein the second electrical signal preferentially activates a second set of target neurons.

48. The method of example 47 wherein the first set of target neurons includes excitatory neurons and the second set of target neurons includes inhibitory neurons.

49. The method of any of examples 44-48 wherein the first electrical signal induces a first physiological effect, and wherein the second electrical signal induces a second physiological effect different than the first physiological effect.

50. A patient treatment system, comprising:
  a signal generator having a computer readable storage medium, wherein, in operation, the signal generator generates an electrical signal having pulses repeating at a frequency within a frequency range of about 1.2 kHz to about 500 kHz; and
  a signal delivery element positionable in a target region and having at least three contacts, wherein the signal delivery element is coupleable to the signal generator, and, in operation, delivers the electrical signal to the target region via the at least three contacts,
  wherein an individual pulse is delivered via a pair of contacts that is different than the pair of contacts used to deliver the immediately preceding pulse.

51. The system of example 50 wherein (a) the at least three contacts includes a first contact, a second contact, and a third contact, and (b) the pulses include a first pulse, a second pulse, and a third pulse, and wherein, in operation:
  the first pulse is delivered via the first and second contacts,
  the second pulse is delivered via the second and third contacts, and
  the third pulse is delivered via the third and first contacts.

52. The system of example 51 wherein:
  during delivery of the first pulse, current flows out of the first contact and into the second contact,
  during delivery of the second pulse, current flows out of the second contact and into the third contact, and
  during delivery of the third pulse, current flows out of the third contact and into the first contact.

53. The system of examples 51 or 52 wherein the first pulse, the second pulse, and the third pulse have the same amplitude and pulse width.

54. The system of examples 51 or 52 wherein at least one of the first pulse, the second pulse, and the third pulse has an amplitude and/or pulse width that is different than an amplitude and/or pulsed width of at least one of the other of the first pulse, the second pulse, or the third pulse.

55. The system of example 54 wherein the total charge delivered by the first pulse, the second pulse, and the third pulse is the same.

56. The system of any of examples 50-55 wherein the signal delivery element includes more than three contacts.

57. The system of any of examples 50-56 wherein the frequency is in a frequency range of from about 1.2 kHz to about 50 kHz.

58. The system of any of examples 50-56 wherein the frequency is in a frequency range of from about 3 kHz to about 15 kHz.

59. A method of treating a patient, comprising:

programming a patient treatment system having a signal generator and a signal delivery element to:

generate, via the signal generator, an electrical signal having pulses repeating at a frequency within a frequency range of about 1.2 kHz to about 500 kHz; and deliver, via the signal delivery element, the electrical signal to the target region, wherein the signal delivery element includes at least three contacts, and wherein the system is programmed such that an individual pulse is delivered via a pair of contacts that is different than the pair of contacts used to deliver the immediately preceding pulse.

60. The method of example 59 wherein (a) the at least three contacts include a first contact, a second contact, and a third contact, and (b) the pulses include a first pulse, a second pulse, and a third pulse and wherein programming the patient treatment system includes programing the patient treatment system such that:

the first pulse is delivered via the first and second contacts, the second pulse is delivered via the second and third contacts, and the third pulse is delivered via the third and first contacts.

61. The method of example 60 wherein programming the patient treatment system includes programming the patient treatment system such that:

during delivery of the first pulse, current flows out of the first contact and into the second contact, during delivery of the second pulse, current flows out of the second contact and into the third contact, and during delivery of the third pulse, current flows out of the third contact and into the first contact.

62. The method of examples 60 or 61 wherein the first pulse, the second pulse, and the third pulse have the same amplitude and pulse width.

63. The method of examples 60 or 61 wherein at least one of the first pulse, the second pulse, and the third pulse has an amplitude and/or pulse width that is different than an amplitude and/or pulsed width of at least one of the other of the first pulse, the second pulse, or the third pulse.

64. The method of example 63 wherein the total charge delivered by the first pulse, the second pulse, and the third pulse is the same.

65. The method of any of examples 59-64 wherein the signal delivery element includes more than three contacts.

66. The method of any of examples 59-65 wherein the frequency is in a frequency range of from about 1.2 kHz to about 50 kHz.

67. The method of any of examples 59-65 wherein the frequency is in a frequency range of from about 3 kHz to about 15 kHz.

68. The method of any of examples 59-67 wherein the electrical signal preferentially modulates a first set of target neurons when administered at a first amplitude, and wherein the electrical signal preferentially modulates a second set of target neurons different than the first set when administered at a second amplitude.

69. The method of example 68 wherein the first amplitude is greater than or equal to 30 percent of motor threshold, and wherein the first set of target neurons includes excitatory neurons.

70. The method of example 68 or 69 wherein the second amplitude is less than or equal to 10 percent of motor threshold, and wherein the second set of target neurons includes inhibitory neurons.

10.0 Conclusion

From the foregoing, it will be appreciated that specific embodiments of the disclosed technology have been described herein for purposes of illustration, but that various modifications can be made without deviating from the technology. For example, therapy signals described herein can be delivered at combinations of parameter values within the foregoing ranges at values that are not expressly disclosed herein. Certain aspects of the technology described in the context of particular embodiments can be combined or eliminated in other embodiments. In some embodiments, the foregoing techniques can be used to address patient deficits than pain. Further, while advantages associated with certain embodiments of the disclosed technology have been described in the context of those embodiments, other embodiments may also exhibit such advantages, and not all embodiments need necessarily exhibit such advantages to fall within the scope of the present technology. Accordingly, the disclosure and associated technology can encompass other embodiments not expressly shown or described herein.

The use of "and/or" in reference to a list of two or more items is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications can be made without deviating from the technology. Further, while advantages associated with certain embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

Where a range of values is provided, it is understood that each intervening value, to the tenth of the unit of the lower limit unless the context clearly dictates otherwise, to between the upper and lower limits of that range is also specifically disclosed. Each smaller range between any stated value or intervening value in a stated range and any other stated or intervening value in that stated range is encompassed within the disclosure. The upper and lower limits of these smaller ranges can independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

To the extent any materials incorporated herein by reference conflict with the present disclosure, the present disclosure controls.

We claim:

1. A patient treatment system, comprising:
a signal generator having a computer readable storage medium, wherein, in operation, the signal generator generates an electrical signal having bi-phasic pulses repeating at a frequency within a frequency range of about 1.2 kHz to about 500 kHz, wherein each bi-phasic pulse includes a first pulse phase having a first pulse width and a first polarity, a second pulse phase having a second pulse width and a second polarity opposite the first polarity, and an interphase interval between the first pulse phase and the second pulse phase, and wherein:
the interphase interval has a duration of between about 24 microseconds and about 160 microseconds, and
a ratio of the duration of the interphase interval to the first pulse width is between 2:1 and 6:1; and
a signal delivery element coupleable to the signal generator, wherein the signal delivery element is positionable proximate a target region, and, in operation, delivers the electrical signal to the target region
wherein the signal deliver element includes a first contact and a second contact and a third contact, the first pulse being delivered via the first contact and the second contact, and the second pulse being delivered via the second contact and the third contact,
wherein the first and second pulse delivered via the first, second and third contacts is different than the pair of contacts used to deliver an immediately preceding pulse.

2. A method of treating a patient, comprising:
programming a signal generator to generate an electrical signal having bi-phasic pulses repeating at a frequency within a frequency range of about 1.2 kHz to about 500 kHz, wherein each bi-phasic pulse includes a first pulse phase having a first pulse width and a first polarity, a second pulse phase having a second pulse width and a second polarity opposite the first polarity, and an interphase interval between the first pulse phase and the second pulse phase, and wherein:
the interphase interval has a duration of between about 24 microseconds and about 160 microseconds, and a ratio of the duration of the interphase interval to the first pulse width is between 2:1 and 6:1,
delivering the electrical signal to the target region, wherein the step of delivering the electrical signal includes providing a signal deliver element having a first contact and a second contact and a third contact, the first pulse being delivered via the first contact and the second contact, and the second pulse being delivered via the second contact and the third contact,
wherein the first and second pulse delivered via the first, second and third contacts is different than the pair of contacts used to deliver an immediately preceding pulse.

3. The method of claim 2 wherein the ratio of the duration of the interphase interval to the first pulse width is between 2:1 and 5:1.

4. The method of claim 2 wherein the ratio of the duration of the interphase interval to the first pulse width is between 2:1 and 4:1.

5. The method of claim 2 wherein the ratio of the duration of the interphase interval to the first pulse width is about 3:1.

6. The method of claim 2 wherein the duration of the interphase interval is between about 30 microseconds and about 120 microseconds.

7. The method of claim 2 wherein the duration of the interphase interval is between about 40 microseconds and about 80 microseconds.

8. The method of claim 2 wherein a ratio of the second pulse width to the first pulse width is between 2:1 and 6:1.

9. The method of claim 2 wherein the first pulse phase is an anodic pulse phase and the second pulse phase is a cathodic pulse phase.

10. The method of claim 2 wherein the first pulse phase is a cathodic pulse phase and the second pulse phase is an anodic pulse phase.

11. The method of claim 2 wherein the first pulse phase is a therapy pulse phase and the second pulse phase is a charge balancing pulse phase.

12. The method of claim 2 wherein the frequency is in a frequency range of from about 1.2 kHz to about 50 kHz.

13. The method of claim 2 wherein the frequency is in a frequency range of from about 3 kHz to about 15 kHz.

14. The method of claim 2 wherein the electrical signal is a first electrical signal, the method further comprising:
programming the signal generator to generate a second electrical signal having bi-phasic pulses repeating at a frequency within a frequency range of about 1.2 kHz to about 500 kHz, wherein the bi-phasic pulses of the second electrical signal have a third pulse phase having a third pulse width and a third polarity, a fourth pulse phase having a fourth pulse width and a fourth polarity opposite the third polarity, and an interphase interval between the third pulse phase and the second pulse phase, and wherein:
(a) the third pulse width is approximately equal to the fourth pulse width; and
(b) the duration of the interphase interval is less than or equal to the third pulse width.

15. The method of claim 14 wherein programming the signal generator includes programming the signal generator to simultaneously generate the first electrical signal and the second electrical signal.

16. The method of claim 14 wherein programming the signal generator includes programming the signal generator to generate the first electrical signal before generating the second electrical signal.

17. The method of claim 14 wherein the first electrical signal preferentially activates a first set of target neurons, and wherein the second electrical signal preferentially activates a second set of target neurons.

18. The method of claim 17 wherein the first set of target neurons includes excitatory neurons and the second set of target neurons includes inhibitory neurons.

19. The method of claim 14 wherein the first electrical signal induces a first physiological effect, and wherein the second electrical signal induces a second physiological effect different than the first physiological effect.

20. A method of treating a patient, comprising:
programming a signal generator to generate an electrical signal having bi-phasic pulses repeating at a frequency within a frequency range of about 1.2 kHz to about 500 kHz, wherein each bi-phasic pulse includes a first pulse phase having a first pulse width and a first polarity, a second pulse phase having a second pulse width and a second polarity opposite the first polarity, and an inter-phase interval between the first pulse phase and the second pulse phase, and wherein:

the first pulse width is within a pulse width range of from about 1 microsecond to about 416 microseconds, and a ratio of the second pulse width to the first pulse width is between 2:1 and 6:1 delivering the electrical signal to the target region, wherein the step of delivering the electrical signal includes providing a signal deliver element having a first contact and a second contact and a third contact, the first pulse being delivered via the first contact and the second contact, and the second pulse being deliv-ered via the second contact and the third contact, wherein the first and second pulse delivered via the first, second and third contacts is different than the pair of contacts used to deliver an immediately preceding pulse.

21. The method of claim 20 wherein the ratio of the second pulse width to the first pulse width is between 2:1 and 5:1.

34

22. The method of claim 20 wherein the ratio of the second pulse width to the first pulse width is between 2:1 and 4:1.

23. The method of claim 20 wherein the ratio of the second pulse width to the first pulse width is about 3:1.

24. The method of claim 20 wherein the first pulse width is in a pulse width range of about 1 microsecond to about 416 microseconds, and wherein the second pulse width is in a pulse width range of about 2 microseconds to about 740 microseconds.

25. The method of claim 20 wherein the first pulse phase has a first amplitude and the second pulse phase has a second amplitude, and wherein the ratio between the second ampli-tude and the first amplitude is between 1:2 and 1:6.

26. The method of claim 25 wherein the ratio between the second pulse phase amplitude and the first pulse phase amplitude is the inverse of the ratio between the second pulse width and the first pulse width such that the total charge delivered during the first pulse phase and the total charge delivered during the second pulse phase are equal and opposite.

* * * * *